(12) United States Patent
Cuconati et al.

(10) Patent No.: US 10,087,173 B2
(45) Date of Patent: Oct. 2, 2018

(54) SUBSTITUTED AMINOTHIAZOLES AS INHIBITORS OF CANCERS, INCLUDING HEPATOCELLULAR CARCINOMA, AND AS INHIBITORS OF HEPATITIS VIRUS REPLICATION

(71) Applicants: BARUCH S. BLUMBERG INSTITUTE, Doylestown, PA (US); DREXEL UNIVERSITY, Philadelphia, PA (US)

(72) Inventors: Andrea Cuconati, Oreland, PA (US); Xiaodong Xu, Doylestown, PA (US); Timothy M. Block, Doylestown, PA (US)

(73) Assignees: Baruch S. Blumberg Institute; Drexel University

( * ) Notice: Subject to any disclaimer, the term of this patent is extended or adjusted under 35 U.S.C. 154(b) by 0 days.

(21) Appl. No.: 15/258,393

(22) Filed: Sep. 7, 2016

(65) Prior Publication Data

US 2017/0066758 A1    Mar. 9, 2017

Related U.S. Application Data

(63) Continuation of application No. 14/349,014, filed as application No. PCT/US2012/058674 on Oct. 4, 2012, now abandoned.

(60) Provisional application No. 61/542,907, filed on Oct. 4, 2011.

(51) Int. Cl.

| | |
|---|---|
| *C07D 417/14* | (2006.01) |
| *A61K 31/425* | (2006.01) |
| *A61K 31/426* | (2006.01) |
| *C07D 277/42* | (2006.01) |
| *C07D 417/04* | (2006.01) |
| *C07D 417/12* | (2006.01) |
| *C07D 487/04* | (2006.01) |
| *C07D 495/04* | (2006.01) |

(52) U.S. Cl.
CPC .......... *C07D 417/14* (2013.01); *A61K 31/425* (2013.01); *A61K 31/426* (2013.01); *C07D 277/42* (2013.01); *C07D 417/04* (2013.01); *C07D 417/12* (2013.01); *C07D 487/04* (2013.01); *C07D 495/04* (2013.01); *Y02A 50/463* (2018.01)

(58) Field of Classification Search
CPC .............................. C07D 417/14; A61K 31/427

USPC .......................... 544/328, 331; 514/256, 275
See application file for complete search history.

(56) References Cited

U.S. PATENT DOCUMENTS

| | | |
|---|---|---|
| 7,105,550 B2 | 9/2006 | Love et al. |
| 2005/0227989 A1 | 10/2005 | Wang et al. |
| 2007/0203147 A1 | 8/2007 | Coburn et al. |
| 2007/0213301 A1 | 9/2007 | Zhang et al. |

FOREIGN PATENT DOCUMENTS

| | | |
|---|---|---|
| WO | 2003015773 A2 | 2/2003 |
| WO | 2005099673 A1 | 10/2005 |
| WO | 2006122011 A2 | 11/2006 |
| WO | 2007103550 A2 | 9/2007 |
| WO | 2008083098 A1 | 7/2008 |
| WO | 2009114552 A1 | 9/2009 |
| WO | 2010111711 A2 | 9/2010 |

OTHER PUBLICATIONS

ChemBridge Corporation, RN 471914-98-4, 2002.*
ChemBridge Corporation, RN 472979-19-4, 2002.*
Banker, G.S. et al., "Prodrugs," Modern Pharmaceutics, Third Edition, Revised and Expanded, 1996, pp. 451 and 596.
Bundgaard, H., "Design of Prodrugs: Bioreversible Derivatives for Various Functional Groups and Chemical Entities," Design of Prodrugs, Elsevier Science Publishers B.V. (Biomedical Division), 1985, p. 1.
Dighe, S.N. et al., "A Remarkably High-Speed Solution-Phase Combinatorial Synthesis of 2-Subsituted-Amino-4-Aryl Thiazoles in Polar Solvents in the Absence of a Catalyst under Ambient Conditions and Study of Their Antimicrobial Activities," ISRN Organic Chemistry, vol. 2011, No. 434613, 6 pp., URL: http://downloads.hindawi.com/ISRN/OC/2011/434613.pdf.
Hay, M.P. et al., "4-Pyridylanilinothiazoles that Selectively Target von Hippel-Lindau Deficient Renal Cell Carcinoma Cells by Inducing Autophagic Cell Death," J. Med. Chem., vol. 53, No. 2, pp. 787-797, 2010.
Wolf, M.E., "Some Considerations for Prodrug Design," Burger's Medicinal Chemistry and Drug Discovery, 5th Edition, vol. 1: Principles and Practice, 1995, pp. 975-977.

* cited by examiner

*Primary Examiner* — Deepak R Rao
(74) *Attorney, Agent, or Firm* — The Belles Group, P.C.

(57) ABSTRACT

Pharmaceutical compositions of the invention comprise substituted aminothiazoles derivatives having a disease-modifying action in the treatment of diseases associated with unregulated cell growth that include hepatocellular carcinoma, and infection with a hepatitis virus.

5 Claims, No Drawings

SUBSTITUTED AMINOTHIAZOLES AS INHIBITORS OF CANCERS, INCLUDING HEPATOCELLULAR CARCINOMA, AND AS INHIBITORS OF HEPATITIS VIRUS REPLICATION

CROSS-REFERENCE TO RELATED APPLICATIONS

This application is a continuation of U.S. patent application Ser. No. 14/349,014, filed Apr. 1, 2014, which is the national phase application filed under 35 U.S.C. § 371 of PCT Application No. PCT/US2012/058674, filed Oct. 4, 2012, which claims priority under 35 U.S.C. § 119(e) to U.S. Provisional Application No. 61/542,907, filed Oct. 4, 2011, all of which applications are hereby incorporated herein by reference in their entireties.

FIELD OF INVENTION

The present invention describes compounds and methods useful for the treatment of cancer, including primary liver cancer, hepatocellular carcinoma, hepatoblastoma, and cholangiocarcinoma, and the treatment of viral hepatitis infection, including but not limited to hepatitis A virus infection, hepatitis B virus infection, hepatitis C virus infection, hepatitis D virus infection, and hepatitis E virus infection, as well as other viral species that infect the liver.

BACKGROUND OF THE INVENTION

Primary liver cancer is currently the fifth most common cause of cancer deaths among men, and ninth among women in the US, with the numbers increasing yearly. The most recent data indicate that in 2008 there were an estimated 21,370 new cases of liver and bile duct cancer of which the majority are hepatocellular carcinomas (HCCs), with 18,410 deaths (Institute, N.C., SEER Cancer Statistics Review, 1975-2005, Ries L A G, et al., Editors. 2008.). Worldwide, it is the fourth most common cancer, with approximately 663,00 fatal cases reported in 2008; based on current trends and baseline models, the incidence is expected to rise to 756,000 in 2015, and 955,000 in 2030 (Mathers, C. D. and D. Loncar, Projections of global mortality and burden of disease from 2002 to 2030. PLoS Med, 2006. 3, 11, p. e442.). Although it is comparatively uncommon in the US, its incidence has been rising over the last 20 years partially as a result of burgeoning numbers of cases of chronic hepatitis C (Caldwell, S. and S. H. Park, The epidemiology of hepatocellular cancer: from the perspectives of public health problem to tumor biology. J Gastroenterol, 2009. 44 Suppl 19: p. 96-101. El-Serag, H. B., et al., The continuing increase in the incidence of hepatocellular carcinoma in the United States: an update. Ann Intern Med, 2003. 139(10): p. 817-23) one of the principal causes along with hepatitis B and aflatoxin exposure.

There is a long felt need for new drugs that are both disease-modifying and effective in treating patients with primary liver cancer, including but not limited to hepatocellular carcinoma, hepatoblastoma, and cholangiocarcinoma. There is also a clear and present need for new therapeutic agents that are both disease modifying and effective in treating patients that are infected with a hepatitis virus. The present invention addresses the need for new drugs that are both disease-modifying and effective in treating patients suffering from primary liver cancer and hepatocellular carcinoma. Because the present invention targets the cell types that have been demonstrated to support viral infection in the liver, the present invention addresses also the need for new antiviral drugs that are both disease-modifying and effective in treating patients that are infected with hepatitis A virus, hepatitis B virus, hepatitis C virus, hepatitis D virus, and hepatitis E virus., as well as other viral species that infect the liver.

BRIEF SUMMARY OF THE INVENTION

The present invention is directed toward novel substituted aminothiazoles, compounds of formula (I),

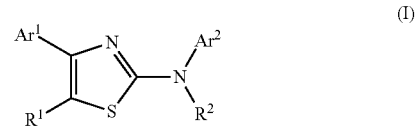

Including hydrates, solvates, pharmaceutically acceptable salts, prodrugs and complexes thereof, wherein:
$R^1$ is selected from a group consisting of hydrogen, $C_1$-$C_9$ linear alkyl, isopropyl, cyclohexyl, bromine, cyano,

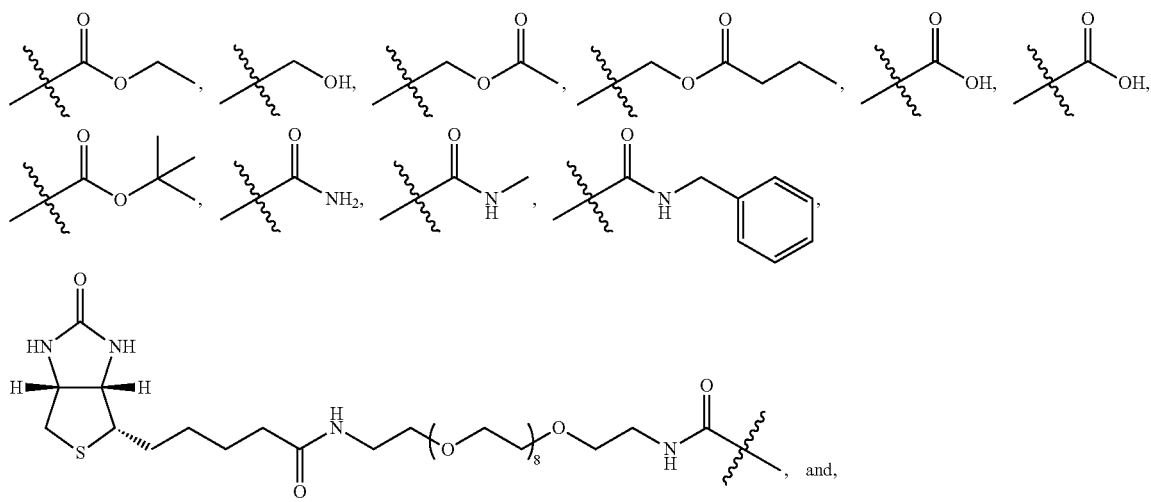

-continued
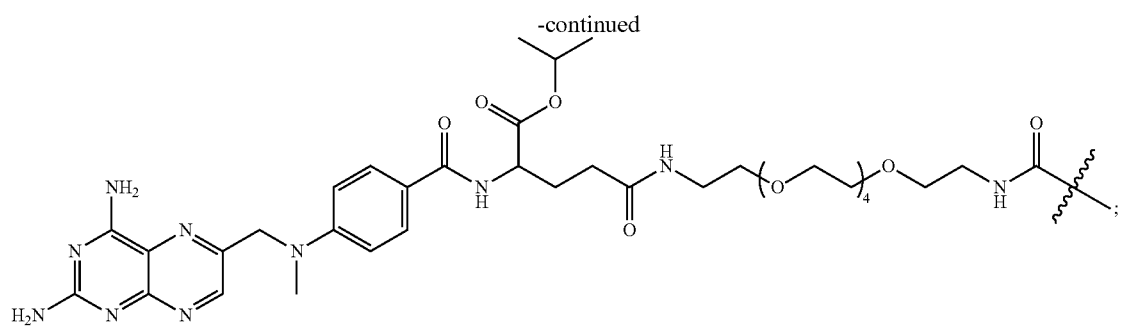
$R^2$ is selected from a group consisting of hydrogen, methyl, isopropyl, tert-butyl, benzyl, and
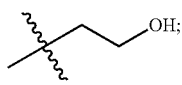 [SMILES: *CCO]
$Ar^1$ is selected from a group consisting of phenyl,
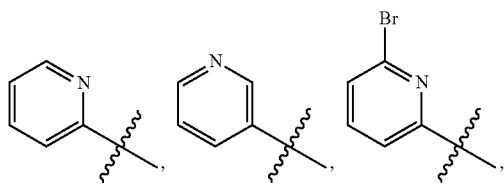
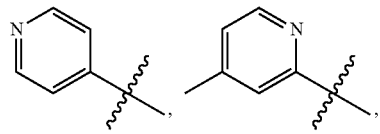
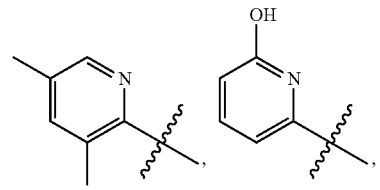
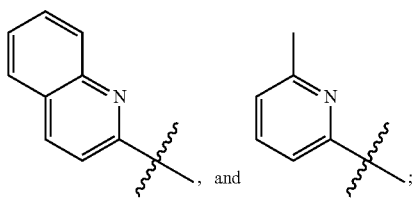
$Ar^2$ is selected from a group consisting of phenyl,
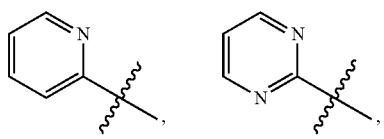
-continued
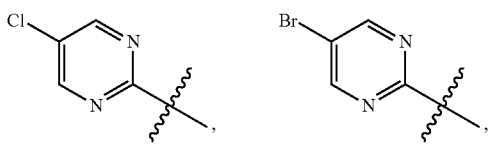
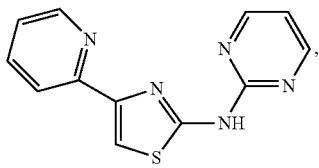
Compounds of the structures
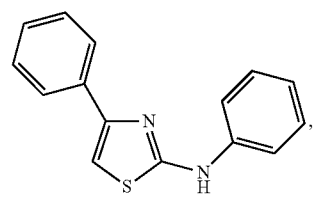

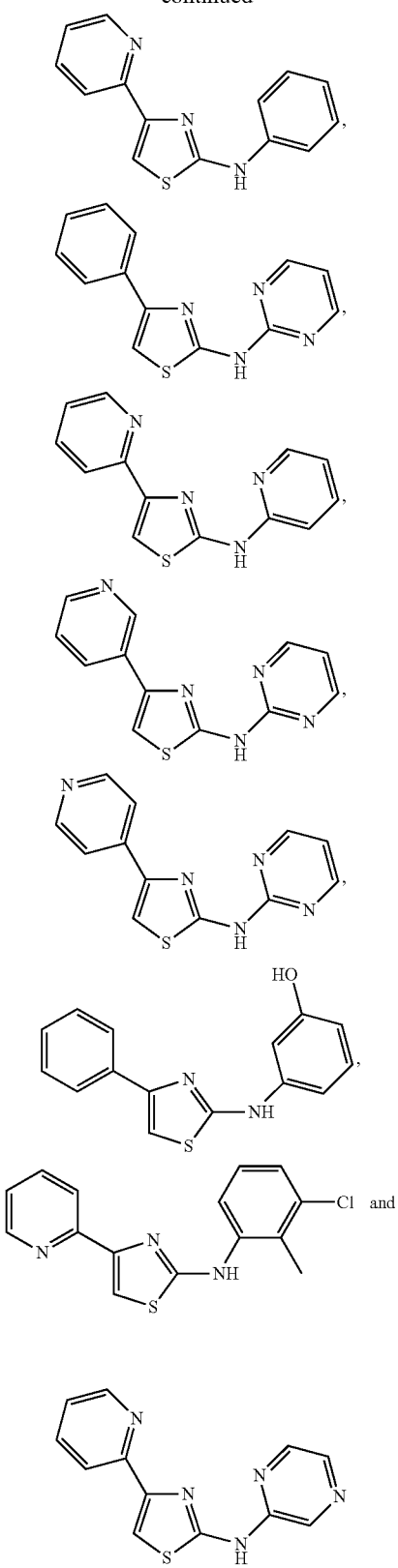

are excluded from the novel compounds of formula (I).

The present invention is also directed toward novel methods of use of compounds of the structure $$\underset{R^1}{\overset{Ar^1}{\underset{S}{\bigvee}}}\overset{N}{\underset{R^2}{\bigvee}}\overset{Ar^2}{\underset{R^2}{N}}.$$ (I)

The present invention further relates to compositions comprising: an effective amount of one or more compounds according to the present invention and an excipient.

The present invention also relates to a method for treating or preventing diseases that involve unregulated cell growth, including, for example, primary liver cancer, hepatocellular carcinoma, hepatoblastoma, cholangiocarcinoma breast cancer, ovarian cancer, lung cancer, leukemia, and metastatic disease, said method comprising administering to a subject an effective amount of a compound or composition according to the present invention.

The present invention yet further relates to a method for treating or preventing diseases that involve unregulated cell growth, including, for example, primary liver cancer, hepatocellular carcinoma, hepatoblastoma, and cholangiocarcinoma, breast cancer, ovarian cancer, lung cancer, leukemia, and metastatic disease, wherein said method comprises administering to a subject a composition comprising an effective amount of one or more compounds according to the present invention and an excipient.

The present invention also relates to a method for treating or preventing disease or conditions associated with primary liver cancer, hepatocellular carcinoma, hepatoblastoma, and cholangiocarcinoma, breast cancer, ovarian cancer, lung cancer, leukemia, and metastatic disease, and diseases that involve unregulated cell growth. Said methods comprise administering to a subject an effective amount of a compound or composition according to the present invention.

The present invention yet further relates to a method for treating or preventing disease or conditions associated with primary liver cancer, hepatocellular carcinoma, hepatoblastoma, and cholangiocarcinoma, breast cancer, ovarian cancer, lung cancer, leukemia, and metastatic disease, and diseases that involve unregulated cell growth, wherein said method comprises administering to a subject a composition comprising an effective amount of one or more compounds according to the present invention and an excipient.

The present invention also relates to a method for treating or preventing disease or conditions associated with unregulated cell growth. Said methods comprise administering to a subject an effective amount of a compound or composition according to the present invention.

The present invention yet further relates to a method for treating or preventing disease or conditions associated with unregulated cell growth, wherein said method comprises administering to a subject a composition comprising an effective amount of one or more compounds according to the present invention and an excipient.

The present invention also relates to a method for treating or preventing diseases that involve infection with a hepatits virus, including, for example, hepatitis A virus, hepatitis B virus, hepatitis C virus, hepatitis D virus, and hepatitis E virus, as well as other viral species that infect the liver, said method comprising administering to a subject an effective amount of a compound or composition according to the present invention.

The present invention yet further relates to a method for treating or preventing diseases that involve infection with a hepatitis virus, including, for example, hepatitis A virus, hepatitis B virus, hepatitis C virus, hepatitis D virus, and hepatitis E virus, as well as other viral species that infect the liver, wherein said method comprises administering to a subject a composition comprising an effective amount of one or more compounds according to the present invention and an excipient.

The present invention also relates to a method for treating or preventing disease or conditions associated with hepatitis A virus, hepatitis B virus, hepatitis C virus, hepatitis D virus, and hepatitis E virus, and diseases that involve infection with a hepatits virus as well as other viral species that infect the liver. Said methods comprise administering to a subject an effective amount of a compound or composition according to the present invention.

The present invention yet further relates to a method for treating or preventing disease or conditions associated with hepatitis A virus, hepatitis B virus, hepatitis C virus, hepatitis D virus, and Hepatitis E virus, and diseases that involve infection with a hepatits virus as well as other viral species that infect the liver, wherein said method comprises administering to a subject a composition comprising an effective amount of one or more compounds according to the present invention and an excipient.

The present invention also relates to a method for treating or preventing disease or conditions associated with infection with a hepatits virus, as well as other viral species that infect the liver. Said methods comprise administering to a subject an effective amount of a compound or composition according to the present invention.

The present invention yet further relates to a method for treating or preventing disease or conditions associated with infection with a hepatits virus, as well as other viral species that infect the liver, wherein said method comprises administering to a subject a composition comprising an effective amount of one or more compounds according to the present invention and an excipient.

The present invention further relates to a process for preparing the compounds of the present invention.

These and other objects, features, and advantages will become apparent to those of ordinary skill in the art from a reading of the following detailed description and the appended claims. All percentages, ratios and proportions herein are by weight, unless otherwise specified. All temperatures are in degrees Celsius (° C.) unless otherwise specified. All documents cited are in relevant part, incorporated herein by reference; the citation of any document is not to be construed as an admission that it is prior art with respect to the present invention.

DETAILED DESCRIPTION OF THE INVENTION

The substituted aminothiazoles of the present invention are capable of treating and preventing diseases associated with unregulated cell growth, for example primary liver cancer hepatocellular carcinoma, hepatoblastoma, and cholangiocarcinoma, breast cancer, ovarian cancer, lung cancer, leukemia, and metastatic disease. The substituted aminothiazoles of the present invention are also capable of treating and preventing diseases associated with infection with a hepatits virus, for example hepatitis A virus, hepatitis B virus, hepatitis C virus, hepatitis D virus, and hepatitis E virus, as well as other viruses that infect the liver It has been discovered that compounds of the disclosure cause cell cycle arrest and apoptosis in hepatocellular carcinoma (HCC)-derived cells as well as hepatoblastoma, breast cancer cells, and ovarian carcinoma cells. In addition, it has been determined that the effect on sensitive cells, for example HCC-derived cells as well as hepatoblastoma, breast cancer cells, and ovarian carcinoma cells, is non-reversible, and that the compounds of the disclosure act through inhibition of mitotic anti-apoptotic signaling by the regulatory kinases AKT, mTORC1 and mTORC2. Further, the substituted aminothiazoles of the disclosure destroy cells that support infection with a hepatits virus, for example hepatitis A virus, hepatitis B virus, hepatitis C virus, hepatitis D virus, and Hepatitis E virus, such as (cell type to support Hepatitis infection), and can serve as antiviral agents for the treatment and prevention of diseases associated with infection with a hepatits virus, for example hepatitis A virus, hepatitis B virus, hepatitis C virus, hepatitis D virus, and Hepatitis E virus, as well as other viral species that infect the liver.

Without wishing to be limited by theory, it is believed that the substituted aminothiazoles of the disclosure can ameliorate, abate, otherwise cause to be controlled, diseases associated unregulated cell growth. In addition, and also without wishing to be limited by theory, it is believed that the substituted aminothiazoles of the disclosure can ameliorate, abate, otherwise cause to be controlled, diseases associated with infection of the liver with a virus Throughout the description, where compositions are described as having, including, or comprising specific components, or where processes are described as having, including, or comprising specific process steps, it is contemplated that compositions of the present teachings also consist essentially of, or consist of, the recited components, and that the processes of the present teachings also consist essentially of, or consist of, the recited processing steps.

In the application, where an element or component is said to be included in and/or selected from a list of recited elements or components, it should be understood that the element or component can be any one of the recited elements or components and can be selected from a group consisting of two or more of the recited elements or components.

The use of the singular herein includes the plural (and vice versa) unless specifically stated otherwise. In addition, where the use of the term "about" is before a quantitative value, the present teachings also include the specific quantitative value itself, unless specifically stated otherwise.

It should be understood that the order of steps or order for performing certain actions is immaterial so long as the present teachings remain operable. Moreover, two or more steps or actions can be conducted simultaneously As used herein, the term "halogen" shall mean chlorine, bromine, fluorine and iodine.

As used herein, unless otherwise noted, "alkyl" and/or "aliphatic" whether used alone or as part of a substituent group refers to straight and branched carbon chains having 1 to 20 carbon atoms or any number within this range, for example 1 to 6 carbon atoms or 1 to 4 carbon atoms. Designated numbers of carbon atoms (e.g. $C_{1-6}$) shall refer independently to the number of carbon atoms in an alkyl moiety or to the alkyl portion of a larger alkyl-containing substituent. Non-limiting examples of alkyl groups include methyl, ethyl, n-propyl, iso-propyl, n-butyl, sec-butyl, iso-butyl, tert-butyl, and the like. Alkyl groups can be optionally substituted. Non-limiting examples of substituted alkyl groups include hydroxymethyl, chloromethyl, trifluoromethyl, aminomethyl, 1-chloroethyl, 2-hydroxyethyl, 1,2-difluoroethyl, 3-carboxypropyl, and the like. In substituent groups with multiple alkyl groups such as $(C_{1-6}alkyl)_2$amino, the alkyl groups may be the same or different.

As used herein, the terms "alkenyl" and "alkynyl" groups, whether used alone or as part of a substituent group, refer to straight and branched carbon chains having 2 or more carbon atoms, preferably 2 to 20, wherein an alkenyl chain has at least one double bond in the chain and an alkynyl chain has at least one triple bond in the chain. Alkenyl and alkynyl groups can be optionally substituted. Nonlimiting examples of alkenyl groups include ethenyl, 3-propenyl, 1-propenyl (also 2-methylethenyl), isopropenyl (also 2-methylethen-2-yl), buten-4-yl, and the like. Nonlimiting examples of substituted alkenyl groups include 2-chloroethenyl (also 2-chlorovinyl), 4-hydroxybuten-1-yl, 7-hydroxy-7-methyloct-4-en-2-yl, 7-hydroxy-7-methyloct-3,5-dien-2-yl, and the like. Nonlimiting examples of alkynyl groups include ethynyl, prop-2-ynyl (also propargyl), propyn-1-yl, and 2-methyl-hex-4-yn-1-yl. Nonlimiting examples of substituted alkynyl groups include, 5-hydroxy-5-methylhex-3-ynyl, 6-hydroxy-6-methylhept-3-yn-2-yl, 5-hydroxy-5-ethylhept-3-ynyl, and the like.

As used herein, "cycloalkyl," whether used alone or as part of another group, refers to a non-aromatic carbon-containing ring including cyclized alkyl, alkenyl, and alkynyl groups, e.g., having from 3 to 14 ring carbon atoms, preferably from 3 to 7 or 3 to 6 ring carbon atoms, or even 3 to 4 ring carbon atoms, and optionally containing one or more (e.g., 1, 2, or 3) double or triple bond. Cycloalkyl groups can be monocyclic (e.g., cyclohexyl) or polycyclic (e.g., containing fused, bridged, and/or spiro ring systems), wherein the carbon atoms are located inside or outside of the ring system. Any suitable ring position of the cycloalkyl group can be covalently linked to the defined chemical structure. Cycloalkyl rings can be optionally substituted. Nonlimiting examples of cycloalkyl groups include: cyclopropyl, 2-methyl-cyclopropyl, cyclopropenyl, cyclobutyl, 2,3-dihydroxycyclobutyl, cyclobutenyl, cyclopentyl, cyclopentenyl, cyclopentadienyl, cyclohexyl, cyclohexenyl, cycloheptyl, cyclooctanyl, decalinyl, 2,5-dimethylcyclopentyl, 3,5-dichlorocyclohexyl, 4-hydroxycyclohexyl, 3,3,5-trimethylcyclohex-1-yl, octahydropentalenyl, octahydro-1H-indenyl, 3a,4,5,6,7,7a-hexahydro-3H-inden-4-yl, decahydroazulenyl; bicyclo[6.2.0]decanyl, decahydronaphthalenyl, and dodecahydro-1H-fluorenyl. The term "cycloalkyl" also includes carbocyclic rings which are bicyclic hydrocarbon rings, non-limiting examples of which include, bicyclo-[2.1.1]hexanyl, bicyclo[2.2.1]heptanyl, bicyclo[3.1.1]heptanyl, 1,3-dimethyl[2.2.1]heptan-2-yl, bicyclo[2.2.2]octanyl, and bicyclo[3.3.3]undecanyl.

"Haloalkyl" is intended to include both branched and straight-chain saturated aliphatic hydrocarbon groups having the specified number of carbon atoms, substituted with 1 or more halogen. Haloalkyl groups include perhaloalkyl groups, wherein all hydrogens of an alkyl group have been replaced with halogens (e.g., —$CF_3$, —$CF_2CF_3$). Haloalkyl groups can optionally be substituted with one or more substituents in addition to halogen. Examples of haloalkyl groups include, but are not limited to, fluoromethyl, dichloroethyl, trifluoromethyl, trichloromethyl, pentafluoroethyl, and pentachloroethyl groups.

The term "alkoxy" refers to the group —O-alkyl, wherein the alkyl group is as defined above. Alkoxy groups optionally may be substituted. The term $C_3$-$C_6$ cyclic alkoxy refers to a ring containing 3 to 6 carbon atoms and at least one oxygen atom (e.g., tetrahydrofuran, tetrahydro-2H-pyran). $C_3$-$C_6$ cyclic alkoxy groups optionally may be substituted.

The term "aryl," wherein used alone or as part of another group, is defined herein as a an unsaturated, aromatic monocyclic ring of 6 carbon members or to an unsaturated, aromatic polycyclic ring of from 10 to 14 carbon members. Aryl rings can be, for example, phenyl or naphthyl ring each optionally substituted with one or more moieties capable of replacing one or more hydrogen atoms. Non-limiting examples of aryl groups include: phenyl, naphthylen-1-yl, naphthylen-2-yl, 4-fluorophenyl, 2-hydroxyphenyl, 3-methylphenyl, 2-amino-4-fluorophenyl, 2-(N,N-diethylamino) phenyl, 2-cyanophenyl, 2,6-di-tert-butylphenyl, 3-methoxyphenyl, 8-hydroxynaphthylen-2-yl 4,5-dimethoxynaphthylen-1-yl, and 6-cyano-naphthylen-1-yl. Aryl groups also include, for example, phenyl or naphthyl rings fused with one or more saturated or partially saturated carbon rings (e.g., bicyclo[4.2.0]octa-1,3,5-trienyl, indanyl), which can be substituted at one or more carbon atoms of the aromatic and/or saturated or partially saturated rings.

The term "arylalkyl" or "aralkyl" refers to the group -alkyl-aryl, where the alkyl and aryl groups are as defined herein. Aralkyl groups of the present invention are optionally substituted. Examples of arylalkyl groups include, for example, benzyl, 1-phenylethyl, 2-phenylethyl, 3-phenylpropyl, 2-phenylpropyl, fluorenylmethyl and the like.

The terms "heterocyclic" and/or "heterocycle" and/or "heterocylyl," whether used alone or as part of another group, are defined herein as one or more ring having from 3 to 20 atoms wherein at least one atom in at least one ring is a heteroatom selected from nitrogen (N), oxygen (O), or sulfur (S), and wherein further that includes the ring that includes the heteroatom is non-aromatic. In heterocycle groups that include 2 or more fused rings, the non-heteroatom bearing ring may be aryl (e.g., indolinyl, tetrahydroquinolinyl, chromanyl). Exemplary heterocycle groups have from 3 to 14 ring atoms of which from 1 to 5 are heteroatoms independently selected from nitrogen (N), oxygen (O), or sulfur (S). One or more N or S atoms in a heterocycle group can be oxidized. Heterocycle groups can be optionally substituted.

Non-limiting examples of heterocyclic units having a single ring include: diazirinyl, aziridinyl, urazolyl, azetidinyl, pyrazolidinyl, imidazolidinyl, oxazolidinyl, isoxazolidinyl, isoxazolyl, thiazolidinyl, isothiazolyl, isothiazolinyl oxathiazolidinonyl, oxazolidinonyl, hydantoinyl, tetrahydrofuranyl, pyrrolidinyl, morpholinyl, piperazinyl, piperidinyl, dihydropyranyl, tetrahydropyranyl, piperidin-2-onyl (valerolactam), 2,3,4,5-tetrahydro-1H-azepinyl, 2,3-dihydro-1H-indole, and 1,2,3,4-tetrahydro-quinoline. Non-limiting examples of heterocyclic units having 2 or more rings include: hexahydro-1H-pyrrolizinyl, 3a,4,5,6,7,7a-hexahydro-1H-benzo[d]imidazolyl, 3a,4,5,6,7,7a-hexahydro-1H-indolyl, 1,2,3,4-tetrahydroquinolinyl, chromanyl, isochromanyl, indolinyl, isoindolinyl, and decahydro-1H-cycloocta[b]pyrrolyl.

The term "heteroaryl," whether used alone or as part of another group, is defined herein as one or more rings having from 5 to 20 atoms wherein at least one atom in at least one ring is a heteroatom chosen from nitrogen (N), oxygen (O), or sulfur (S), and wherein further at least one of the rings that includes a heteroatom is aromatic. In heteroaryl groups that include 2 or more fused rings, the non-heteroatom bearing ring may be a carbocycle (e.g., 6,7-Dihydro-5H-cyclopentapyrimidine) or aryl (e.g., benzofuranyl, benzothiophenyl, indolyl). Exemplary heteroaryl groups have from 5 to 14 ring atoms and contain from 1 to 5 ring heteroatoms independently selected from nitrogen (N), oxygen (O), or sulfur (S). One or more N or S atoms in a heteroaryl group can be oxidized. Heteroaryl groups can be substituted. Non-limiting examples of heteroaryl rings containing a single ring include: 1,2,3,4-tetrazolyl, [1,2,3]triazolyl, [1,2,4]triazolyl, triazinyl, thiazolyl, 1H-imidazolyl, oxazolyl, furanyl, thiopheneyl, pyrimidinyl, 2-phenylpyrimidinyl, pyridinyl, 3-methylpyridinyl, and 4-dimethylaminopyridinyl. Nonlimiting examples of heteroaryl rings containing 2 or more fused rings include: benzofuranyl, benzothiophenyl, benzoxazolyl, benzthiazolyl, benztriazolyl, cinnolinyl, naphthyridinyl, phenanthridinyl, 7H-purinyl, 9H-purinyl, 6-amino-9H-purinyl, 5H-pyrrolo[3,2-d]pyrimidinyl, 7H-pyrrolo[2,3-d]pyrimidinyl, pyrido[2,3-d]pyrimidinyl, 2-phenylbenzo[d]thiazolyl, 1H-indolyl, 4,5,6,7-tetrahydro-1-H-indolyl, quinoxalinyl, 5-methylquinoxalinyl, quinazolinyl, quinolinyl, 8-hydroxy-quinolinyl, and isoquinolinyl.

One non-limiting example of a heteroaryl group as described above is $C_1$-$C_5$ heteroaryl, which has 1 to 5 carbon ring atoms and at least one additional ring atom that is a heteroatom (preferably 1 to 4 additional ring atoms that are heteroatoms) independently selected from nitrogen (N), oxygen (O), or sulfur (S). Examples of $C_1$-$C_5$ heteroaryl include, but are not limited to, triazinyl, thiazol-2-yl, thiazol-4-yl, imidazol-1-yl, 1H-imidazol-2-yl, 1H-imidazol-4-yl, isoxazolin-5-yl, furan-2-yl, furan-3-yl, thiophen-2-yl, thiophen-4-yl, pyrimidin-2-yl, pyrimidin-4-yl, pyrimidin-5-yl, pyridin-2-yl, pyridin-3-yl, and pyridin-4-yl.

Unless otherwise noted, when two substituents are taken together to form a ring having a specified number of ring atoms (e.g., $R^2$ and $R^3$ taken together with the nitrogen (N) to which they are attached to form a ring having from 3 to 7 ring members), the ring can have carbon atoms and optionally one or more (e.g., 1 to 3) additional heteroatoms independently selected from nitrogen (N), oxygen (O), or sulfur (S). The ring can be saturated or partially saturated and can be optionally substituted.

For the purposed of the present invention fused ring units, as well as spirocyclic rings, bicyclic rings and the like, which comprise a single heteroatom will be considered to belong to the cyclic family corresponding to the heteroatom containing ring. For example, 1,2,3,4-tetrahydroquinoline having the formula:

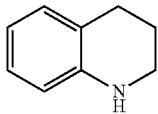

is, for the purposes of the present invention, considered a heterocyclic unit. 6,7-Dihydro-5H-cyclopentapyrimidine having the formula:

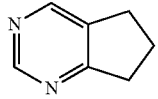

is, for the purposes of the present invention, considered a heteroaryl unit. When a fused ring unit contains heteroatoms in both a saturated and an aryl ring, the aryl ring will predominate and determine the type of category to which the ring is assigned. For example, 1,2,3,4-tetrahydro-[1,8]naphthyridine having the formula:

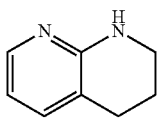

is, for the purposes of the present invention, considered a heteroaryl unit.

Whenever a term or either of their prefix roots appear in a name of a substituent the name is to be interpreted as including those limitations provided herein. For example, whenever the term "alkyl" or "aryl" or either of their prefix roots appear in a name of a substituent (e.g., arylalkyl, alkylamino) the name is to be interpreted as including those limitations given above for "alkyl" and "aryl."

The term "substituted" is used throughout the specification. The term "substituted" is defined herein as a moiety, whether acyclic or cyclic, which has one or more hydrogen atoms replaced by a substituent or several (e.g., 1 to 10) substituents as defined herein below. The substituents are capable of replacing one or two hydrogen atoms of a single moiety at a time. In addition, these substituents can replace two hydrogen atoms on two adjacent carbons to form said substituent, new moiety or unit. For example, a substituted unit that requires a single hydrogen atom replacement includes halogen, hydroxyl, and the like. A two hydrogen atom replacement includes carbonyl, oximino, and the like. A two hydrogen atom replacement from adjacent carbon atoms includes epoxy, and the like. The term "substituted" is used throughout the present specification to indicate that a moiety can have one or more of the hydrogen atoms replaced by a substituent. When a moiety is described as "substituted" any number of the hydrogen atoms may be replaced. For example, difluoromethyl is a substituted $C_1$ alkyl; trifluoromethyl is a substituted $C_1$ alkyl; 4-hydroxyphenyl is a substituted aromatic ring; (N,N-dimethyl-5-amino)octanyl is a substituted $C_8$ alkyl; 3-guanidinopropyl is a substituted $C_3$ alkyl; and 2-carboxypyridinyl is a substituted heteroaryl.

The variable groups defined herein, e.g., alkyl, alkenyl, alkynyl, cycloalkyl, alkoxy, aryloxy, aryl, heterocycle and heteroaryl groups defined herein, whether used alone or as part of another group, can be optionally substituted. Optionally substituted groups will be so indicated.

The following are non-limiting examples of substituents which can substitute for hydrogen atoms on a moiety: halogen (chlorine (Cl), bromine (Br), fluorine (F) and iodine (I)), —CN, —NO$_2$, oxo (=O), —OR$^3$, —SR$^3$, —N(R$^3$)$_2$, —NR$^3$C(O)R$^3$, —SO$_2$R$^3$, —SO$_2$OR$^3$, —SO$_2$N(R$^3$)$_2$, —C(O)R$^3$, —C(O)OR$^3$, —C(O)N(R$^3$)$_2$, $C_{1-6}$ alkyl, $C_{1-6}$ haloalkyl, $C_{1-6}$ alkoxy, $C_{2-8}$ alkenyl, $C_{2-8}$ alkynyl, $C_{3-14}$ cycloalkyl, aryl, heterocycle, or heteroaryl, wherein each of the alkyl, haloalkyl, alkenyl, alkynyl, alkoxy, cycloalkyl, aryl, heterocycle, and heteroaryl groups is optionally substituted with 1-10 (e.g., 1-6 or 1-4) groups selected independently from halogen, —CN, —NO$_2$, oxo, and R$^3$; wherein R$^3$, at each occurrence, independently is hydrogen, —OR$^4$, —SR$^4$, —C(O)R$^4$, —C(O)OR$^4$, —C(O)N(R$^4$)$_2$, —SO$_2$R$^4$, —S(O)$_2$OR$_4$, —N(R$^4$)$_2$, —NR$^4$C(O)R$^4$, $C_{1-6}$ alkyl, $C_{1-6}$ haloalkyl, $C_{2-8}$ alkenyl, $C_{2-8}$ alkynyl, cycloalkyl (e.g., $C_{3-6}$ cycloalkyl), aryl, heterocycle, or heteroaryl, or two R$^x$ units taken together with the atom(s) to which they are bound form an optionally substituted carbocycle or heterocycle wherein said carbocycle or heterocycle has 3 to 7 ring atoms; wherein R$^4$, at each occurrence, independently is hydrogen, $C_{1-6}$ alkyl, $C_{1-6}$ haloalkyl, $C_{2-8}$ alkenyl, $C_{2-8}$ alkynyl, cycloalkyl (e.g., $C_{3-6}$ cycloalkyl), aryl, heterocycle, or heteroaryl, or two R$^4$ units taken together with the atom(s) to which they are bound form an optionally substituted carbocycle or heterocycle wherein said carbocycle or heterocycle preferably has 3 to 7 ring atoms.

In some embodiments, the substituents are selected from
i) —OR$^5$; for example, —OH, —OCH$_3$, —OCH$_2$CH$_3$, —OCH$_2$CH$_2$CH$_3$;
ii) —C(O)R$^5$; for example, —COCH$_3$, —COCH$_2$CH$_3$, —COCH$_2$CH$_2$CH$_3$;
iii) —C(O)OR$^5$; for example, —CO$_2$CH$_3$, —CO$_2$CH$_2$CH$_3$, —CO$_2$CH$_2$CH$_2$CH$_3$;
iv) —C(O)N(R$^5$)$_2$; for example, —CONH$_2$, —CONHCH$_3$, —CON(CH$_3$)$_2$;
v) —N(R$^5$)$_2$; for example, —NH$_2$, —NHCH$_3$, —N(CH$_3$)$_2$, —NH(CH$_2$CH$_3$);
vi) halogen: —F, —Cl, —Br, and —I;
vii) —CH$_e$X$_g$; wherein X is halogen, m is from 0 to 2, e+g=3; for example, —CH$_2$F, —CHF$_2$, —CF$_3$, —CCl$_3$, or —CBr$_3$;
viii) —SO$_2$R$^5$; for example, —SO$_2$H; —SO$_2$CH$_3$; —SO$_2$C$_6$H$_5$;
ix) C$_1$-C$_6$ linear, branched, or cyclic alkyl;
x) Cyano
xi) Nitro;
xii) N(R$^5$)C(O)R$^5$;
xiii) Oxo (=O);
xiv) Heterocycle; and
xv) Heteroaryl.
wherein each R$^5$ is independently hydrogen, optionally substituted C$_1$-C$_6$ linear or branched alkyl (e.g., optionally substituted C$_1$-C$_4$ linear or branched alkyl), or optionally substituted C$_3$-C$_6$ cycloalkyl (e.g optionally substituted C$_3$-C$_4$ cycloalkyl); or two R$^5$ units can be taken together to form a ring comprising 3-7 ring atoms. In certain aspects, each R$^5$ is independently hydrogen, C$_1$-C$_6$ linear or branched alkyl optionally substituted with halogen or C$_3$-C$_6$ cycloalkyl or C$_3$-C$_6$ cycloalkyl.

At various places in the present specification, substituents of compounds are disclosed in groups or in ranges. It is specifically intended that the description include each and every individual subcombination of the members of such groups and ranges. For example, the term "C$_{1-6}$ alkyl" is specifically intended to individually disclose C$_1$, C$_2$, C$_3$, C$_4$, C$_5$, C$_6$, C$_1$-C$_6$, C$_1$-C$_5$, C$_1$-C$_4$, C$_1$-C$_3$, C$_1$-C$_2$, C$_2$-C$_6$, C$_2$-C$_5$, C$_2$-C$_4$, C$_2$-C$_3$, C$_3$-C$_6$, C$_3$-C$_5$, C$_3$-C$_4$, C$_4$-C$_6$, C$_4$-C$_5$, and C$_5$-C$_6$, alkyl.

For the purposes of the present invention the terms "compound," "analog," and "composition of matter" stand equally well for the substituted aminothiazoles described herein, including all enantiomeric forms, diastereomeric forms, salts, and the like, and the terms "compound," "analog," and "composition of matter" are used interchangeably throughout the present specification.

Compounds described herein can contain an asymmetric atom (also referred as a chiral center), and some of the compounds can contain one or more asymmetric atoms or centers, which can thus give rise to optical isomers (enantiomers) and diastereomers. The present teachings and compounds disclosed herein include such enantiomers and diastereomers, as well as the racemic and resolved, enantiomerically pure R and S stereoisomers, as well as other mixtures of the R and S stereoisomers and pharmaceutically acceptable salts thereof. Optical isomers can be obtained in pure form by standard procedures known to those skilled in the art, which include, but are not limited to, diastereomeric salt formation, kinetic resolution, and asymmetric synthesis. The present teachings also encompass cis and trans isomers of compounds containing alkenyl moieties (e.g., alkenes and imines). It is also understood that the present teachings encompass all possible regioisomers, and mixtures thereof, which can be obtained in pure form by standard separation procedures known to those skilled in the art, and include, but are not limited to, column chromatography, thin-layer chromatography, and high-performance liquid chromatography.

Pharmaceutically acceptable salts of compounds of the present teachings, which can have an acidic moiety, can be formed using organic and inorganic bases. Both mono and polyanionic salts are contemplated, depending on the number of acidic hydrogens available for deprotonation. Suitable salts formed with bases include metal salts, such as alkali metal or alkaline earth metal salts, for example sodium, potassium, or magnesium salts; ammonia salts and organic amine salts, such as those formed with morpholine, thiomorpholine, piperidine, pyrrolidine, a mono-, di- or tri-lower alkylamine (e.g., ethyl-tert-butyl-, diethyl-, diisopropyl-, triethyl-, tributyl- or dimethylpropylamine), or a mono-, di-, or trihydroxy lower alkylamine (e.g., mono-, di- or triethanolamine). Specific non-limiting examples of inorganic bases include NaHCO$_3$, Na$_2$CO$_3$, KHCO$_3$, K$_2$CO$_3$, Cs$_2$CO$_3$, LiOH, NaOH, KOH, NaH$_2$PO$_4$, Na$_2$HPO$_4$, and Na$_3$PO$_4$. Internal salts also can be formed. Similarly, when a compound disclosed herein contains a basic moiety, salts can be formed using organic and inorganic acids. For example, salts can be formed from the following acids: acetic, propionic, lactic, benzenesulfonic, benzoic, camphorsulfonic, citric, tartaric, succinic, dichloroacetic, ethenesulfonic, formic, fumaric, gluconic, glutamic, hippuric, hydrobromic, hydrochloric, isethionic, lactic, maleic, malic, malonic, mandelic, methanesulfonic, mucic, napthalenesulfonic, nitric, oxalic, pamoic, pantothenic, phosphoric, phthalic, propionic, succinic, sulfuric, tartaric, toluenesulfonic, and camphorsulfonic as well as other known pharmaceutically acceptable acids.

When any variable occurs more than one time in any constituent or in any formula, its definition in each occurrence is independent of its definition at every other occurrence (e.g., in N(R$^4$)$_2$, each R$^4$ may be the same or different than the other). Combinations of substituents and/or variables are permissible only if such combinations result in stable compounds.

The terms "treat" and "treating" and "treatment" as used herein, refer to partially or completely alleviating, inhibiting, ameliorating and/or relieving a condition from which a patient is suspected to suffer.

As used herein, "therapeutically effective" and "effective dose" refer to a substance or an amount that elicits a desirable biological activity or effect.

Except when noted, the terms "subject" or "patient" are used interchangeably and refer to mammals such as human patients and non-human primates, as well as experimental animals such as rabbits, rats, and mice, and other animals. Accordingly, the term "subject" or "patient" as used herein means any mammalian patient or subject to which the compounds of the invention can be administered. In an exemplary embodiment of the present invention, to identify subject patients for treatment according to the methods of the invention, accepted screening methods are employed to determine risk factors associated with a targeted or suspected disease or condition or to determine the status of an existing disease or condition in a subject. These screening methods include, for example, conventional work-ups to determine risk factors that may be associated with the targeted or suspected disease or condition. These and other routine methods allow the clinician to select patients in need of therapy using the methods and compounds of the present invention.

The Substituted Aminothiazoles

The compounds of the present invention are substituted aminothiazoles, and include all enantiomeric and diastereomeric forms and pharmaceutically accepted salts thereof having the formula:

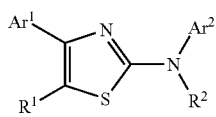
(I)

Including hydrates, solvates, pharmaceutically acceptable salts, prodrugs and complexes thereof, wherein:

$R^1$ is selected from a group consisting of hydrogen, $C_1$-$C_9$ linear alkyl, isopropyl, cyclohexyl, bromine, cyano,

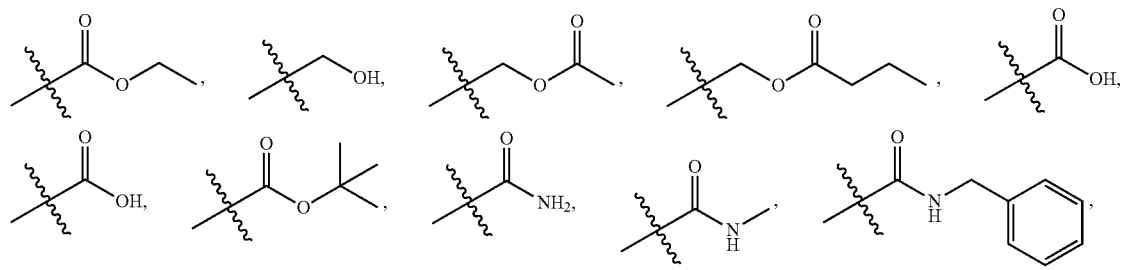

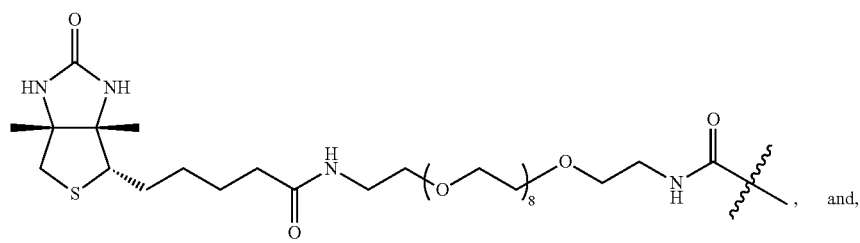

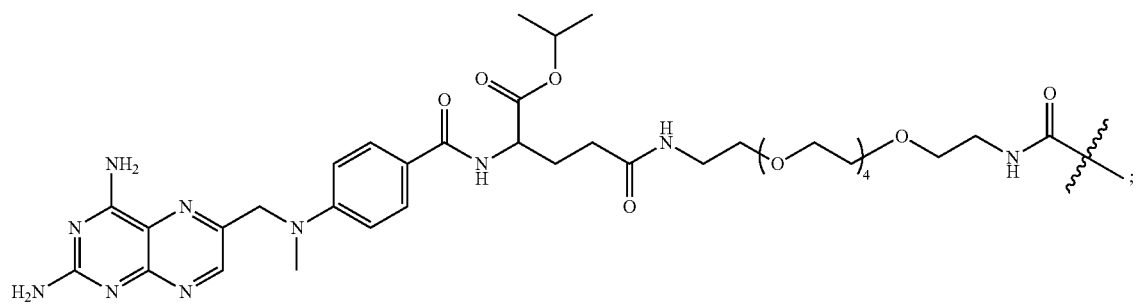

$R^2$ is selected from a group consisting of hydrogen, methyl, isopropyl, tert-butyl, benzyl, and

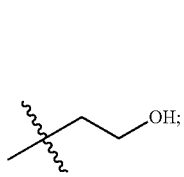 [SMILES: *CCO]

$Ar^1$ is selected from a group consisting of phenyl,

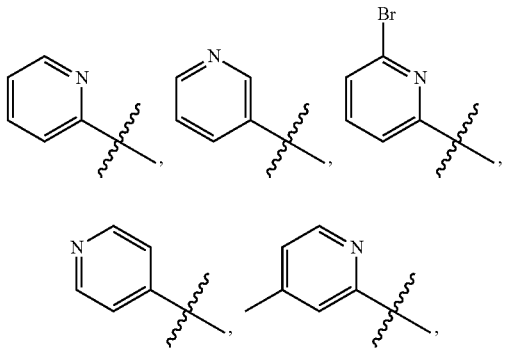

-continued

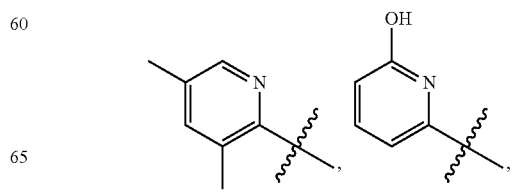

-continued
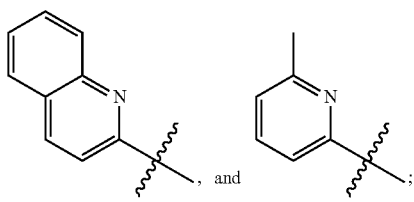, and
Ar² is selected from a group consisting of phenyl,
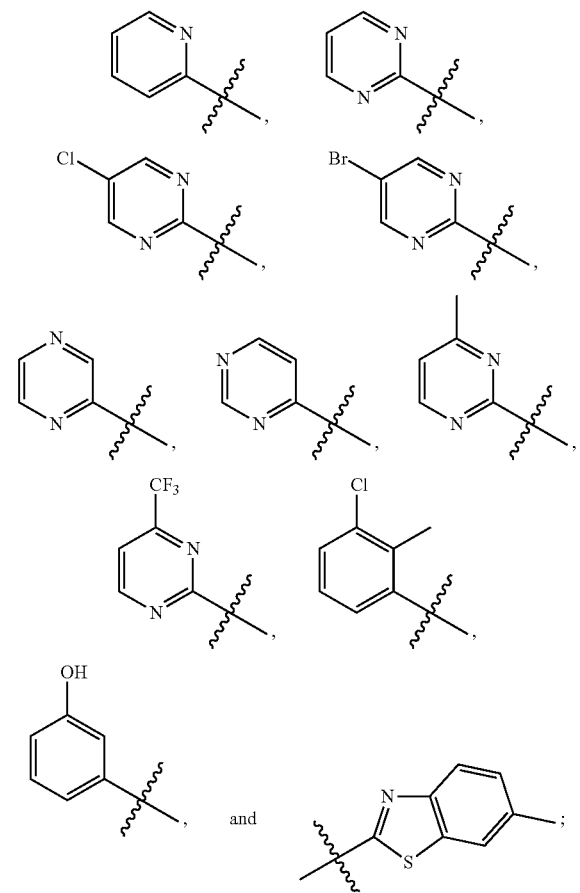
, and 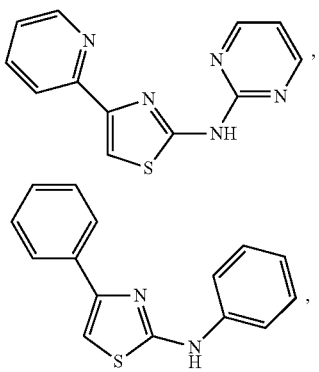 ;
Compounds of the structures
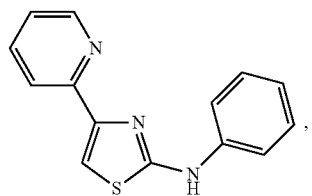,
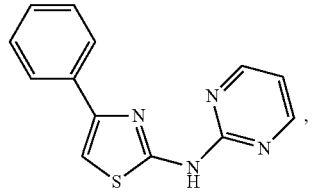,
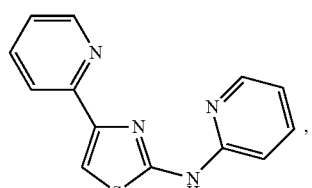,
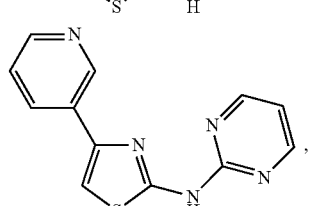,
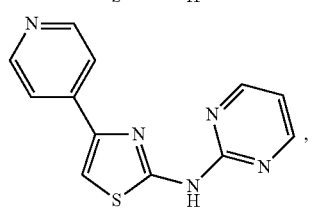,
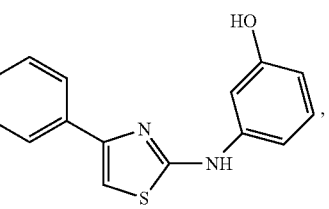,
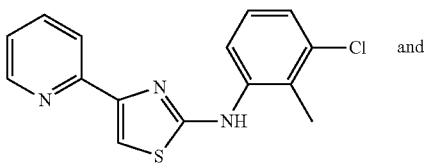 and
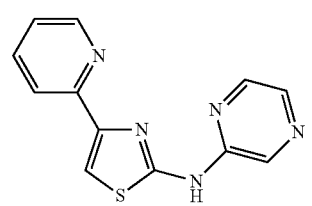
are excluded from the novel compounds of formula (I).
The present invention is also directed toward novel methods of use of compounds of the structure

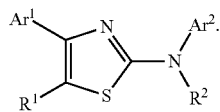

(I)

In some embodiments, $R^1$ is hydrogen.
In some embodiments, $R^1$ is $C_1$-$C_9$ linear alkyl
In some embodiments, $R^1$ is methyl.
In some embodiments, $R^1$ is ethyl.
In some embodiments, $R^1$ is pentyl.
In some embodiments, $R^1$ is nonyl.
In some embodiments, $R^1$ is isopropyl.
In some embodiments, $R^1$ is cyclohexyl.
In some embodiments, $R^1$ is bromine.
In some embodiments, $R^1$ is cyano.
In some embodiments, $R^1$ is

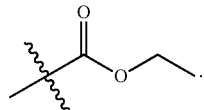 [SMILES: *C(=O)OCC]

In some embodiments, $R^1$ is

In some embodiments, $R^1$ is

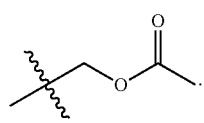 [SMILES: *COC(C)=O]

In some embodiments, $R^1$ is

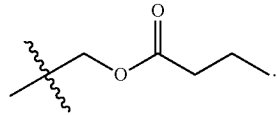 [SMILES: *COC(=O)CCC]

In some embodiments, $R^1$ is

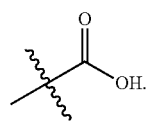

In some embodiments, $R^1$ is

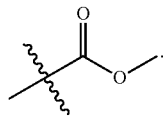 [SMILES: *C(=O)OC]

In some embodiments, $R^1$ is

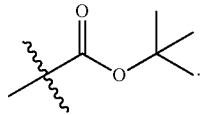 [SMILES: *C(=O)OC(C)(C)C]

In some embodiments, $R^1$ is

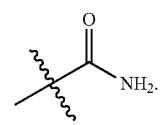 [SMILES: *C(N)=O]

In some embodiments, $R^1$ is

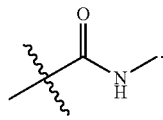 [SMILES: *C(=O)NC]

In some embodiments, $R^1$ is

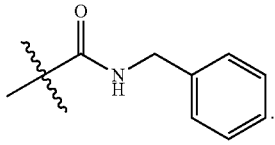 [SMILES: *C(=O)NCc1ccccc1]

In some embodiments, $R^1$ is

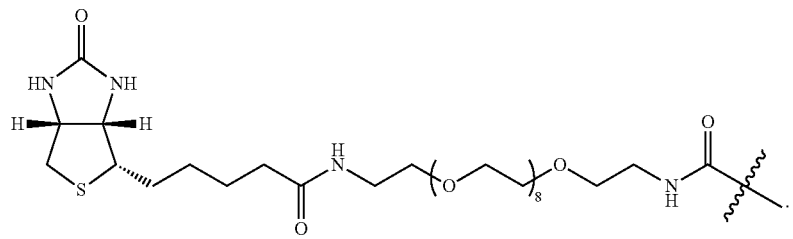

In some embodiments, R¹ is

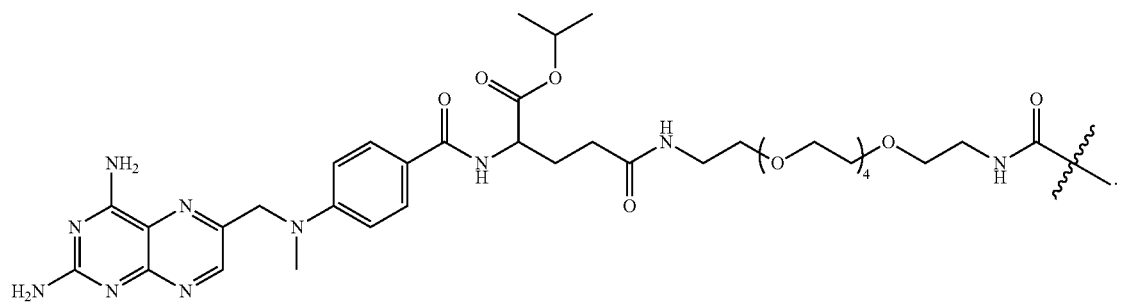

In some embodiments, R² is hydrogen.
In some embodiments, R² is methyl.
In some embodiments, R² is isopropyl.
In some embodiments, R² is tert-butyl
In some embodiments, R² is benzyl.
In some embodiments, R² is

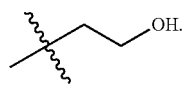 [SMILES: *CCO]

In some embodiments, Ar¹ is phenyl.
In some embodiments, Ar¹ is

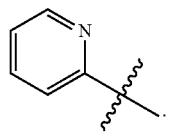 [SMILES: *c1ccccn1]

In some embodiments, Ar¹ is

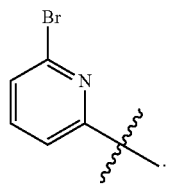 [SMILES: *c1cccc(Br)n1]

In some embodiments, Ar¹ is

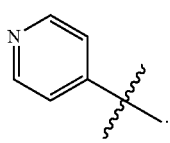 [SMILES: *c1ccncc1]

In some embodiments, Ar¹ is

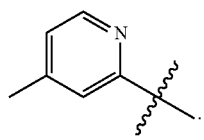

In some embodiments, Ar¹ is

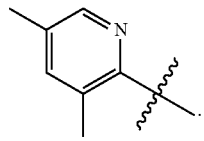 [SMILES: *c1ncc(C)cc1C]

In some embodiments, Ar¹ is

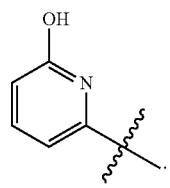 [SMILES: *c1cccc(O)n1]

In some embodiments, Ar¹ is

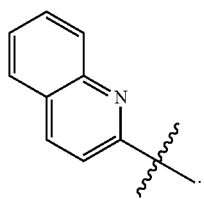 [SMILES: *c1ccc2ccccc2n1]

In some embodiments, Ar¹ is

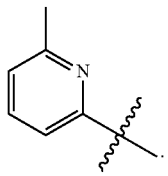 [SMILES: *c1cccc(C)n1]

In some embodiments, Ar² is phenyl.
In some embodiments, Ar² is

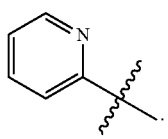 [SMILES: *c1ccccn1]

In some embodiments, Ar² is

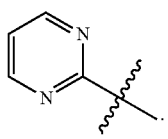

In some embodiments, Ar² is

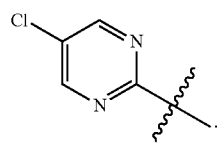

In some embodiments, Ar² is

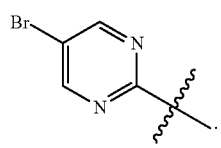

In some embodiments, Ar² is

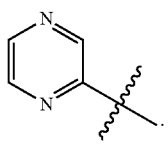 [SMILES: *c1cnccn1]

In some embodiments, Ar² is

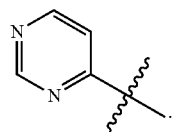 [SMILES: *c1ccncn1]

In some embodiments, Ar² is

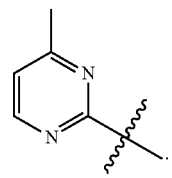 [SMILES: *c1nccc(C)n1]

In some embodiments, Ar² is

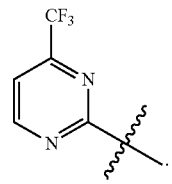 [SMILES: *c1nccc(C(F)(F)F)n1]

In some embodiments, Ar² is

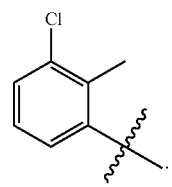 [SMILES: *c1cccc(Cl)c1C]

In some embodiments, Ar² is

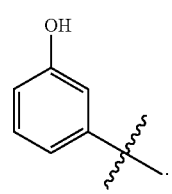 [SMILES: *c1cccc(O)c1]

In some embodiments, Ar² is

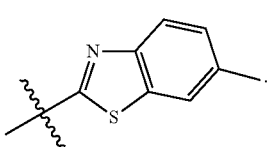 [SMILES: *c1nc2ccc(C)cc2s1]

Exemplary embodiments include compounds having the formula (I) or a pharmaceutically acceptable salt form thereof:

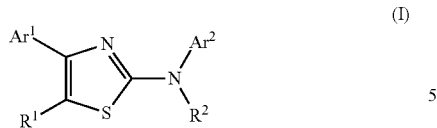
(I)
wherein non-limiting examples of $R^1$, $R^2$, $Ar^1$ and $Ar^2$ are defined herein below in Table 1.
TABLE 1
Exemplary embodiments of compounds of the formula (I):
| Entry | $R^1$ | $R^2$ | $Ar^1$ | $Ar^2$ |
|---|---|---|---|---|
| 1 | H | H | 2-pyridyl | 2-pyridyl |
| 2 | H | H | Phenyl | Phenyl |
| 3 | H | H | Phenyl | 2-pyrimidyl |
| 4 | H | H | Phenyl | 3-hydroxyphenyl |
| 5 | H | H | 2-pyridyl | 2-chloro-3-methylphenyl |
| 6 | H | H | 2-pyridyl | 2-pyridyl |
| 7 | H | H | 2-pyridyl | 2-pyrimidyl |
| 8 | H | H | 3-pyridyl | 2-pyrimidyl |

TABLE 1-continued
Exemplary embodiments of compounds of the formula (I):
| Entry | R¹ | R² | Ar¹ | Ar² |
|---|---|---|---|---|
| 9 | H | H | 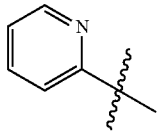 [SMILES: *c1ccccn1] | 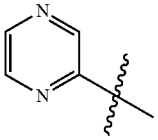 |
| 10 | H | H | 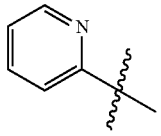 [SMILES: *c1ccccn1] | 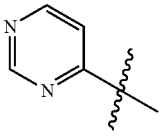 [SMILES: *c1ccncn1] |
| 11 | H | H | 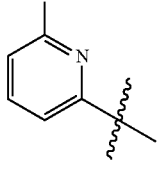 | 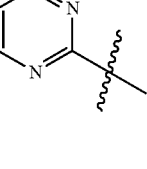 |
| 12 | H | H | 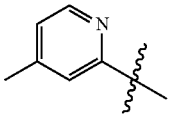 [SMILES: *c1cc(C)ccn1] | 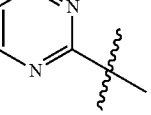 |
| 13 | H | H | 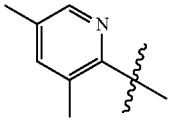 [SMILES: *c1ncc(C)cc1C] | 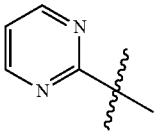 |
| 14 | H | H | 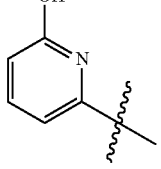 | 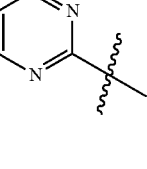 |
| 15 | H | H | 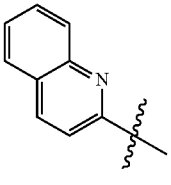 [SMILES: *c1ccc2ccccc2n1] | 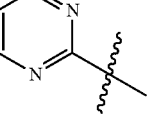 |
| 16 | H | H | 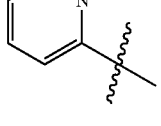 | 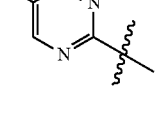 |
| 17 | H | H | 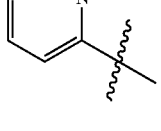 | 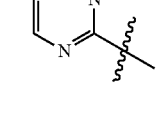 |

TABLE 1-continued
Exemplary embodiments of compounds of the formula (I):
| Entry | R¹ | R² | Ar¹ | Ar² |
|---|---|---|---|---|
| 18 | H | H | 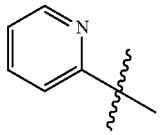 [SMILES: *c1ccccn1] | 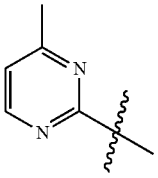 [SMILES: *c1nccc(C)n1] |
| 19 | H | H | 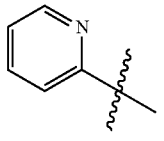 [SMILES: *c1ccccn1] | 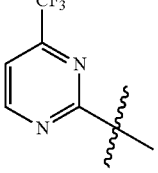 |
| 20 | H | H | 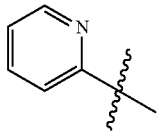 [SMILES: *c1ccccn1] | 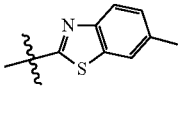 [SMILES: *c1nc2ccc(C)cc2s1] |
| 21 | CH₃ | H | 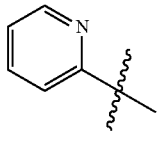 [SMILES: *c1ccccn1] | 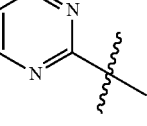 |
| 22 | CH₂CH₃ | H | 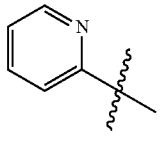 [SMILES: *c1ccccn1] | 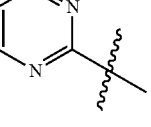 |
| 23 | CH(CH₃)₂ | H | 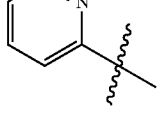 | 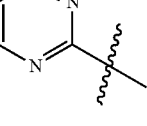 |
| 24 | CH₂(CH₃)₃CH₃ | H | 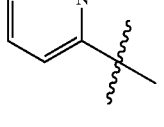 | 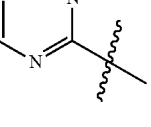 |
| 25 | Cyclohexyl | H | 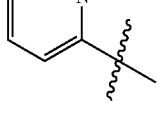 | 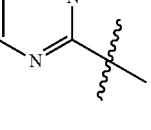 |
| 26 | Nonyl | H | 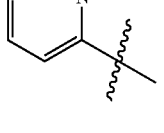 | 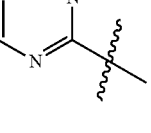 |

TABLE 1-continued
Exemplary embodiments of compounds of the formula (I):
| Entry | R¹ | R² | Ar¹ | Ar² |
|---|---|---|---|---|
| 27 | Cyano | H | 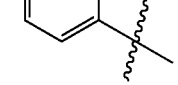 | 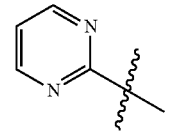 |
| 28 | H | Isopropyl | 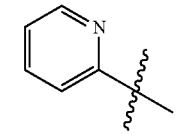 [SMILES: *c1ccccn1] | 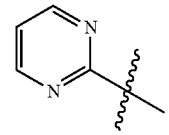 |
| 29 | H | Methyl | 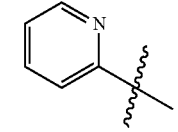 [SMILES: *c1ccccn1] | 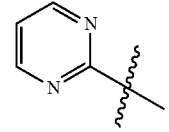 |
| 30 | H | Benzyl | 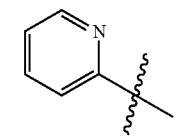 [SMILES: *c1ccccn1] | 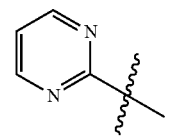 |
| 31 | H | 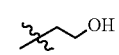 | 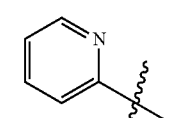 | 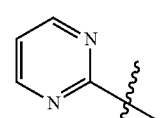 |
| 32 | Br | H | 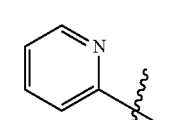 | 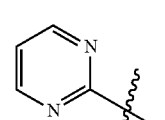 |
| 33 |  | H | 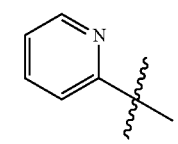 [SMILES: *c1ccccn1] | 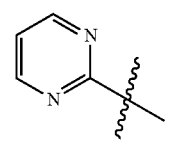 |
| 34 | 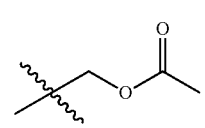 [SMILES: *COC(C)=O] | H | 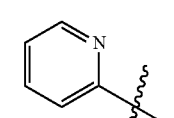 | 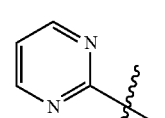 |
| 35 | 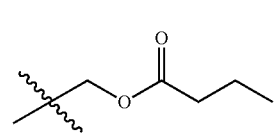 [SMILES: *COC(=O)CCC] | H | 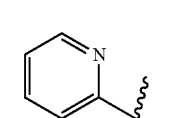 | 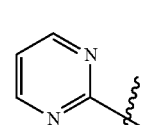 |
| 36 | 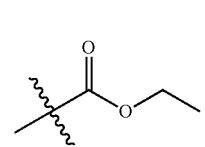 [SMILES: *C(=O)OCC] | H | 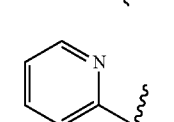 | 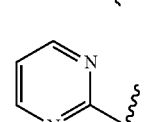 |

TABLE 1-continued

Exemplary embodiments of compounds of the formula (I):

| Entry | R¹ | R² | Ar¹ | Ar² |
|---|---|---|---|---|
| 37 | ethyl ester (CH(CH₃)C(O)OEt) | H | 4-methylpyridin-2-yl | pyrimidin-2-yl |
| 38 | ethyl ester (CH(CH₃)C(O)OEt) | H | 6-methylpyridin-2-yl | pyrimidin-2-yl |
| 39 | ethyl ester (CH(CH₃)C(O)OEt) | H | pyridin-2-yl | 4-methylpyrimidin-2-yl |
| 40 | CO₂H | H | pyridin-2-yl | pyrimidin-2-yl |
| 41 | methyl ester (CH(CH₃)C(O)OMe) | H | pyridin-2-yl | pyrimidin-2-yl |
| 42 | tert-butyl ester (CH(CH₃)C(O)OtBu) | tBu | pyridin-2-yl | pyrimidin-2-yl |
| 43 | CH(CH₃)C(O)NH₂ | H | pyridin-2-yl | pyrimidin-2-yl |
| 44 | CH(CH₃)C(O)NHMe | H | pyridin-2-yl | pyrimidin-2-yl |
| 45 | CH(CH₃)C(O)NHCH₂Ph | H | pyridin-2-yl | pyrimidin-2-yl |

TABLE 1-continued

Exemplary embodiments of compounds of the formula (I):

| Entry | R¹ | R² | Ar¹ | Ar² |
|---|---|---|---|---|
| 46 | (structure) | H | (pyridin-2-yl) | (pyrimidin-2-yl) |
| 47 | (structure) | H | (pyridin-2-yl) | (pyrimidin-2-yl) |

For the purposes of demonstrating the manner in which the compounds of the present invention are named and referred to herein, the compound having the formula:

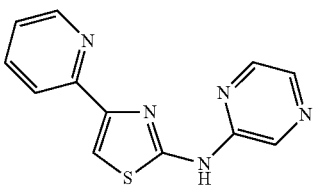 [SMILES: c1ccc(-c2csc(Nc3cnccn3)n2)nc1]

has the chemical name N-(pyrazin-2-yl)-4-(pyridin-2-yl) thiazol-2-amine.

For the purposes of demonstrating the manner in which the compounds of the present invention are named and referred to herein, the compound having the formula:

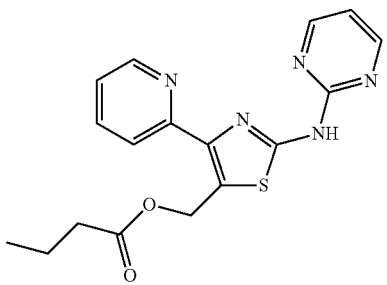 [SMILES: CCCC(=O)OCc1sc(Nc2ncccn2)nc1-c1ccccn1]

has the chemical name (4-(pyridin-2-yl)-2-(pyrimidin-2-ylamino)thiazol-5-yl)methyl butyrate.

For the purposes of the present invention, a compound depicted by the racemic formula, will stand equally well for either of the two enantiomers or mixtures thereof, or in the case where a second chiral center is present, all diastereomers.

In all of the embodiments provided herein, examples of suitable optional substituents are not intended to limit the scope of the claimed invention. The compounds of the invention may contain any of the substituents, or combinations of substituents, provided herein.

Process

The present invention further relates to a process for preparing the compounds of the present invention. Compounds of the present teachings can be prepared in accordance with the procedures outlined herein, from commercially available starting materials, compounds known in the literature, or readily prepared intermediates, by employing standard synthetic methods and procedures known to those skilled in the art of organic chemistry. Standard synthetic methods and procedures for the preparation of organic molecules and functional group transformations and manipulations can be readily obtained from the relevant scientific literature or from standard textbooks in the field. It will be appreciated that where typical or preferred process conditions (i.e., reaction temperatures, times, mole ratios of reactants, solvents, pressures, etc.) are given, other process conditions can also be used unless otherwise stated. Optimum reaction conditions can vary with the particular reactants or solvent used, but such conditions can be determined by one skilled in the art by routine optimization procedures. Those skilled in the art of organic synthesis will recognize that the nature and order of the synthetic steps presented can be varied for the purpose of optimizing the formation of the compounds described herein.

The processes described herein can be monitored according to any suitable method known in the art. For example, product formation can be monitored by spectroscopic means, such as nuclear magnetic resonance spectroscopy (e.g., $^1H$ or $^{13}C$), infrared spectroscopy, spectrophotometry (e.g., UV-visible), mass spectrometry, or by chromatography such as high pressure liquid chromatography (HPLC), gas chromatography (GC), gel-permeation chromatography (GPC), or thin layer chromatography (TLC).

Preparation of the compounds can involve protection and deprotection of various chemical groups. The need for protection and deprotection and the selection of appropriate protecting groups can be readily determined by one skilled in the art. The chemistry of protecting groups can be found, for example, in Greene et al., *Protective Groups in Organic Synthesis,* 2d. Ed. (Wiley & Sons, 1991), the entire disclosure of which is incorporated by reference herein for all purposes.

The reactions or the processes described herein can be carried out in suitable solvents which can be readily selected by one skilled in the art of organic synthesis. Suitable solvents typically are substantially nonreactive with the reactants, intermediates, and/or products at the temperatures at which the reactions are carried out, i.e., temperatures that can range from the solvent's freezing temperature to the solvent's boiling temperature. A given reaction can be carried out in one solvent or a mixture of more than one solvent. Depending on the particular reaction step, suitable solvents for a particular reaction step can be selected.

The Examples provided below provide representative methods for preparing exemplary compounds of the present invention. The skilled practitioner will know how to substitute the appropriate reagents, starting materials and purification methods known to those skilled in the art, in order to prepare the compounds of the present invention.

$^1$H NMR spectra were recorded on a 300 MHz INOVA VARIAN spectrometer. Chemical shifts values are given in ppm and referred as the internal standard to TMS (tetramethylsilane). The peak patterns are indicated as follows: s, singlet; d, doublet; t, triplet; q, quadruplet; m, multiplet and dd, doublet of doublets. The coupling constants (J) are reported in Hertz (Hz). Mass Spectra were obtained on a 1200 Aligent LC-MS spectrometer (ES-API, Positive). Silica gel column chromatography was performed over silica gel 100-200 mesh using the solvent systems described herein.

The examples provide methods for preparing representative compounds of formula (I). The skilled practitioner will know how to substitute the appropriate reagents, starting materials and purification methods known to those skilled in the art, in order to prepare additional compounds of the present invention.

Example 1: Synthesis of 1-(pyrimidin-2-yl)thiourea

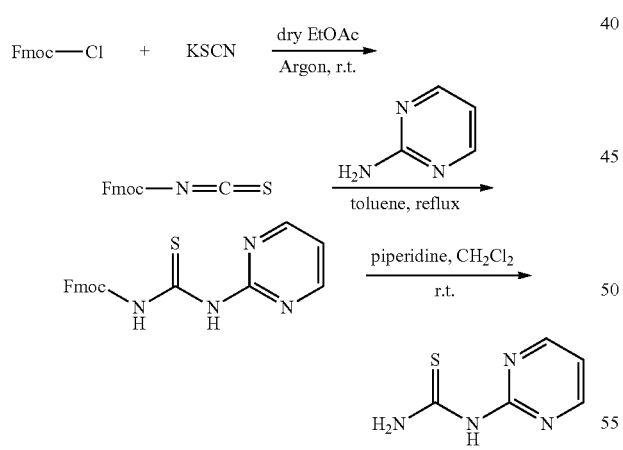

To a suspension of potassium thiocyanate (3.31 g, 34.0 mmol) in anhydrous ethyl acetate (30 mL) at 0° C. under the argon atmosphere, was added dropwise a solution of fluorenylmethyloxy-carbonyl chloride (8.00 g, 30.9 mmol) in anhydrous ethyl acetate (30 mL). After addition, the reaction mixture was stirred at room temperature for 24 hours. Then, it was concentrated and purified through silica gel column chromatography (dichloromethane:hexanes=40:60) to afford 5.00 g of pure product O-((9H-fluoren-9-yl)methyl) carbonisothiocyanatidate as colorless oil.

A reaction mixture of O-((9H-fluoren-9-yl)methyl) carbonisothiocyanatidate (5.00 g, 17.8 mmol) and pyrimidin-2-amine (1.61 g, 16.9 mmol) in toluene (80 mL) was refluxed for 4 hours. Then, it was filtered and washed with toluene to give 6.00 g of product 1-Fmoc-3-(pyrimidin-2-yl)thiourea as white solid, which was directly used in the next step without further purification.

To a stirred suspension of 1-Fmoc-3-(pyrimidin-2-yl) thiourea (6.00 g, 15.9 mmol) in dichloromethane (120 mL), was added piperidine (24 mL). The reaction mixture was stirred at room temperature for 20 hours, and then filtered and washed with dichloromethane. The crude product was slurried in water (50 mL) for 10 minutes, filtered, washed with water and dried under the vacuum to afforded 2.35 g of pure product 1-(pyrimidin-2-yl)thiourea as white solid. $^1$H NMR (300 MHz, DMSO-d$_6$): δ 10.57 (s, 1H, NH), 10.20 (s, 1H, NH), 9.13 (s, 1H, NH), 8.63 (d, J=4.8 Hz, 2H, CH$_{ar}$), 7.14 (t, J=5.1 Hz, 1H, CH$_{ar}$).

Example 2: Synthesis of 1-(pyrazin-2-yl)thiourea

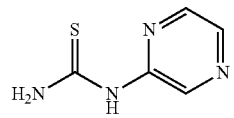

1-(pyrazin-2-yl)thiourea was synthesized from pyrazin-2-ylamine in the same manner as Example 1 to provide the product as a white solid. $^1$H NMR (300 MHz, DMSO-d$_6$): δ 10.83 (s, 1H, NH), 9.94 (s, 1H, NH), 9.08 (s, 1H, NH), 8.52 (s, 1H, CH$_{ar}$), 8.23 (s, 2H, CH$_{ar}$).

Example 3: Synthesis of 1-(pyrimidin-4-yl)thiourea

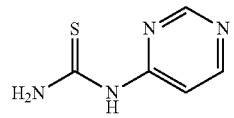

1-(pyrimidin-4-yl)thiourea was synthesized from pyrimidin-4-ylamine in the same manner as Example 1 to provide the product as a white solid. $^1$H NMR (300 MHz, DMSO-d$_6$): δ 10.83 (s, 1H, NH), 10.28 (s, 1H, NH), 9.29 (s, 1H, NH), 8.78 (d, J=0.6 Hz, 1H, CH$_{ar}$), 8.54 (d, J=6.0 Hz, 1H, CH$_{ar}$), 7.14 (dd, J=5.7, 1.2 Hz, 1H, CH$_{ar}$).

Example 4: Synthesis of 1-(5-chloropyrimidin-2-yl)thiourea

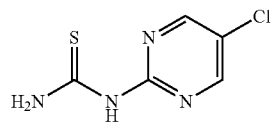 [SMILES: NC(=S)Nc1ncc(Br)cn1]

1-(5-chloropyrimidin-2-yl)thiourea was synthesized from 5-chloro-pyrimidin-2-ylamine in the same manner as Example 1 to provide the product as a white solid. $^1$H NMR (300 MHz, DMSO-d$_6$): δ 10.88 (s, 1H, NH), 9.90 (s, 1H, NH), 9.20 (s, 1H, NH), 8.72 (s, 2H, CH$_{ar}$).

Example 5: Synthesis of 1-(5-bromopyrimidin-2-yl)thiourea

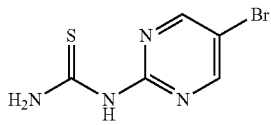

1-(5-bromopyrimidin-2-yl)thiourea was synthesized from 5-bromo-pyrimidin-2-ylamine in the same manner as Example 1 to provide the product as a white solid. $^1$H NMR (300 MHz, DMSO-$d_6$): δ 10.85 (s, 1H, NH), 9.89 (s, 1H, NH), 9.21 (s, 1H, NH), 8.77 (s, 2H, CH$_{ar}$).

Example 6: Synthesis of 1-(4-(trifluoromethyl)pyrimidin-2-yl)thiourea

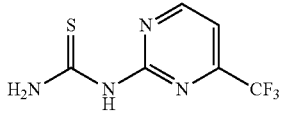

1-(4-(trifluoromethyl)pyrimidin-2-yl)thiourea was synthesized from 4-trifluoromethyl-pyrimidin-2-ylamine in the same manner as Example 1 to provide the product. $^1$H NMR (300 MHz, DMSO-$d_6$): δ 9.85 (s, 1H, NH), 9.33 (s, 1H, NH), 8.97 (d, J=5.1 Hz, 1H, CH$_{ar}$), 7.61 (d, J=4.8 Hz, 1H, CH$_{ar}$).

Example 7: Synthesis of 1-(4-methylpyrimidin-2-yl)thiourea

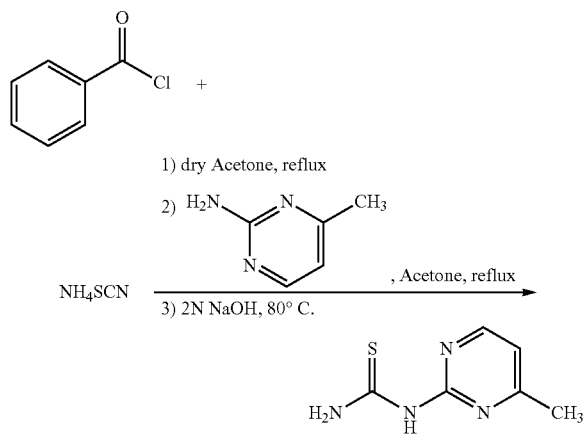

Benzoyl chloride (1.74 mL, 15 mmol) was added dropwise to a solution of ammonium thiocyanate (1.90 g, 25 mmol) in dry acetone (20 mL) at room temperature. It was heated to reflux for 15 minutes, and then treated with 4-methylpyrimidin-2-amine (1.09 g, 10 mmol). Refluxing was continued for 30 minutes. After cooling down, the reaction mixture was poured onto ice and stirred for 30 minutes. The precipitate was collected by filtration, washed with water, and then hydrolyzed in 2N sodium hydroxide (30 mL) at 80° C. for 30 minutes. It was cooled to room temperature and poured into ice-cold 6 M HCl (20 mL). The pH was adjusted to 8-9 with powder sodium carbonate. The crude product was collected by filtration and washed with water. It was further slurried in dichloromethane and filtered to give 340 mg of compound 1-(4-methylpyrimidin-2-yl)thiourea as white solid. $^1$H NMR (300 MHz, DMSO-$d_6$): δ 10.39 (s, 1H, NH), 10.27 (s, 1H, NH), 9.09 (s, 1H, NH), 8.46 (d, J=5.1 Hz, 1H, CH$_{ar}$), 7.03 (d, J=5.1 Hz, 1H, CH$_{ar}$), 2.40 (s, 3H, ArCH$_3$).

Example 7: Synthesis of 1-(6-methylbenzo[d]thiazol-2-yl)thiourea

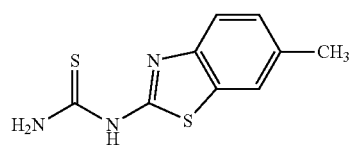

Synthesis of 1-(6-methylbenzo[d]thiazol-2-yl)thiourea was synthesized from 6-methyl-benzothiazol-2-ylamine in the same manner as Example 7 to provide the product white solid. $^1$H NMR (300 MHz, DMSO-$d_6$): δ 11.73 (s, 1H, NH), 9.06 (s, 2H, NH$_2$), 7.69 (s, 1H, CH$_{ar}$), 7.56 (d, J=7.8 Hz, 1H, CH$_{ar}$), 7.20 (d, J=7.5 Hz, 1H, CH$_{ar}$), 2.37 (s, 3H, ArCH$_3$).

Example 8: Synthesis of 1-(pyrimidin-2-yl)thiourea

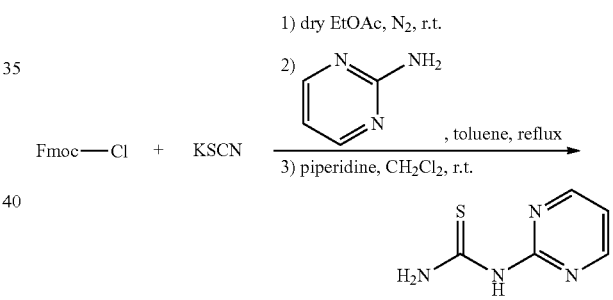

To a suspension of potassium thiocyanate (4.28 g, 44.0 mmol) in anhydrous ethyl acetate (EtOAc, 50 mL) at 0° C. under the argon atmosphere, was added dropwise a solution of fluorenylmethyloxy-carbonyl chloride (Fmoc-Cl, 10.35 g, 40.0 mmol) in anhydrous ethyl acetate (50 mL). After addition, the reaction mixture was stirred at room temperature for 24 hours. The reaction mixture was diluted with hexanes (100 mL), then filtered through a silica gel pad and washed with a mixture of dichloromethane and hexanes (25:75, 200 mL). The filtrate was concentrated to give the crude O-((9H-fluoren-9-yl)methyl) carbonisothiocyanatidate as light-yellow oil, which was dissolved in toluene (100 mL), followed by addition of pyrimidin-2-amine (3.62 g, 38.0 mmol). It was refluxed for 4 hours, filtered and washed with toluene (100 mL) to afford 1-Fmoc-3-(pyrimidin-2-yl)thiourea, which was suspended in dichloromethane (100 mL) and treated with piperidine (24 mL). After stirred at room temperature for 12 hours, the mixture was filtered and washed with dichloromethane (100 mL) then water (100 mL). The solid was dried under the vacuum to afforded 4.45 g of pure product 1-(pyrimidin-2-yl)thiourea as light-brown solid.

Example 8: Synthesis of 1-(pyridin-2-yl)propan-1-one

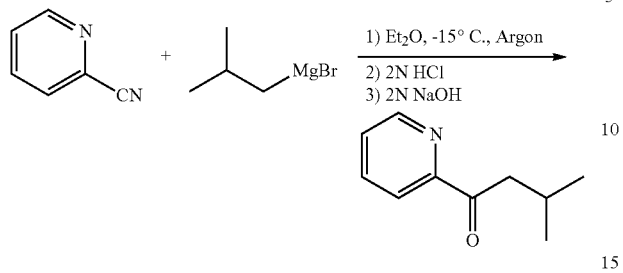

To a stirred solution of 2-cyanopyridine (1.04 g, 10 mmol) in anhydrous diethyl ether (20 mL) at <−15° C. under argon atmosphere, was added slowly isobutylmagnesium bromide (2M in diethyl ether, 6.0 mL, 12 mmol). After addition, the reaction mixture was stirred at this temperature for 1 hour, and then allowed to warm up to room temperature over 3 hours. It was quenched with 2N HCl (6 mL) at 0° C. and stirred for another 15 minutes. The pH was adjusted to 8-9 with 2N NaOH. The mixture was diluted with water (15 mL) and extracted with ethyl acetate (30 mL×3). The combined organic layer was dried over $Na_2SO_4$, concentrated and purified through silica gel column chromatography (ethyl acetate:hexanes=4:96 to 16:84) to afford 1.40 g product 1-(pyridin-2-yl)propan-1-one as colorless oil. $^1$H NMR (300 MHz, CDCl$_3$): δ 8.68 (dt, J=4.2, 0.9 Hz, 1H, CH$_{ar}$), 8.04 (d, J=8.1 Hz, 1H, CH$_{ar}$), 7.83 (dt, J=7.5, 1.8 Hz, 1H, CH$_{ar}$), 7.48-7.43 (m, 1H, CH$_{ar}$), 3.11 (d, J=6.6 Hz, 2H, CH$_2$CO), 2.34-2.30 (m, 1H, CH), 1.00 (d, J=6.6 Hz, 6H, C(CH$_3$)$_2$). MS: MH$^+$=164.

Example 9: Synthesis of 1-(3,5-dimethylpyridin-2-yl)ethanone

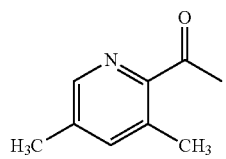

1-(3,5-dimethylpyridin-2-yl)ethanone was synthesized from 3,5-dimethyl-pyridine-2-carbonitrile and methylmagnesium bromide in the same manner as Example 8 to provide the product as a colorless oil. $^1$H NMR (300 MHz, CDCl$_3$): δ 8.33 (d, J=0.9 Hz, 1H, CH$_{ar}$), 7.37 (d, J=1.5 Hz, 1H, CH$_{ar}$), 2.69 (s, 3H, CH$_3$), 2.56 (s, 3H, CH$_3$), 2.36 (s, 3H, CH$_3$CO). MS: MH$^+$=150.

Example 10: Synthesis of 1-(6-methoxypyridin-2-yl)ethanone

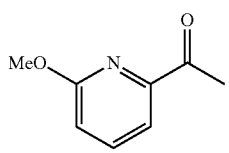

1-(6-methoxypyridin-2-yl)ethanone was synthesized from 6-Methoxy-pyridine-2-carbonitrile and methylmagnesium bromide in the same manner as Example 8 to provide the product as a solid. $^1$H NMR (300 MHz, CDCl$_3$): δ 7.72-7.62 (m, 2H, CH$_{ar}$), 6.93 (dd, J=8.1, 0.9 Hz, 1H, CH$_{ar}$), 4.00 (s, 3H, CH$_3$OAr), 2.69 (s, 3H, CH$_3$CO). MS: MH$^+$=152.

Example 11: Synthesis of 1-(quinolin-2-yl)ethanone

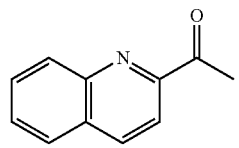

1-(quinolin-2-yl)ethanone was synthesized from Quinoline-2-carbonitrile and methylmagnesium bromide in the same manner as Example 8 to provide the product as a white solid. $^1$H NMR (300 MHz, CDCl$_3$): δ 8.27 (d, J=8.4 Hz, 1H, CH$_{ar}$), 8.20 (d, J=8.7 Hz, 1H, CH$_{ar}$), 8.13 (d, J=8.7 Hz, 1H, CH$_{ar}$), 7.87 (d, J=8.4 Hz, 1H, CH$_{ar}$), 7.82-7.76 (m, 1H, CH$_{ar}$), 7.68-7.62 (m, 1H, CH$_{ar}$), 2.88 (s, 3H, CH$_3$CO). MS: MH$^+$=172.

Example 12: Synthesis of 1-(pyridin-2-yl)propan-1-one

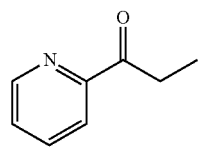

1-(pyridin-2-yl)propan-1-one was synthesized from pyridine-2-carbonitrile and ethylmagnesium bromide in the same manner as Example 8 to provide the product as a Light-yellow oil. $^1$H NMR (300 MHz, CDCl$_3$): δ 8.68 (dt, J=4.8, 0.9 Hz, 1H, CH$_{ar}$), 8.05 (dt, J=8.1, 1.2 Hz, 1H, CH$_{ar}$), 7.83 (dt, J=7.5, 1.8 Hz, 1H, CH$_{ar}$), 7.49-7.44 (m, 1H, CH$_{ar}$), 3.25 (q, J=7.5 Hz, 2H, CH$_2$CO), 1.22 (t, J=7.5 Hz, 3H, CH$_3$). MS: MH$^+$=136.

Example 13: Synthesis of 1-(pyridin-2-yl)butan-1-one

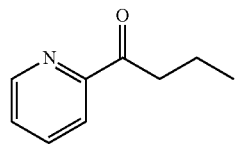

1-(pyridin-2-yl)butan-1-one was synthesized from Pyridine-2-carbonitrile and propylmagnesium bromide in the same manner as Example 8 to provide the product as a colorless oil. $^1$H NMR (300 MHz, CDCl$_3$): δ 8.68 (dq, J=5.1, 0.9 Hz, 1H, CH$_{ar}$), 8.04 (dt, J=8.1, 1.2 Hz, 1H, CH$_{ar}$), 7.83 (dt, J=7.5, 1.8 Hz, 1H, CH$_{ar}$), 7.48-7.44 (m, 1H, CH$_{ar}$), 3.20

(t, J=7.5 Hz, 2H, CH₂CO), 1.81-1.74 (m, 2H, CH₂), 1.02 (t, J=7.5 Hz, 3H, CH₃). MS: MH⁺=150.

Example 14: Synthesis of 1-(pyridin-2-yl)heptan-1-one

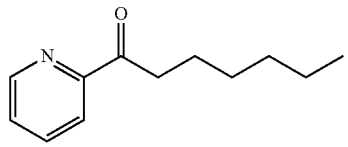

1-(pyridin-2-yl)heptan-1-one was synthesized from pyridine-2-carbonitrile and hexyl magnesium bromide in the same manner as Example 8 to provide the product as a colorless oil. ¹H NMR (300 MHz, CDCl₃): δ 8.68 (dq, J=4.8, 0.9 Hz, 1H, CH$_{ar}$), 8.04 (dt, J=8.1, 0.9 Hz, 1H, CH$_{ar}$), 7.83 (dt, J=7.5, 1.8 Hz, 1H, CH$_{ar}$), 7.48-7.44 (m, 1H, CH$_{ar}$), 3.21 (t, J=7.5 Hz, 2H, CH₂CO), 1.76-1.68 (m, 2H, CH₂), 1.42-1.26 (m, 6H, 3×CH₂), 0.89 (t, J=7.2 Hz, 3H, CH₃). MS: MH⁺=192.

Example 15: Synthesis of 2-cyclohexyl-1-(pyridin-2-yl)ethanone

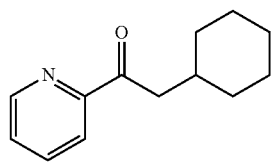 [SMILES: O=C(CC1CCCCC1)c1ccccn1]

2-Cyclohexyl-1-(pyridin-2-yl)ethanone was synthesized from pyridine-2-carbonitrile and cyclohexylmethyl magnesium bromide in the same manner as example 8 to provide the product as a colorless oil. ¹H NMR (300 MHz, CDCl₃): δ 8.68 (dt, J=3.9, 0.6 Hz, 1H, CH$_{ar}$), 8.03 (d, J=8.1 Hz, 1H, CH$_{ar}$), 7.83 (dt, J=7.8, 1.8 Hz, 1H, CH$_{ar}$), 7.48-7.43 (m, 1H, CH$_{ar}$), 3.10 (d, J=7.2 Hz, 2H, CH₂CO), 2.04-2.00 (m, 1H, CH), 1.78-1.02 (m, 10H, 5×CH₂). MS: MH⁺=204.

Example 16: Synthesis of 1-(pyridin-2-yl)undecan-1-one

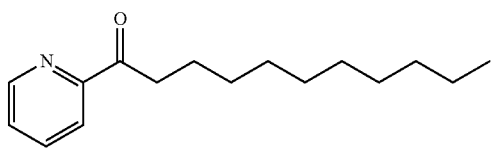 [SMILES: CCCCCCCCCCC(=O)c1ccccn1]

1-(pyridin-2-yl)undecan-1-one was synthesized from pyridine-2-carbonitrile and undecanyl magnesium bromide in the same manner as example 8 to provide the product as a colorless oil. ¹H NMR (300 MHz, CDCl₃): δ 8.68 (dq, J=4.8, 0.9 Hz, 1H, CH$_{ar}$), 8.04 (dt, J=8.1, 1.2 Hz, 1H, CH$_{ar}$), 7.83 (dt, J=7.5, 1.8 Hz, 1H, CH$_{ar}$), 7.48-7.43 (m, 1H, CH$_{ar}$), 3.21 (t, J=7.5 Hz, 2H, CH₂CO), 1.75-1.68 (m, 2H, CH₂), 1.35-1.23 (m, 14H, 7×CH₂), 0.88 (t, J=6.9 Hz, 3H, CH₃). MS: MH⁺=248.

Example 17: Synthesis of ethyl 3-(6-methylpyridin-2-yl)-3-oxopropanoate

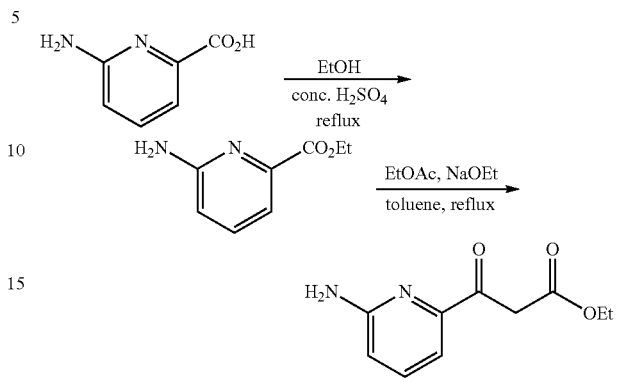

A reaction mixture of 6-methylpicolinic acid (1.0 g, 7.3 mmol) and conc. sulfuric acid (~98%, 0.6 mL) in ethanol (40 mL) was refluxed for 24 hours. The extra ethanol was evaporated, followed by addition of water (20 mL) at 0° C. The pH was adjusted to 9 with sodium bicarbonate powder. Then the mixture was extracted with ethyl acetate (30 mL×3), and the combined organic layer was dried over anhydrous sodium sulfate and concentrated to afford 1.20 g of ethyl 6-methylpicolinate as a colorless oil. MS: MH⁺=166.

A solution of anhydrous ethyl acetate (1 mL, 9.9 mmol) in toluene (10 mL), was treated with sodium ethoxide (449 mg, 6.6 mg) at room temperature. The mixture was stirred under argon atmosphere for 1 hour, and then, ethyl 6-methylpicolinate (499 mg, 3.3 mmol) was added. The reaction mixture was heated to reflux for 20 hours. After cooling to room temperature, it was acidified (pH=6) with acetic acid, followed by addition of water (20 mL) and extracted with ethyl acetate (20 mL×3). The combined organic layer was dried over anhydrous sodium sulfate, concentrated and purified through silica gel column chromatography (ethyl acetate:hexanes=10:90 to 20:80) to afford 440 mg of compound ethyl 3-(6-methylpyridin-2-yl)-3-oxopropanoate as light-yellow oil. ¹H NMR (300 MHz, CDCl₃): δ 7.87 (d, J=7.8 Hz, 1H, CH$_{ar}$), 7.72 (t, J=7.8 Hz, 1H, CH$_{ar}$), 7.33 (d, J=7.5 Hz, 1H, CH$_{ar}$), 4.23-4.16 (m, 4H, 2×CH₂), 2.59 (s, 3H, ArCH₃), 1.24 (t, J=7.2 Hz, 3H, CH₃). MS: MH⁺=208.

Example 18: Synthesis of ethyl 3-(4-methylpyridin-2-yl)-3-oxopropanoate

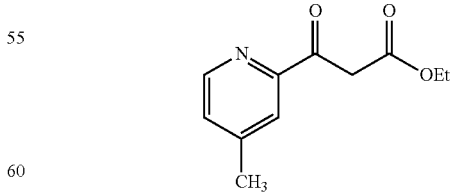

Ethyl 3-(4-methylpyridin-2-yl)-3-oxopropanoate was synthesized from 4-methyl-pyridine-2-carboxylic acid in the same manner as Example 17 to provide the product as a light yellow oil. ¹H NMR (300 MHz, CDCl₃): δ 8.52 (d, J=5.1 Hz, 1H, CH$_{ar}$), 7.90 (d, J=0.6 Hz, 1H, CH$_{ar}$), 7.30 (dd, J=5.1, 0.9 Hz, 1H, CH$_{ar}$), 4.23-4.16 (m, 4H, 2×CH$_2$), 2.43 (s, 3H, ArCH$_3$), 1.24 (t, J=7.2 Hz, 3H, CH$_3$). MS: MH$^+$=208.

Example 19: Synthesis of 2-bromo-1-(pyridin-2-yl)ethanone hydrobromide

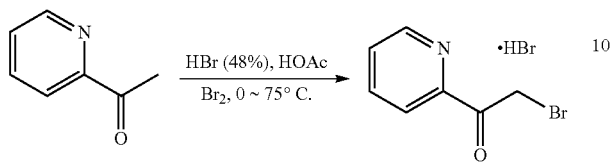

To a solution of 2-acetylpyridine (2.42 g, 20 mmol) in a mixture of 48% hydrobromic acid (2.26 mL, 20 mmol) and acetic acid (22 mL) at 0° C., was added dropwise bromine (1.13 mL, 22 mmol). The reaction mixture was stirred at room temperature for 1 hour, and then 75° C. for 3 hours. After cooling to room temperature, it was diluted with tetrahydrofuran (25 mL) and stirred overnight. The product was collected by filtration, washed with tetrahydrofuran and dried under vacuum. 5.38 g of 2-bromo-1-(pyridin-2-yl) ethanone hydrobromide was afforded as white solid.

Example 20: Synthesis of 4-(pyridin-2-yl)-N-(pyrimidin-2-yl)thiazol-2-amine

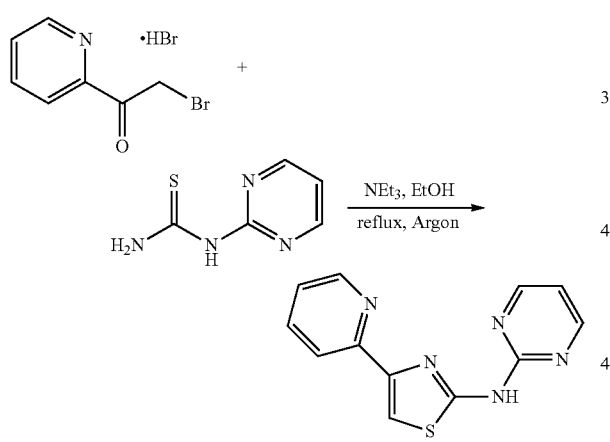

A reaction mixture of 2-bromo-1-(pyridin-2-yl) ethanone hydrobromide (1.69 g, 6 mmol), 1-(pyrimidin-2-yl)thiourea (0.93 g, 6 mmol), and triethylamine (2.1 mL, 15 mmol) in ethanol (30 mL) was refluxed for 1 hour under argon atmosphere. After cooling to room temperature, the reaction mixture was quenched with water (100 mL) and stirred for another 2 hours. The crude product was collected by filtration and was further purified by recrystallization in methanol. 1.14 g of compound 4-(pyridin-2-yl)-N-(pyrimidin-2-yl)thiazol-2-amine was afforded as white solid. $^1$H NMR (500 MHz, DMSO-d$_6$): δ 11.88 (s, 1H, NH), 8.67 (d, J=5.0 Hz, 2H, CH$_{ar}$), 8.61-8.59 (m, 1H, CH$_{ar}$), 7.99 (d, J=8.0 Hz, 1H, CH$_{ar}$), 7.89 (dt, J=7.5, 1.5 Hz, 1H, CH$_{ar}$), 7.75 (s, 1H, CH$_{ar}$), 7.33-7.31 (m, 1H, CH$_{ar}$), 7.06 (t, J=5.0 Hz, 1H, CH$_{ar}$). MS: MH$^+$=256. 4-(pyridin-2-yl)-N-(pyrimidin-2-yl) thiazol-2-amine could be further converted to the HCl salt using the following procedure: A suspension of 4-(pyridin-2-yl)-N-(pyrimidin-2-yl)thiazol-2-amine (102 mg, 0.4 mmol) in methanol (10 mL) was treated 4 M HCl solution (in 1,4-dioxane, 1 mL). Then, it was heated to reflux and the reaction mixture became a clear solution. The solvent was removed by evaporation and the given residue was further purified by recrystallization in ethyl acetate to afford 130 mg of HCl salt. $^1$H NMR (300 MHz, DMSO-d$_6$): δ 8.71-8.67 (m, 3H, CH$_{ar}$), 8.33-8.24 (m, 3H, CH$_{ar}$), 7.71-7.67 (m, 1H, CH$_{ar}$), 7.09 (t, J=5.1 Hz, 1H, CH$_{ar}$). MS: MH$^+$=256.

Example 21: Synthesis of N,4-diphenylthiazol-2-amine

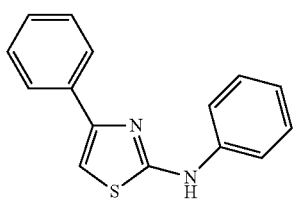 [SMILES: c1ccc(Nc2nc(-c3ccccc3)cs2)cc1]

N,4-diphenylthiazol-2-amine was synthesized from 2-bromo-1-phenyl-ethanone and phenyl-thiourea in the same manner as Example 20 to provide the product as a light-yellow solid. $^1$H NMR (300 MHz, CDCl$_3$): δ 7.88-7.84 (m, 2H, CH$_{ar}$), 7.55 (s, 1H, NH), 7.43-7.28 (m, 7H, CH$_{ar}$), 7.10-7.05 (m, 1H, CH$_{ar}$), 6.83 (d, J=1.8 Hz, 1H, CH$_{ar}$). MS: MH$^+$=253.

Example 22: Synthesis of N-phenyl-4-(pyridin-2-yl)thiazol-2-amine

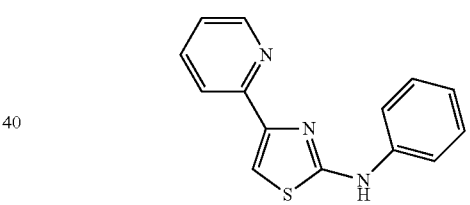

N-phenyl-4-(pyridin-2-yl)thiazol-2-amine was synthesized from 2-bromo-1-pyridin-2-yl-ethanone and phenyl-thiourea in the same manner as Example 20 to provide the product as a light-yellow solid. $^1$H NMR (300 MHz, CDCl$_3$): δ 8.62-8.60 (m, 1H, CH$_{ar}$), 8.00 (dt, J=8.1, 1.2 Hz, 1H, CH$_{ar}$), 7.75 (dt, J=8.1, 2.1 Hz, 1H, CH$_{ar}$), 7.44-7.34 (m, 6H, 5×CH$_{ar}$ and NH overlapped), 7.23-7.18 (m, 1H, CH$_{ar}$), 7.11-7.06 (m, 1H, CH$_{ar}$). MS: MH$^+$=254.

Example 23: Synthesis of 4-phenyl-N-(pyrimidin-2-yl)thiazol-2-amine

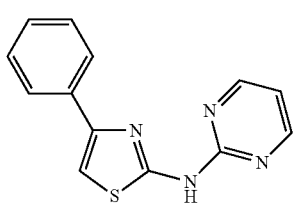 [SMILES: c1ccc(-c2csc(Nc3ncccn3)n2)cc1]

4-Phenyl-N-(pyrimidin-2-yl)thiazol-2-amine was synthesized from 2-bromo-1-phenyl-ethanone and pyrimidin-2-yl-thiourea in the same manner as Example 20 to provide the product as a white solid. $^1$H NMR (300 MHz, DMSO-d$_6$): δ 11.80 (s, 1H, NH), 8.63 (d, J=5.1 Hz, 2H, CH$_{ar}$), 7.92-7.89 (m, 2H, CH$_{ar}$), 7.52 (s, 1H, CH$_{ar}$), 7.43-7.38 (m, 2H, CH$_{ar}$), 7.31-7.29 (m, 1H, CH$_{ar}$), 7.03 (t, J=5.1 Hz, 1H, CH$_{ar}$). MS: MH$^+$=255.

Example 24: Synthesis of N,4-di(pyridin-2-yl)thiazol-2-amine

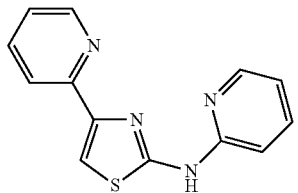 [SMILES: c1ccc(Nc2nc(-c3ccccn3)cs2)nc1]

N,4-di(pyridin-2-yl)thiazol-2-amine was synthesized from 2-bromo-1-pyridin-2-yl-ethanone and pyridin-2-yl-thiourea in the same manner as Example 20 to provide the product as a white solid. $^1$H NMR (500 MHz, DMSO-d$_6$): δ 11.45 (s, 1H, NH), 8.60 (d, J=4.5 Hz, 1H, CH$_{ar}$), 8.32 (dd, J=5.5, 2.0 Hz, 1H, CH$_{ar}$), 7.97 (d, J=8.0 Hz, 1H, CH$_{ar}$), 7.88 (dt, J=8.0, 2.0 Hz, 1H, CH$_{ar}$), 7.74-7.71 (m, 1H, CH$_{ar}$), 7.65 (s, 1H, CH$_{ar}$), 7.33-7.30 (m, 1H, CH$_{ar}$), 7.11 (d, J=8.5 Hz, 1H, CH$_{ar}$), 6.96-6.93 (m, 1H, CH$_{ar}$). MS: MH$^+$=255.

Example 25: Synthesis of 4-(pyridin-3-yl)-N-(pyrimidin-2-yl)thiazol-2-amine

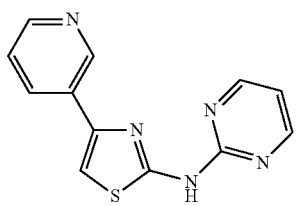 [SMILES: c1cnc(Nc2nc(-c3cccnc3)cs2)nc1]

4-(pyridin-3-yl)-N-(pyrimidin-2-yl)thiazol-2-amine was synthesized from 2-bromo-1-pyridin-3-yl-ethanone and pyrimidin-2-yl-thiourea in the same manner as Example 20 to provide the product as a gray solid. $^1$H NMR (300 MHz, DMSO-d$_6$): δ 11.93 (s, 1H, NH), 9.14-9.13 (m, 1H, CH$_{ar}$), 8.65 (d, J=4.8 Hz, 2H, CH$_{ar}$), 8.51 (dd, J=5.1, 1.8 Hz, 1H, CH$_{ar}$), 8.25-8.21 (m, 1H, CH$_{ar}$), 7.70 (s, 1H, CH$_{ar}$), 7.46-7.42 (m, 1H, CH$_{ar}$), 7.04 (t, J=4.8 Hz, 1H, CH$_{ar}$). MS: MH$^+$=256.

Example 26: Synthesis of 4-(pyridin-4-yl)-N-(pyrimidin-2-yl)thiazol-2-amine

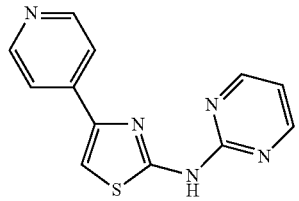 [SMILES: c1cnc(Nc2nc(-c3ccncc3)cs2)nc1]

4-(pyridin-4-yl)-N-(pyrimidin-2-yl)thiazol-2-amine was synthesized from 2-bromo-1-pyridin-4-yl-ethanone and pyrimidin-2-yl-thiourea in the same manner as Example 20 to provide the product as a gray solid. $^1$H NMR (300 MHz, DMSO-d$_6$): δ 11.93 (s, 1H, NH), 8.65 (d, J=4.8 Hz, 2H, CH$_{ar}$), 8.59 (dd, J=4.8, 1.5 Hz, 2H, CH$_{ar}$), 7.89 (s, 1H, CH$_{ar}$), 7.85-7.83 (m, 2H, CH$_{ar}$), 7.05 (t, J=4.8 Hz, 1H, CH$_{ar}$). MS: MH$^+$=256.

Example 27: Synthesis of N-(pyrazin-2-yl)-4-(pyridin-2-yl)thiazol-2-amine

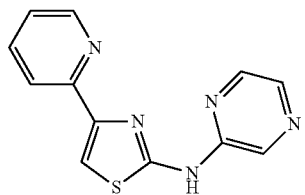 [SMILES: c1ccc(-c2csc(Nc3cnccn3)n2)nc1]

N-(pyrazin-2-yl)-4-(pyridin-2-yl)thiazol-2-amine was synthesized from 2-bromo-1-pyridin-2-yl-ethanone and pyrimidin-2-yl-thiourea in the same manner as Example 20 to provide the product as a brown solid. $^1$H NMR (300 MHz, DMSO-d$_6$): δ 11.87 (s, 1H, NH), 8.60-8.57 (m, 1H, CH$_{ar}$), 8.51 (d, J=1.5 Hz, 1H, CH$_{ar}$), 8.32 (dd, J=3.0, 1.5 Hz, 1H, CH$_{ar}$), 8.13 (d, J=2.4 Hz, 1H, CH$_{ar}$), 7.96 (dt, J=7.8, 1.2 Hz, 1H, CH$_{ar}$), 7.87 (dt, J=7.8, 1.8 Hz, 1H, CH$_{ar}$), 7.73 (s, 1H, CH$_{ar}$), 7.33-7.29 (m, 1H, CH$_{ar}$). MS: MH$^+$=256.

Example 28: Synthesis of 4-(pyridin-2-yl)-N-(pyrimidin-4-yl)thiazol-2-amine

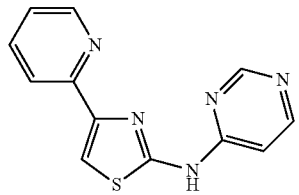 [SMILES: c1ccc(-c2csc(Nc3ccncn3)n2)nc1]

4-(pyridin-2-yl)-N-(pyrimidin-4-yl)thiazol-2-amine was synthesized from 2-bromo-1-pyridin-2-yl-ethanone and pyrimidin-4-yl-thiourea in the same manner as Example 20 to provide the product as a brown solid. $^1$H NMR (300 MHz, DMSO-d$_6$): δ 11.91 (s, 1H, NH), 8.84 (d, J=0.9 Hz, 1H, CH$_{ar}$), 8.60-8.57 (m, 1H, CH$_{ar}$), 8.46 (d, J=6.0 Hz, 1H, CH$_{ar}$), 7.95 (dt, J=7.8, 1.2 Hz, 1H, CH$_{ar}$), 7.87 (dt, J=8.1, 2.1 Hz, 1H, CH$_{ar}$), 7.80 (s, 1H, CH$_{ar}$), 7.34-7.29 (m, 1H, CH$_{ar}$), 7.10 (dd, J=5.7, 1.2 Hz, 1H, CH$_{ar}$). MS: MH$^+$=256.

Example 29: Synthesis of 4-(6-bromopyridin-2-yl)-N-(pyrimidin-2-yl)thiazol-2-amine

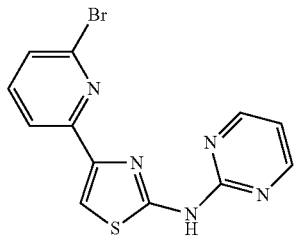 [SMILES: Brc1cccc(-c2csc(Nc3ncccn3)n2)n1]

4-(6-bromopyridin-2-yl)-N-(pyrimidin-2-yl)thiazol-2-amine was synthesized from 2-bromo-1-(6-bromo-pyridin-2-yl)-ethanone and pyrimidin-2-yl-thiourea in the same manner as Example 20 to provide the product as a gray solid. $^1$H NMR (300 MHz, DMSO-d$_6$): δ 11.92 (s, 1H, NH), 8.65 (d, J=4.5 Hz, 2H, CH$_{ar}$), 7.95 (dd, J=7.8, 0.9 Hz, 1H, CH$_{ar}$), 7.82 (t, J=8.1 Hz, 1H, CH$_{ar}$), 7.75 (d, J=0.6 Hz, 1H, CH$_{ar}$), 7.54 (dd, J=8.1, 0.9 Hz, 1H, CH$_{ar}$), 7.05 (t, J=4.8 Hz, 1H, CH$_{ar}$). MS: MH$^+$=334.

Example 30: Synthesis of 4-(4-methylpyridin-2-yl)-N-(pyrimidin-2-yl)thiazol-2-amine

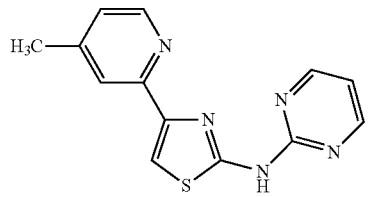 [SMILES: Cc1ccnc(-c2csc(Nc3ncccn3)n2)c1]

4-(4-methylpyridin-2-yl)-N-(pyrimidin-2-yl)thiazol-2-amine was synthesized from 2-bromo-1-(4-methyl-pyridin-2-yl)-ethanone and pyrimidin-2-yl-thiourea in the same manner as Example 20 to provide the product as a dark gray solid. $^1$H NMR (300 MHz, DMSO-d$_6$): δ 11.81 (s, 1H, NH), 8.64 (d, J=4.8 Hz, 2H, CH$_{ar}$), 8.42 (dd, J=4.2, 0.6 Hz, 1H, CH$_{ar}$), 7.82 (t, J=0.9 Hz, 1H, CH$_{ar}$), 7.70 (s, 1H, CH$_{ar}$), 7.14-7.12 (m, 1H, CH$_{ar}$), 7.04 (t, J=4.8 Hz, 1H, CH$_{ar}$), 2.36 (s, 3H, ArCH$_3$). MS: MH$^+$=270.

Example 31: Synthesis of 4-(3,5-dimethylpyridin-2-yl)-N-(pyrimidin-2-yl)thiazol-2-amine

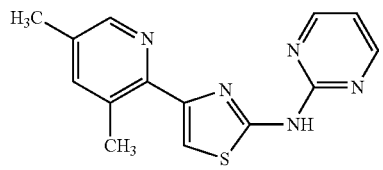 [SMILES: Cc1cnc(-c2csc(Nc3ncccn3)n2)c(C)c1]

4-(3,5-dimethylpyridin-2-yl)-N-(pyrimidin-2-yl)thiazol-2-amine was synthesized from 2-bromo-1-(3,5-dimethyl-pyridin-2-yl)-ethanone and pyrimidin-2-yl-thiourea in the same manner as Example 20 to provide the product as a light-gray solid. $^1$H NMR (300 MHz, DMSO-d$_6$): δ 11.70 (s, 1H, NH), 8.64 (d, J=4.8 Hz, 2H, CH$_{ar}$), 8.24 (s, 1H, CH$_{ar}$), 7.46 (s, 1H, CH$_{ar}$), 7.41 (s, 1H, CH$_{ar}$), 7.02 (t, J=4.8 Hz, 1H, CH$_{ar}$), 2.52 (s, 3H, ArCH$_3$), 2.27 (s, 3H, ArCH$_3$). MS: MH$^+$=284.

Example 32: Synthesis of 6-(2-(pyrimidin-2-ylamino)thiazol-4-yl)pyridin-2-ol dihydrochloride

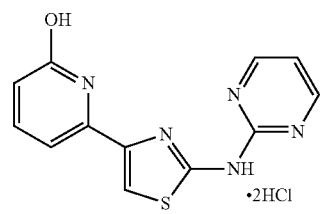 [SMILES: Oc1cccc(-c2csc(Nc3ncccn3)n2)n1 ; "·2HCl"]

6-(2-(pyrimidin-2-ylamino)thiazol-4-yl)pyridin-2-ol dihydrochloride was synthesized from 2-bromo-1-(6-hydroxy-pyridine-2-yl)-ethanone dihydrochloride and pyrimidin-2-yl-thiourea in the same manner as Example 20 to provide the product as a gray solid. $^1$H NMR (300 MHz, DMSO-d$_6$): δ 11.93 (s, 1H, NH), 8.64 (d, J=4.5 Hz, 2H, CH$_{ar}$), 7.92 (s, 1H, CH$_{ar}$), 7.53 (t, J=8.1 Hz, 1H, CH$_{ar}$), 7.05 (t, J=4.8 Hz, 1H, CH$_{ar}$), 6.89 (d, J=6.9 Hz, 1H, CH$_{ar}$), 6.33 (d, J=9.3 Hz, 1H, CH$_{ar}$). MS: MH$^+$=272.

Example 33: Synthesis of N-(pyrimidin-2-yl)-4-(quinolin-2-yl)thiazol-2-amine dihydrochloride

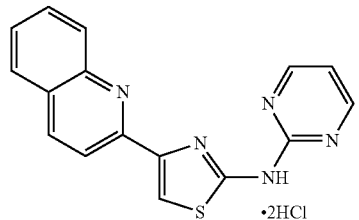 [SMILES: c1cnc(Nc2nc(-c3ccc4ccccc4n3)cs2)nc1]

N-(pyrimidin-2-yl)-4-(quinolin-2-yl)thiazol-2-amine dihydrochloride was synthesized from 2-bromo-1-quinolin-2-yl-ethanone dihydrochloride and pyrimidin-2-yl-thiourea in the same manner as Example 20 to provide the product as a gray solid. $^1$H NMR (300 MHz, DMSO-d$_6$): δ 8.84 (d, J=9.0 Hz, 1H, CH$_{ar}$), 8.70 (d, J=5.1 Hz, 1H, CH$_{ar}$), 8.56 (s, 1H, CH$_{ar}$), 8.38 (dd, J=8.7, 3.3 Hz, 1H, CH$_{ar}$), 8.16 (d, J=7.8 Hz, 1H, CH$_{ar}$), 7.96 (t, J=7.5 Hz, 1H, CH$_{ar}$), 7.75 (t, J=7.8 Hz, 1H, CH$_{ar}$), 7.10 (t, J=4.8 Hz, 1H, CH$_{ar}$). MS: MH$^+$=306.

Example 34: Synthesis of N-(5-chloropyrimidin-2-yl)-4-(pyridin-2-yl)thiazol-2-amine

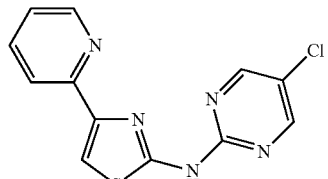

N-(5-chloropyrimidin-2-yl)-4-(pyridin-2-yl)thiazol-2-amine was synthesized from 2-bromo-1-pyridin-2-yl-ethanone and (5-chloro-pyrimidin-2-yl)-thiourea in the same manner as Example 20 to provide the product as a white solid. $^1$H NMR (300 MHz, DMSO-d$_6$): δ 12.11 (s, 1H, NH), 8.74 (s, 2H, CH$_{ar}$), 8.58 (d, J=5.1 Hz, 1H, CH$_{ar}$), 7.97 (d, J=8.1 Hz, 1H, CH$_{ar}$), 7.87 (m, 1H, CH$_{ar}$), 7.76 (s, 1H, CH$_{ar}$), 7.31 (m, 1H, CH$_{ar}$). MS: MH$^+$=290.

Example 35: Synthesis of N-(5-bromopyrimidin-2-yl)-4-(pyridin-2-yl)thiazol-2-amine

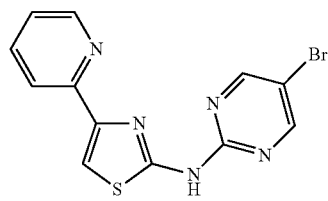 [SMILES: Brc1cnc(Nc2nc(-c3ccccn3)cs2)nc1]

N-(5-bromopyrimidin-2-yl)-4-(pyridin-2-yl)thiazol-2-amine was synthesized from 2-bromo-1-pyridin-2-yl-ethanone and (5-bromo-pyrimidin-2-yl)-thiourea in the same manner as Example 20 to provide the product as a white solid. $^1$H NMR (300 MHz, DMSO-d$_6$): δ 12.10 (s, 1H, NH), 8.79 (s, 2H, CH$_{ar}$), 8.58-8.57 (m, 1H, CH$_{ar}$), 7.96 (d, J=7.8 Hz, 1H, CH$_{ar}$), 7.86 (dt, J=8.1, 1.8 Hz, 1H, CH$_{ar}$), 7.77 (s, 1H, CH$_{ar}$), 7.33-7.28 (m, 1H, CH$_{ar}$). MS: MH$^+$=334.

Example 36: Synthesis of N-(4-methylpyrimidin-2-yl)-4-(pyridin-2-yl)thiazol-2-amine

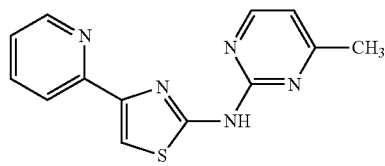 [SMILES: Cc1ccnc(Nc2nc(-c3ccccn3)cs2)n1]

N-(4-methylpyrimidin-2-yl)-4-(pyridin-2-yl)thiazol-2-amine was synthesized from 2-bromo-1-pyridin-2-yl-ethanone and (4-methyl-pyrimidin-2-yl)-thiourea in the same manner as Example 20 to provide the product as a gray solid. $^1$H NMR (300 MHz, DMSO-d$_6$): δ 11.74 (s, 1H, NH), 8.57 (d, J=4.2 Hz, 1H, CH$_{ar}$), 8.48 (d, J=4.8 Hz, 1H, CH$_{ar}$), 7.96 (d, J=7.8 Hz, 1H, CH$_{ar}$), 7.86 (dt, J=7.5, 1.8 Hz, 1H, CH$_{ar}$), 7.71 (s, 1H, CH$_{ar}$), 7.31-7.27 (m, 1H, CH$_{ar}$), 6.92 (d, J=4.8 Hz, 1H, CH$_{ar}$), 2.44 (s, 3H, ArCH$_3$). MS: MH$^+$=270.

Example 37: Synthesis of 4-(pyridin-2-yl)-N-(4-(trifluoromethyl)pyrimidin-2-yl)thiazol-2-amine

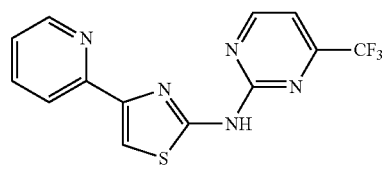 [SMILES: FC(F)(F)c1ccnc(Nc2nc(-c3ccccn3)cs2)n1]

4-(pyridin-2-yl)-N-(4-(trifluoromethyl)pyrimidin-2-yl)thiazol-2-amine was synthesized from 2-bromo-1-pyridin-2-yl-ethanone and (4-trifluromethyl-pyrimidin-2-yl)-thiourea in the same manner as Example 20 to provide the product as a gray solid. $^1$H NMR (300 MHz, DMSO-d$_6$): δ 12.42 (s, 1H, NH), 8.98 (d, J=4.5 Hz, 1H, CH$_{ar}$), 8.58 (d, J=3.6 Hz, 1H, CH$_{ar}$), 7.97 (d, J=8.1 Hz, 1H, CH$_{ar}$), 7.89-7.83 (m, 2H, CH$_{ar}$), 7.48 (d, J=4.5 Hz, 1H, CH$_{ar}$), 7.31 (t, J=5.7 Hz, 1H, CH$_{ar}$). MS: MH$^+$=324.

Example 38: Synthesis of 6-methyl-N-(4-(pyridin-2-yl)thiazol-2-yl)benzo[d]thiazol-2-amine

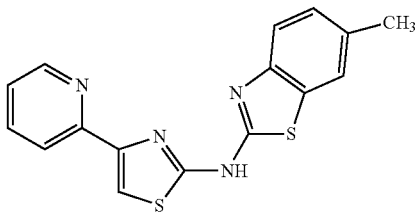 [SMILES: Cc1ccc2nc(Nc3nc(-c4ccccn4)cs3)sc2c1]

6-methyl-N-(4-(pyridin-2-yl)thiazol-2-yl)benzo[d]thiazol-2-amine was synthesized from 2-bromo-1-pyridin-2-yl-ethanone and (6-methyl-benzothiazol-2-yl)-thiourea in the same manner as Example 20 to provide the product as a light-brown solid. $^1$H NMR (300 MHz, CDCl$_3$): δ 8.62 (s, 1H, CH$_{ar}$), 8.13 (d, J=6.6 Hz, 1H, CH$_{ar}$), 7.82 (t, J=7.5 Hz, 1H, CH$_{ar}$), 7.64-7.59 (m, 1H, CH$_{ar}$), 7.52-7.48 (m, 2H, CH$_{ar}$), 7.23-7.18 (m, 2H, CH$_{ar}$), 2.44 (s, 3H, ArCH$_3$). MS: MH$^+$=325.

Example 39: Synthesis of 5-methyl-4-(pyridin-2-yl)-N-(pyrimidin-2-yl)thiazol-2-amine

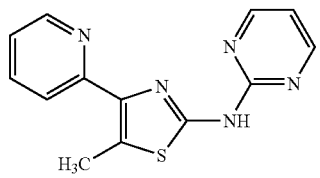 [SMILES: Cc1sc(Nc2ncccn2)nc1-c1ccccn1]

5-methyl-4-(pyridin-2-yl)-N-(pyrimidin-2-yl)thiazol-2-amine was synthesized from 2-bromo-1-pyridin-2-yl-propan-1-one and pyrimidin-2-yl-thiourea in the same manner as Example 20 to provide the product as a gray solid. $^1$H NMR (300 MHz, DMSO-d$_6$): δ 11.63 (s, 1H, NH), 8.61 (d, J=4.5 Hz, 3H, CH$_{ar}$), 7.97 (d, J=8.4 Hz, 1H, CH$_{ar}$), 7.84 (t, J=7.5 Hz, 1H, CH$_{ar}$), 7.28-7.24 (m, 1H, CH$_{ar}$), 7.01 (t, J=4.8 Hz, 1H, CH$_{ar}$), 2.72 (s, 3H, ArCH$_3$). MS: MH$^+$=270.

Example 40: Synthesis of 5-ethyl-4-(pyridin-2-yl)-N-(pyrimidin-2-yl)thiazol-2-amine

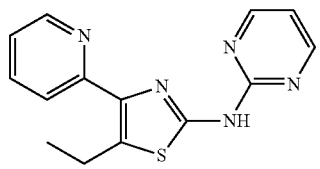 [SMILES: CCc1sc(Nc2ncccn2)nc1-c1ccccn1]

5-Ethyl-4-(pyridin-2-yl)-N-(pyrimidin-2-yl)thiazol-2-amine was synthesized from 2-bromo-1-pyridin-2-yl-butan-1-one and pyrimidin-2-yl-thiourea in the same manner as Example 20 to provide the product as a gray solid. $^1$H NMR (300 MHz, DMSO-$d_6$): δ 11.61 (s, 1H, NH), 8.62-8.59 (m, 3H, CH$_{ar}$), 7.97 (d, J=7.8 Hz, 1H, CH$_{ar}$), 7.84 (dt, J=7.8, 1.8 Hz, 1H, CH$_{ar}$), 7.28-7.24 (m, 1H, CH$_{ar}$), 7.01 (t, J=4.8 Hz, 1H, CH$_{ar}$), 2.49-2.48 (m, 2H, ArCH$_2$, overlapped with the peaks of DMSO), 1.26 (t, J=7.5 Hz, 3H, CH$_3$). MS: MH$^+$=284.

Example 41: Synthesis of 5-isopropyl-4-(pyridin-2-yl)-N-(pyrimidin-2-yl)thiazol-2-amine

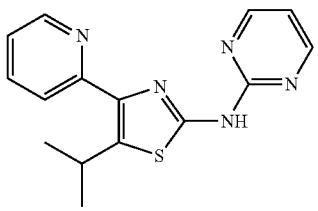 [SMILES: CC(C)c1sc(Nc2ncccn2)nc1-c1ccccn1]

5-isopropyl-4-(pyridin-2-yl)-N-(pyrimidin-2-yl)thiazol-2-amine was synthesized from 2-bromo-3-methyl-1-pyridin-2-yl-butan-1-one and pyrimidin-2-yl-thiourea in the same manner as Example 20 to provide the product as a light-gray solid. $^1$H NMR (300 MHz, CDCl$_3$): δ 9.95 (s, 1H, NH), 8.67-8.66 (m, 3H, CH$_{ar}$), 7.88 (d, J=7.8 Hz, 1H, CH$_{ar}$), 7.73 (t, J=8.1 Hz, 1H, CH$_{ar}$), 7.17 (m, 1H, CH$_{ar}$), 6.89 (t, J=5.1 Hz, 1H, CH$_{ar}$), 4.35-4.30 (m, 1H, CH), 1.40 (d, J=6.6 Hz, 6H, C(CH$_3$)$_2$). MS: MH$^+$=298.

Example 42: Synthesis of 5-pentyl-4-(pyridin-2-yl)-N-(pyrimidin-2-yl)thiazol-2-amine

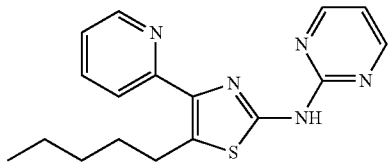 [SMILES: CCCCCc1sc(Nc2ncccn2)nc1-c1ccccn1]

5-Pentyl-4-(pyridin-2-yl)-N-(pyrimidin-2-yl)thiazol-2-amine was synthesized from 2-bromo-1-pyridin-2-yl-heptan-1-one and pyrimidin-2-yl-thiourea in the same manner as Example 20 to provide the product as a gray solid. $^1$H NMR (300 MHz, CDCl$_3$): δ 10.07 (s, 1H, NH), 8.66 (m, 3H, CH$_{ar}$), 7.88 (d, J=7.5 Hz, 1H, CH$_{ar}$), 7.73 (t, J=7.2 Hz, 1H, CH$_{ar}$), 7.16 (m, 1H, CH$_{ar}$), 6.89 (m, 1H, CH$_{ar}$), 3.29 (t, J=7.5 Hz, 2H, ArCH$_2$), 0.89 (m, 3H, CH$_3$). MS: MH$^+$=326.

Example 43: Synthesis of 5-cyclohexyl-4-(pyridin-2-yl)-N-(pyrimidin-2-yl)thiazol-2-amine dihydrochloride

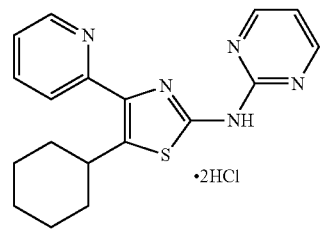 [SMILES: c1ccc(-c2nc(Nc3ncccn3)sc2C2CCCCC2)nc1]

5-Cyclohexyl-4-(pyridin-2-yl)-N-(pyrimidin-2-yl)thiazol-2-amine dihydrochloride was synthesized from 2-bromo-2-cyclohexyl-1-pyridin-2-yl-ethanone dihydrochloride and pyrimidin-2-yl-thiourea in the same manner as Example 20 to provide the product as a light-yellow solid. $^1$H NMR (300 MHz, DMSO-$d_6$): δ 8.74 (d, J=4.5 Hz, 1H, CH$_{ar}$), 8.65 (d, J=4.8 Hz, 1H, CH$_{ar}$), 8.24 (t, J=8.1 Hz, 1H, CH$_{ar}$), 8.04 (d, J=8.7 Hz, 1H, CH$_{ar}$), 7.63 (t, J=6.3 Hz, 1H, CH$_{ar}$), 7.05 (t, J=4.8 Hz, 1H, CH$_{ar}$), 3.58 (m, 1H, CH), 2.02-1.29 (m, 10H, 5×CH$_2$). MS: MH$^+$=338.

Example 44: Synthesis of 5-nonyl-4-(pyridin-2-yl)-N-(pyrimidin-2-yl)thiazol-2-amine

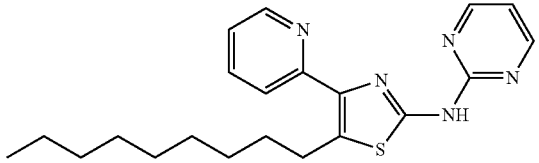 [SMILES: CCCCCCCCCc1sc(Nc2ncccn2)nc1-c1ccccn1]

5-Nonyl-4-(pyridin-2-yl)-N-(pyrimidin-2-yl)thiazol-2-amine was synthesized from 2-bromo-1-pyridin-2-yl-undecan-1-one and pyrimidin-2-yl-thiourea in the same manner as Example 20 to provide the product as a silver-gray solid. $^1$H NMR (300 MHz, CDCl$_3$): δ 9.70 (s, 1H, NH), 8.64 (d, J=5.1 Hz, 3H, CH$_{ar}$), 7.88 (d, J=8.1 Hz, 1H, CH$_{ar}$), 7.72 (dt, J=7.8, 1.8 Hz, 1H, CH$_{ar}$), 7.19-7.14 (m, 1H, CH$_{ar}$), 6.89 (t, J=5.1 Hz, 1H, CH$_{ar}$), 3.29 (t, J=8.1 Hz, 2H, ArCH$_2$), 1.77-1.69 (m, 2H, CH$_2$), 1.40-1.25 (m, 12H, 6×CH$_2$), 0.87 (t, J=6.9 Hz, 3H, CH$_3$). MS: MH$^+$=382.

Example 45: Synthesis of N-isopropyl-4-(pyridin-2-yl)-N-(pyrimidin-2-yl)thiazol-2-amine

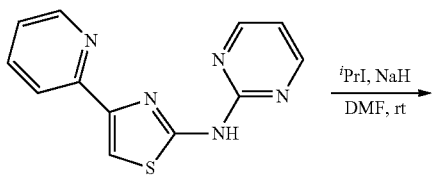

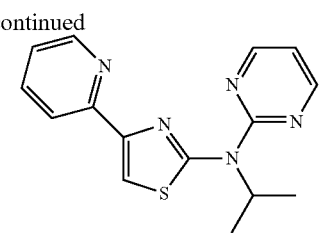

To a stirred suspension of 4-(pyridin-2-yl)-N-(pyrimidin-2-yl)thiazol-2-amine (51 mg, 0.2 mmol) in dimethylformamide (4 mL), was added sodium hydride (60%, 12 mg, 0.3 mmol), 2 minutes later, 2-iodopropane (20 μL, 0.2 mmol) was added. The stirring was continued for 24 hours. The reaction was quenched with sat. ammonium chloride (10 mL) and extracted with ethyl acetate (15 mL×3). The combined organic layer was dried over anhydrous sodium sulfate, concentrated, and purified through silica gel column chromatography (ethyl acetate:hexanes=30:70) to afford 54 mg of compound N-isopropyl-4-(pyridin-2-yl)-N-(pyrimidin-2-yl)thiazol-2-amine as white solid. $^1$H NMR (300 MHz, CDCl$_3$): δ 8.59 (s, 3H, CH$_{ar}$), 8.15 (d, J=7.2 Hz, 1H, CH$_{ar}$), 7.77 (s, 2H, CH$_{ar}$), 7.19 (s, 1H, CH$_{ar}$), 6.85 (s, 1H, CH$_{ar}$), 5.85 (m, 1H, NCH), 1.69 (d, J=6.0 Hz, 6H, C(CH$_3$)$_2$). MS: MH$^+$=298.

Example 46: Synthesis of N-methyl-4-(pyridin-2-yl)-N-(pyrimidin-2-yl)thiazol-2-amine

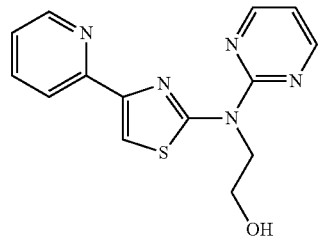

N-methyl-4-(pyridin-2-yl)-N-(pyrimidin-2-yl)thiazol-2-amine was synthesized from 4-(pyridin-2-yl)-N-(pyrimidin-2-yl)thiazol-2-amine and iodomethane in the same manner as Example 45 to provide the product as a white solid in 50% yield. $^1$H NMR (300 MHz, CDCl$_3$): δ 8.64-8.60 (m, 3H, CH$_{ar}$), 8.18-8.15 (m, 1H, CH$_{ar}$), 7.77 (dt, J=7.8, 1.8 Hz, 1H, CH$_{ar}$), 7.72 (s, 1H, CH$_{ar}$), 7.22-7.17 (m, 1H, CH$_{ar}$), 6.90 (t, J=4.8 Hz, 1H, CH$_{ar}$), 4.07 (s, 3H, NCH$_3$). MS: MH$^+$=270.

Example 47: Synthesis of N-benzyl-4-(pyridin-2-yl)-N-(pyrimidin-2-yl)thiazol-2-amine

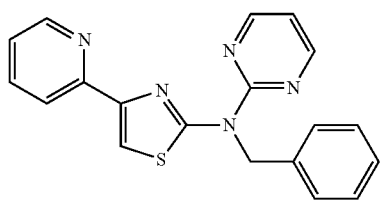 [SMILES: c1ccc(CN(c2ncccn2)c2nc(-c3ccccn3)cs2)cc1]

N-benzyl-4-(pyridin-2-yl)-N-(pyrimidin-2-yl)thiazol-2-amine was synthesized from 4-(pyridin-2-yl)-N-(pyrimidin-2-yl)thiazol-2-amine and benzyl bromide in the same manner as Example 45 to provide the product as a white solid. $^1$H NMR (300 MHz, CDCl$_3$): δ 8.62-8.60 (m, 3H, CH$_{ar}$), 8.08 (d, J=7.8 Hz, 1H, CH$_{ar}$), 7.75-7.70 (m, 2H, CH$_{ar}$), 7.51 (d, J=7.2 Hz, 2H, CH$_{ar}$), 7.29-7.15 (m, 4H, CH$_{ar}$, overlapped with the peaks of CHCl$_3$), 6.88 (t, J=4.8 Hz, 1H, CH$_{ar}$), 5.98 (s, 2H, NCH$_2$Ar). MS: MH$^+$=346.

Example 48: Synthesis of 2-((4-(pyridin-2-yl)thiazol-2-yl)(pyrimidin-2-yl)amino)ethanol

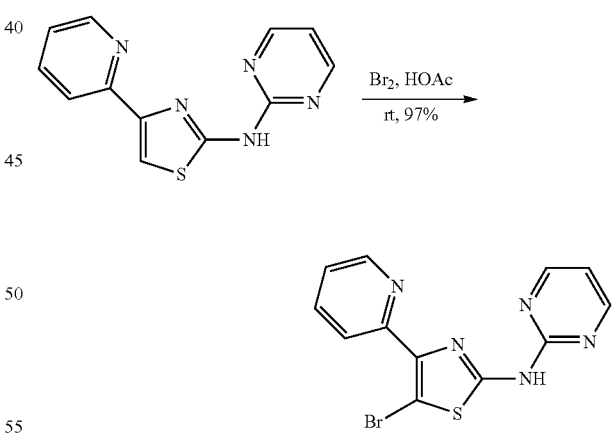

2-((4-(pyridin-2-yl)thiazol-2-yl)(pyrimidin-2-yl)amino)ethanol was synthesized from 4-(pyridin-2-yl)-N-(pyrimidin-2-yl)thiazol-2-amine and 2-bromoethanol in the same manner as Example 45 to provide the product as a white solid. $^1$H NMR (300 MHz, CDCl$_3$): δ 8.63-8.60 (m, 3H, CH$_{ar}$), 8.02 (d, J=7.8 Hz, 1H, CH$_{ar}$), 7.79-7.73 (m, 2H, CH$_{ar}$), 7.23-7.18 (m, 1H, CH$_{ar}$), 6.93 (t, J=4.8 Hz, 1H, CH$_{ar}$), 4.94 (t, J=5.1 Hz, 2H, NCH$_2$), 4.71 (t, J=4.5 Hz, 1H, OH), 4.20-4.15 (m, 2H, OCH$_2$). MS: MH$^+$=300.

Example 49: Synthesis of 5-bromo-4-(pyridin-2-yl)-N-(pyrimidin-2-yl)thiazol-2-amine To a suspension of 4-(pyridin-2-yl)-N-(pyrimidin-2-yl)thiazol-2-amine (102 mg, 0.4 mmol) in acetic acid (2 mL), was added bromine at room temperature. Stirring was continued for 2 hours, and then ethyl acetate (20 mL) was added. The crude product was collected by filtration and re-crystallized in ethyl acetate to afford 130 mg of 5-bromo-4-(pyridin-2-yl)-N-(pyrimidin-2-yl)thiazol-2-amine as yellow solid. $^1$H NMR (300 MHz, DMSO-d$_6$): δ 8.73-8.67 (m, 3H, CH$_{ar}$), 8.10 (d, J=3.3 Hz, 2H, CH$_{ar}$), 7.57-7.53 (m, 1H, CH$_{ar}$), 7.11 (t, J=5.1 Hz, 1H, CH$_{ar}$). MS: MH$^+$=334.

Example 50: Synthesis of (4-(pyridin-2-yl)-2-(pyrimidin-2-ylamino)thiazol-5-yl)methanol

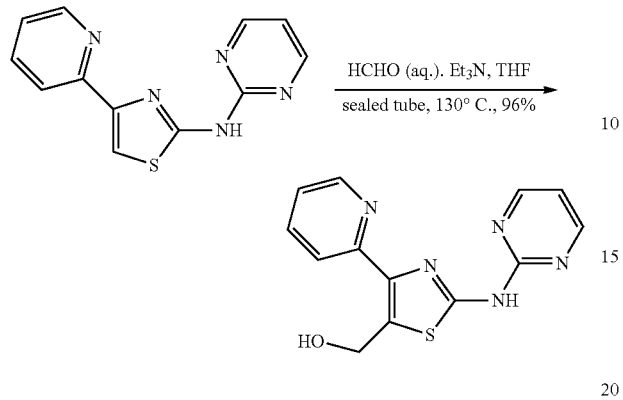

A suspension of 4-(pyridin-2-yl)-N-(pyrimidin-2-yl)thiazol-2-amine (51 mg, 0.2 mmol) in tetrahydrofuran (4 mL) in a sealed tube, was treated with aq. formaldehyde (36.5%, 2 mL), then triethylamine (0.6 mL). It was heated to 130° C. for 12 hours, then cooled down and concentrated. The residue was quenched with water (20 mL), stirred and filtered to give the product, which was washed with water and ethyl acetate in sequence and then dried under vacuum. 55 mg of pure compound (4-(pyridin-2-yl)-2-(pyrimidin-2-ylamino)thiazol-5-yl)methanol was obtained as white solid. $^1$H NMR (300 MHz, DMSO-d$_6$): δ 11.63 (s, 1H, NH), 8.63-8.59 (m, 3H, CH$_{ar}$), 8.00 (d, J=7.8 Hz, 1H, CH$_{ar}$), 7.87 (t, J=7.2 Hz, 1H, CH$_{ar}$), 7.30-7.26 (m, 1H, CH$_{ar}$), 7.02 (t, J=4.8 Hz, 1H, CH$_{ar}$), 5.81 (t, J=5.7 Hz, 1H, OH), 5.03 (d, J=5.7 Hz, 2H, OCH$_2$Ar). MS: MH$^+$=286.

Example 51: Synthesis of (4-(pyridin-2-yl)-2-(pyrimidin-2-ylamino)thiazol-5-yl)methyl acetate

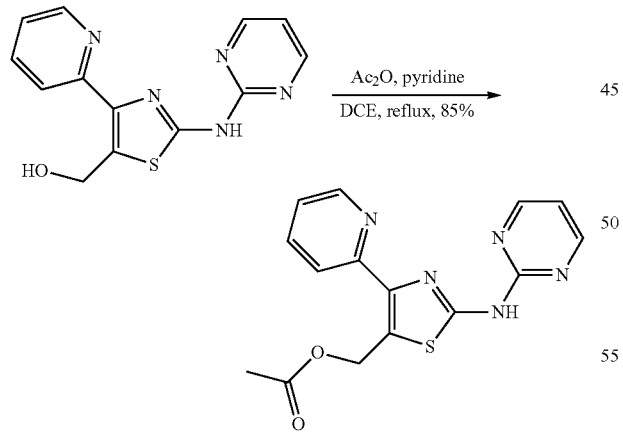

A suspension of (4-(pyridin-2-yl)-2-(pyrimidin-2-ylamino)thiazol-5-yl)methanol (29 mg, 0.1 mmol) in 1,2-dichloroethane (DCE, 5 mL) was treated with pyridine (81 µL, 1 mmol), followed by the addition of acetic anhydride (38 µL, 0.4 mmol) at room temperature. Then it was heated to reflux for 5 hours. After cooling down, the reaction was quenched with water (50 mL), the pH was adjusted to 10 by using powder sodium carbonate and extracted with dichloromethane (30 mL×4). The combined organic layer was dried over sodium sulfate, and then concentrated. The resulting residue was suspended in ethyl acetate, filtered and further washed with ethyl acetate. 28 mg of (4-(pyridin-2-yl)-2-(pyrimidin-2-ylamino)thiazol-5-yl)methyl acetate as white solid. MS: MH+=281

Example 52: Synthesis of (4-(pyridin-2-yl)-2-(pyrimidin-2-ylamino)thiazol-5-yl)methyl butyrate

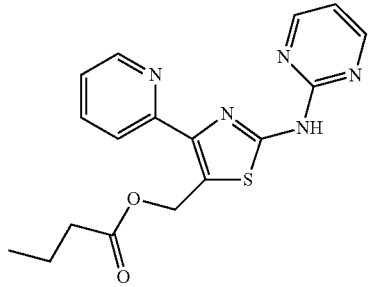 [SMILES: CCCC(=O)OCc1sc(Nc2ncccn2)nc1-c1ccccn1]

(4-(pyridin-2-yl)-2-(pyrimidin-2-ylamino)thiazol-5-yl)methyl butyrate was synthesized from (4-(pyridin-2-yl)-2-(pyrimidin-2-ylamino)thiazol-5-yl)methanol and butyric acid anhydride in the same manner as Example 49 to provide the product as a off-white solid in 57% yield. $^1$H NMR (300 MHz, CDCl$_3$): δ 9.84 (s, 1H, NH), 8.68-8.64 (m, 3H, CH$_{ar}$), 7.98 (d, J=7.8 Hz, 1H, CH$_{ar}$), 7.75 (dt, J=7.8, 2.1 Hz, 1H, CH$_{ar}$), 7.20 (dt, J=6.3, 1.2 Hz, 1H, CH$_{ar}$), 6.93 (t, J=4.8 Hz, 1H, CH$_{ar}$), 5.85 (s, 2H, ArCH$_2$O), 2.38 (t, J=7.5 Hz, 2H, CH$_2$CO), 1.74-1.67 (m, 2H, CH$_2$), 0.97 (t, J=7.5, 3H, CH$_3$). MS: MNa$^+$=378.

Example 53: Synthesis of ethyl 4-(pyridin-2-yl)-2-(pyrimidin-2-ylamino)thiazole-5-carboxylate

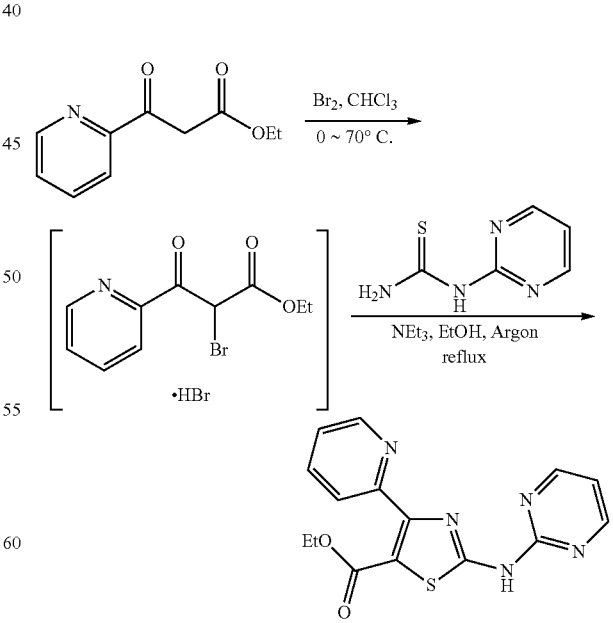

To a stirred solution of ethyl 3-oxo-3-(pyridin-2-yl)propanoate (1.16 g, 6 mmol) in CHCl$_3$ (20 mL) at 0° C., was added dropwise bromine (339 µL, 6.6 mmol). The reaction mixture was firstly stirred at 40° C. for 1 hr, and then 70° C. for another hour. The solvent was evaporated to give the crude ethyl 2-bromo-3-oxo-3-(pyridin-2-yl)propanoate hydrobromide.

A reaction mixture of crude ethyl 2-bromo-3-oxo-3-(pyridin-2-yl)propanoate hydrobromide, 1-(pyrimidin-2-yl)thiourea (617 mg, 4 mmol), and triethylamine (1.94 mL, 14 mmol) in ethanol (20 mL) was refluxed for 1 hour under argon atmosphere. After cooling to room temperature, the reaction mixture was quenched with water (200 mL) and stirred for 30 minutes. Then it was filtered and the collected solid was slurried in ethyl acetate/hexanes (1:1, 20 mL). After filtration and drying under vacuum, 910 mg of ethyl 4-(pyridin-2-yl)-2-(pyrimidin-2-ylamino)thiazole-5-carboxylate afforded as brown-reddish solid. $^1$H NMR (300 MHz, DMSO-d$_6$): δ 12.34 (s, 1H, NH), 8.73 (d, J=4.5 Hz, 2H, CH$_{ar}$), 8.60 (d, J=3.9 Hz, 1H, CH$_{ar}$), 7.86 (dt, J=7.8, 1.8 Hz, 1H, CH$_{ar}$), 7.65 (d, J=7.5 Hz, 1H, CH$_{ar}$), 7.43-7.38 (m, 1H, CH$_{ar}$), 7.14 (t, J=5.1 Hz, 1H, CH$_{ar}$), 4.12 (q, J=7.2 Hz, 2H, OCH$_2$), 1.12 (t, J=7.2 Hz, 3H, CH$_3$). MS: MH$^+$=328.

Example 54: Synthesis of ethyl 4-(4-methylpyridin-2-yl)-2-(pyrimidin-2-ylamino)thiazole-5-carboxylate

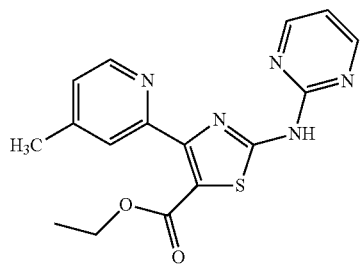 [SMILES: CCOC(=O)c1sc(Nc2ncccn2)nc1-c1cc(C)ccn1]

Ethyl 4-(4-methylpyridin-2-yl)-2-(pyrimidin-2-ylamino)thiazole-5-carboxylate was synthesized from pyrimidin-2-yl-thiourea and 3-(4-methyl-pyridin-2-yl)-3-oxo-propanoic acid ethyl ester in the same manner as Example 53 to provide the product as a gray solid. $^1$H NMR (300 MHz, CDCl$_3$): δ 8.72 (d, J=5.1 Hz, 2H, CH$_{ar}$), 8.59 (d, J=4.8 Hz, 1H, CH$_{ar}$), 7.62 (s, 1H, CH$_{ar}$), 7.15 (d, J=4.2 Hz, 1H, CH$_{ar}$), 6.98 (t, J=4.8 Hz, 1H, CH$_{ar}$), 4.28 (q, J=7.2 Hz, 2H, OCH$_2$), 2.43 (s, 3H, ArCH$_3$), 1.29 (t, J=7.2 Hz, 3H, CH$_3$). MS: MH$^+$=342.

Example 55: Synthesis of ethyl 4-(6-methylpyridin-2-yl)-2-(pyrimidin-2-ylamino)thiazole-5-carboxylate

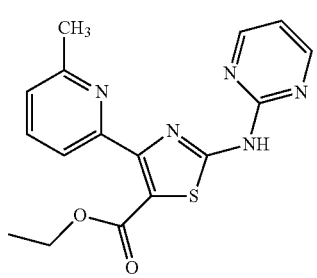 [SMILES: CCOC(=O)c1sc(Nc2ncccn2)nc1-c1cccc(C)n1]

Ethyl 4-(6-methylpyridin-2-yl)-2-(pyrimidin-2-ylamino)thiazole-5-carboxylate was synthesized from pyrimidin-2-yl-thiourea and 3-(6-methyl-pyridin-2-yl)-3-oxo-propionic acid ethyl ester in the same manner as Example 53 to provide the product as a brown-reddish solid. $^1$H NMR (300 MHz, CDCl$_3$): δ 9.95 (s, 1H, NH), 8.71 (d, J=4.2 Hz, 2H, CH$_{ar}$), 7.66 (t, J=7.5 Hz, 1H, CH$_{ar}$), 7.56 (d, J=7.8 Hz, 1H, CH$_{ar}$), 7.20 (d, J=7.5 Hz, 1H, CH$_{ar}$), 6.98 (m, 1H, CH$_{ar}$), 4.26 (q, J=7.2 Hz, 2H, OCH$_2$), 2.66 (s, 3H, ArCH$_3$), 1.28 (t, J=7.2 Hz, 3H, CH$_3$). MS: MH$^+$=342.

Example 56: Synthesis of ethyl 2-((4-methylpyrimidin-2-yl)amino)-4-(pyridin-2-yl)thiazole-5-carboxylate

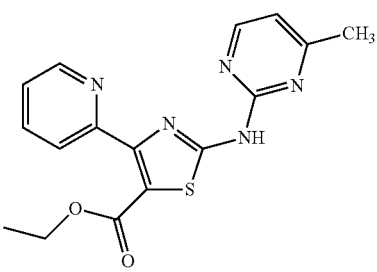 [SMILES: CCOC(=O)c1sc(Nc2nccc(C)n2)nc1-c1ccccn1]

Ethyl 2-((4-methylpyrimidin-2-yl)amino)-4-(pyridin-2-yl)thiazole-5-carboxylate was synthesized from (4-methylpyrimidin-2-yl)-thiourea and 3-oxo-3-pyridin-2-yl-propionic acid ethyl ester in the same manner as Example 53 to provide the product as a brown-reddish solid. $^1$H NMR (300 MHz, CDCl$_3$): δ 9.43 (s, 1H, NH), 8.74 (d, J=4.5 Hz, 1H, CH$_{ar}$), 8.51 (d, J=5.4 Hz, 1H, CH$_{ar}$), 7.82-7.73 (m, 2H, CH$_{ar}$), 7.32 (t, J=5.7 Hz, 1H, CH$_{ar}$), 6.84 (d, J=5.4 Hz, 1H, CH$_{ar}$), 4.27 (q, J=7.2 Hz, 2H, OCH$_2$), 2.56 (s, 3H, ArCH$_3$), 1.28 (t, J=7.5 Hz, 3H, CH$_3$). MS: MH$^+$=342.

Example 57: Synthesis of 4-(pyridin-2-yl)-2-(pyrimidin-2-ylamino)thiazole-5-carboxylic acid

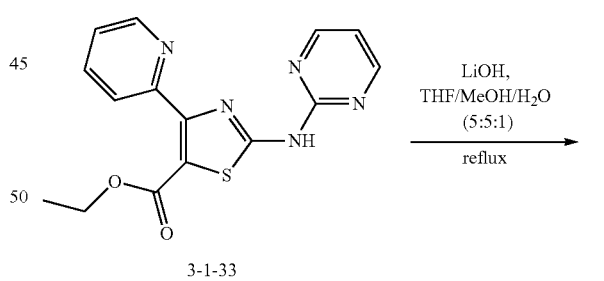

3-1-33

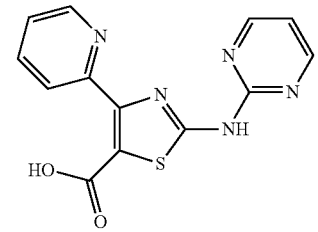

To a solution of ethyl 4-(pyridin-2-yl)-2-(pyrimidin-2-ylamino)thiazole-5-carboxylate (435 mg, 1.33 mmol) in tetrahydrofuran/CH$_3$OH/H$_2$O (5:5:1, 16.5 mL) was added lithium hydroxide monohydrate (391 mg, 9.31 mmol). The reaction mixture was refluxed for 6 hours. After cooling down, the solvent was evaporated and water (20 mL) was added to dissolve the residue. The pH was adjusted to 6 with aq. 6 M HCl and the mixture was stood at 4° C. for 16 hours. The precipitate was filtered, washed with water and dried under vacuum to give 385 mg of 4-(pyridin-2-yl)-2-(pyrimidin-2-ylamino)thiazole-5-carboxylic acid as light-brown solid. MS: MNa$^+$=322.

Example 58: Synthesis of methyl 4-(pyridin-2-yl)-2-(pyrimidin-2-ylamino)thiazole-5-carboxylate

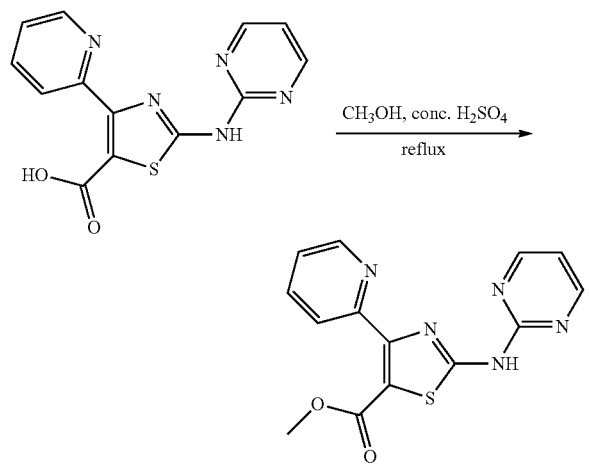

A suspension of 4-(pyridin-2-yl)-2-(pyrimidin-2-ylamino)thiazole-5-carboxylic acid (60 mg, 0.2 mmol) in methanol (10 mL) was treated with conc. sulfuric acid (~98%, 2 drops). The reaction mixture was refluxed for 4 days. After cooling down, the solvent was evaporated and water (20 mL) was added. The pH was adjusted to 8 by sat. sodium bicarbonate and the mixture was extracted with dichloromethane (20 mL×4). The combined organic layer was dried over anhydrous sodium sulfate and then evaporated to afford 26 mg of methyl 4-(pyridin-2-yl)-2-(pyrimidin-2-ylamino)thiazole-5-carboxylate as white solid. $^1$H NMR (300 MHz, DMSO-d$_6$): δ 12.37 (s, 1H, NH), 8.72 (d, J=4.2 Hz, 2H, CH$_{ar}$), 8.60 (d, J=3.3 Hz, 1H, CH$_{ar}$), 7.86 (t, J=7.5 Hz, 1H, CH$_{ar}$), 7.66 (d, J=7.5 Hz, 1H, CH$_{ar}$), 7.41 (t, J=5.7 Hz, 1H, CH$_{ar}$), 7.14 (t, J=4.8 Hz, 1H, CH$_{ar}$), 3.67 (s, 3H, OCH$_3$). MS: MH$^+$=314.

Example 59: Synthesis of tert-butyl 2-(tert-butyl (pyrimidin-2-yl)amino)-4-(pyridin-2-yl)thiazole-5-carboxylate

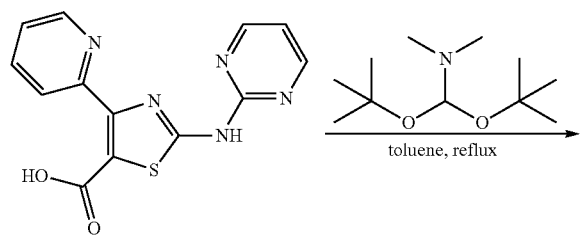

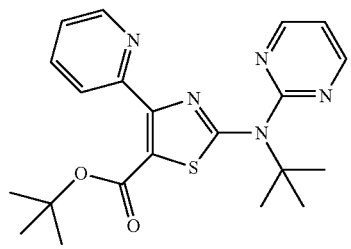

A mixture of 4-(pyridin-2-yl)-2-(pyrimidin-2-ylamino)thiazole-5-carboxylic acid (30 mg, 0.1 mmol) and 1,1-di-tert-butoxy-N,N-dimethylmethanamine (120 μL, 0.5 mmol) in toluene (2 mL) was heated to reflux for 24 hours. After cooling down, it was quenched with water (20 mL) and extracted with dichloromethane (10 mL×3). The combined organic layer was dried over sodium sulfate, concentrated, and then purified by preparative TLC (ethyl acetate: hexanes=30:70) to afforded 12 mg of tert-butyl 2-(tert-butyl (pyrimidin-2-yl)amino)-4-(pyridin-2-yl)thiazole-5-carboxylate as white solid. $^1$H NMR (300 MHz, DMSO-d$_6$): δ 8.61 (d, J=4.8 Hz, 3H, CH$_{ar}$), 7.87 (dt, J=7.8, 1.5 Hz, 1H, CH$_{ar}$), 7.67 (d, J=7.8 Hz, 1H, CH$_{ar}$), 7.43-7.38 (m, 1H, CH$_{ar}$), 7.09 (t, J=4.8 Hz, 1H, CH$_{ar}$), 1.55 (s, 9H, C(CH$_3$)$_3$), 1.31 (s, 9H, C(CH$_3$)$_3$). MS: MH$^+$=412.

Example 60: Synthesis of 4-(pyridin-2-yl)-2-(pyrimidin-2-ylamino)thiazole-5-carboxamide

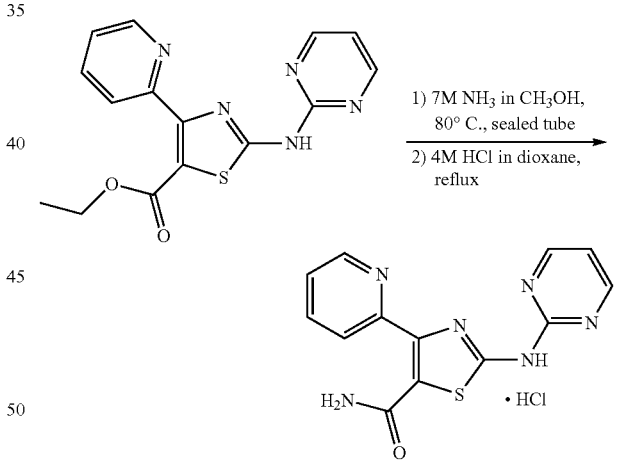

In a sealed tube, a suspension of ethyl 4-(pyridin-2-yl)-2-(pyrimidin-2-ylamino)thiazole-5-carboxylate (16 mg, 0.05 mg) in 7M NH$_3$ solution in methanol (5 mL) was heated to 80° C. for 7 days. The solvent was evaporated and the residue was washed with ethyl acetate to give the pure amide. It was suspended in methanol, treated with 4 M HCl in dioxane (0.4 mL) and heated to reflux. The solvent was removed by evaporation and the crude product was washed with ethyl acetate to give 17 mg of 4-(pyridin-2-yl)-2-(pyrimidin-2-ylamino)thiazole-5-carboxamide as light-yellow solid. $^1$H NMR (300 MHz, CD$_3$OD): δ 8.93-8.89 (m, 2H, CH$_{ar}$), 8.71-8.63 (m, 3H, CH$_{ar}$), 8.04 (t, J=6.6 Hz, 1H, CH$_{ar}$), 7.14 (t, J=5.1 Hz, 1H, CH$_{ar}$). MS: MH$^+$=299.

Example 61: Synthesis of N-methyl-4-(pyridin-2-yl)-2-(pyrimidin-2-ylamino)thiazole-5-carboxamide

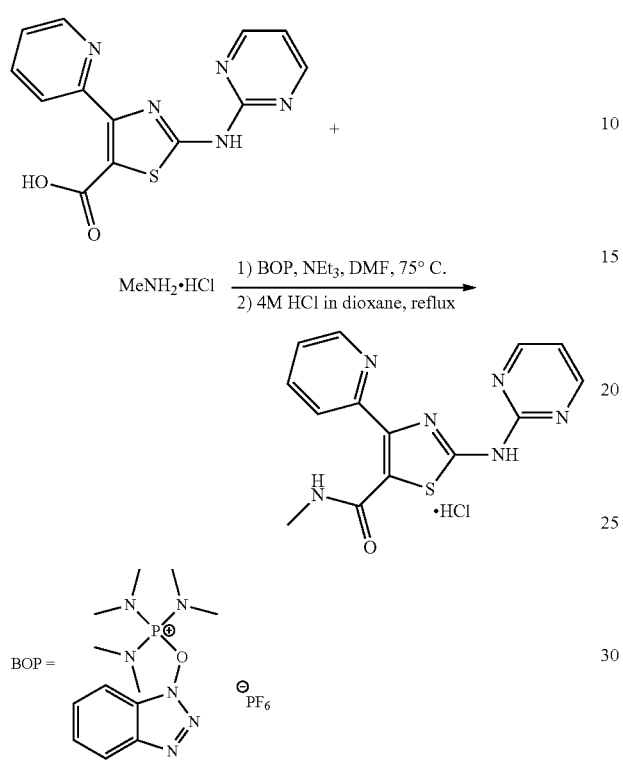

A reaction mixture of 4-(pyridin-2-yl)-2-(pyrimidin-2-ylamino)thiazole-5-carboxylic acid (60 mg, 0.2 mmol), methylamine hydrochloride (27 mg, 0.4 mmol), benzotriazole-1-yl-oxy-tris-(dimethylamino)-phosphonium hexafluorophosphate (BOP, 221 mg, 0.5 mmol), triethylamine (83 μL, 0.6 mmol) in dimethylformamide (2 mL) in a sealed tube was heated to 75° C. for 24 hours. Then it was quenched with water (20 mL), filtered and washed with water. The solid was suspended in methanol (2 mL) and treated with 4 M HCl in dioxane (0.6 mL). It was heated to reflux, and then evaporated to remove solvent. The resulting solid was washed with ethyl acetate and dried under vacuum to give 64 mg of the N-methyl-4-(pyridin-2-yl)-2-(pyrimidin-2-ylamino)thiazole-5-carboxamide hydrochloride as light-yellow solid. $^1$H NMR (300 MHz, DMSO-$d_6$): δ 8.85 (m, 1H, CH$_{ar}$), 8.72 (d, J=4.8 Hz, 2H, CH$_{ar}$), 8.93-8.29 (m, 2H, CH$_{ar}$), 7.72 (m, 1H, CH$_{ar}$), 7.13 (m, 1H, CH$_{ar}$), 2.85 (s, 3H, NCH$_3$). MS: MH$^+$=313.

Example 62: Synthesis of N-benzyl-4-(pyridin-2-yl)-2-(pyrimidin-2-ylamino)thiazole-5-carboxamide

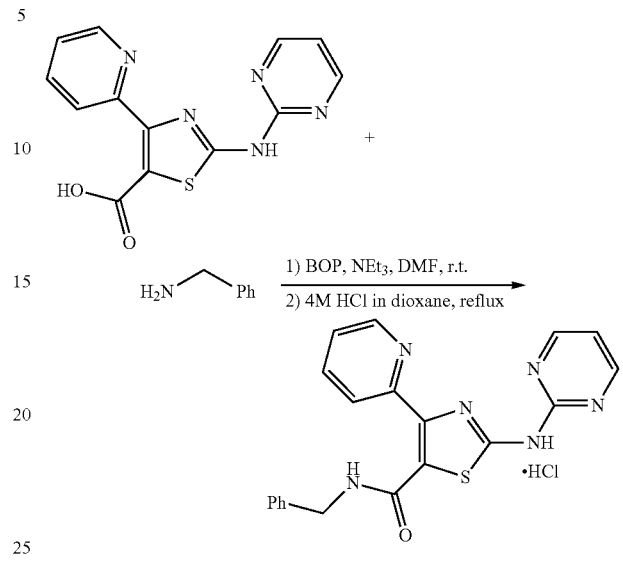

A reaction mixture of 4-(pyridin-2-yl)-2-(pyrimidin-2-ylamino)thiazole-5-carboxylic acid (60 mg, 0.2 mmol), benzylamine (43 mg, 0.4 mmol), benzotriazole-1-yl-oxy-tris-(dimethylamino)-phosphonium hexafluorophosphate (BOP, 195 mg, 0.44 mmol), triethylamine (83 μL, 0.6 mmol) in dimethylformamide (10 mL) was stirred for 4 days. Then it was quenched with water (50 mL), filtered and washed with water. The solid was suspended in methanol/dichloromethane (4:6) and then filtered. The filtrate was concentrated to give 24 mg of the amide as off-white solid in 31% yield. 8 mg of the above amide was suspended in methanol (1 mL) and treated with 4 M HCl in dioxane (0.3 mL). It was heated to reflux, and then evaporated to remove solvent. The resulting solid was washed with ethyl acetate and dried under vacuum to give 9 mg N-benzyl-4-(pyridin-2-yl)-2-(pyrimidin-2-ylamino)thiazole-5-carboxamide hydrochloride as an off-white solid. $^1$H NMR (300 MHz, DMSO-$d_6$): δ 12.29 (br, 1H, NH), 12.09 (br, 1H, NH), 8.71 (d, J=4.5 Hz, 2H, CH$_{ar}$), 8.40 (s, 1H, CH$_{ar}$), 8.32 (d, J=8.4 Hz, 1H, CH$_{ar}$), 8.09 (t, J=7.5 Hz, 1H, CH$_{ar}$), 7.51 (m, 1H, CH$_{ar}$), 7.37-7.28 (m, 5H, CH$_{ar}$), 7.11 (m, 1H, CH$_{ar}$), 4.52 (d, J=4.5 Hz, 2H, ArCH$_2$N). MS: MH$^+$=389.

Example 63: Synthesis of the MTX Derivative, 24-(4-(((2,4-diaminopteridin-6-yl)methyl)(methyl)amino)benzamido)-1,21-dioxo-1-(4-(pyridin-2-yl)-2-(pyrimidin-2-ylamino) thiazol-5-yl)-5,8,11,14,17-penta oxa-2,20-diazapentacosan-25-oic acid tri-trifluoroacetate

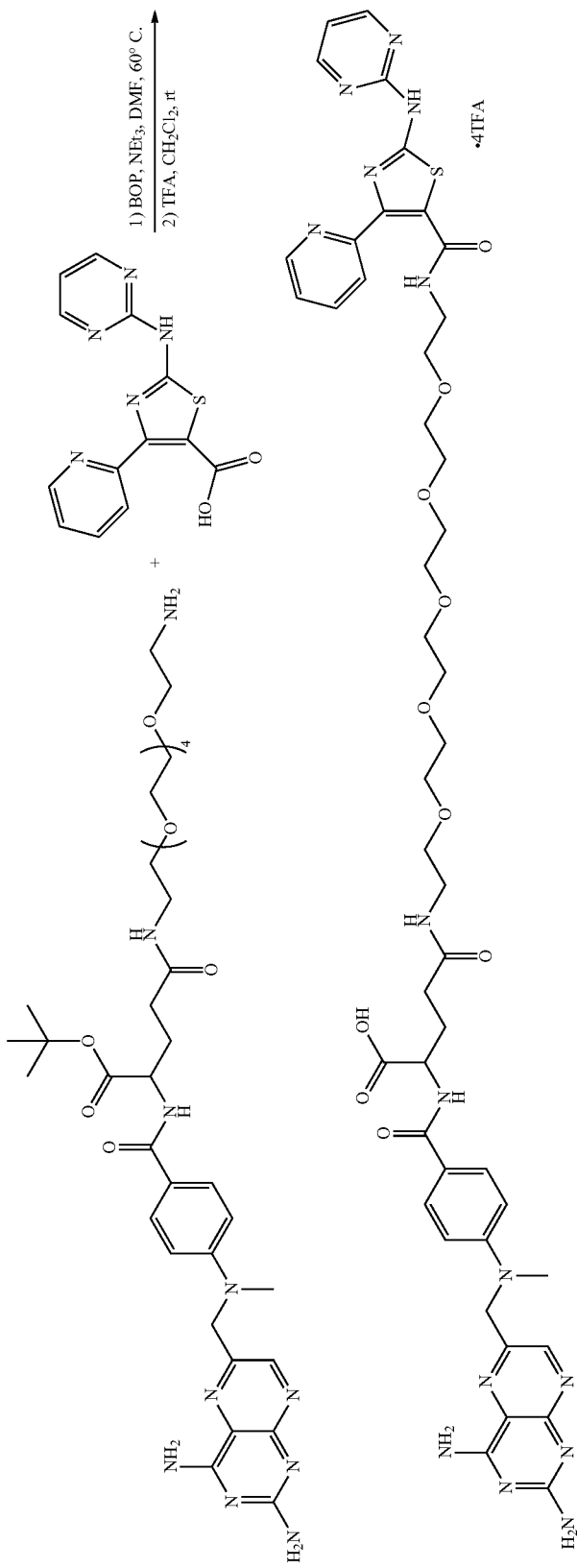

In a sealed tube, a reaction mixture of 4-(pyridin-2-yl)-2-(pyrimidin-2-ylamino)thiazole-5-carboxylic acid (66 mg, 0.22 mmol), tert-butyl 1-amino-22-(4-(((2,4-diaminopteridin-6-yl)methyl) (methyl)amino)benzamido)-19-oxo-3,6,9,12,15-pentaoxa-18-azatricosan-23-oate (MTX($CO_2Bu^t$)-(PEG)$_6$-NH$_2$, 170 mg, 0.22 mmol), benzotriazole-1-yl-oxy-tris-(dimethylamino)-phosphonium hexafluorophosphate (BOP, 146 mg, 0.33 mmol), triethylamine (55 μL, 0.4 mmol) in dimethylformamide (2 mL) was heated to 60° C. for 48 hours. After cooling to room temperature, it was quenched with water (30 mL), filtered and washed with water. The solid was dried, and then suspended in a mixture of dichloromethane and methanol (6:4, 30 mL). It was filtered and the filtrate was concentrated to give the pure tert-butyl ester, which was treated with dichloromethane (10 mL), followed by addition of trifluoroacetic acid (2 mL). The mixture was stirred at room temperature for 24 hours and evaporated to give 268 mg of 24-(4-(((2,4-diaminopteridin-6-yl)methyl) (methyl)amino)benzamido)-1,21-dioxo-1-(4-(pyridin-2-yl)-2-(pyrimidin-2-ylamino)thiazol-5-yl)-5,8,11,14,17-penta oxa-2,20-diazapentacosan-25-oic acid tri-trifluoroacetate as brown-reddish solid. $^1$H NMR (300 MHz, CD$_3$OD): δ 8.78 (d, J=4.5 Hz, 1H, CH$_{ar}$), 8.62-8.57 (m, 4H, CH$_{ar}$), 8.37 (t, J=7.8 Hz, 1H, CH$_{ar}$), 7.79 (t, J=6.3 Hz, 1H, CH$_{ar}$), 7.71 (d, J=9.0 Hz, 2H, CH$_{ar}$), 7.06 (t, J=4.8 Hz, 1H, CH$_{ar}$), 6.78 (d, J=8.7 Hz, 2H, CH$_{ar}$), 4.85 (s, 2H, ArCH$_2$N), 4.55-4.50 (m, 1H, CH), 3.70-3.42 (m, 24H), 3.21 (s, 3H, NCH$_3$), 2.38-2.07 (m, 4H). MS: MNa$^+$=1020.

Example 64: Synthesis of the Biotin derivative, N-(31-oxo-35-((3aS,4S,6aR)-2-oxohexahydro-1H-thieno[3,4-d]imidazol-4-yl)-3,6,9,12,15,18,21,24,27-nonaoxa-30-azapentatriacontyl)-4-(pyridin-2-yl)-2-(pyrimidin-2-ylamino)thiazole-5-carboxamide

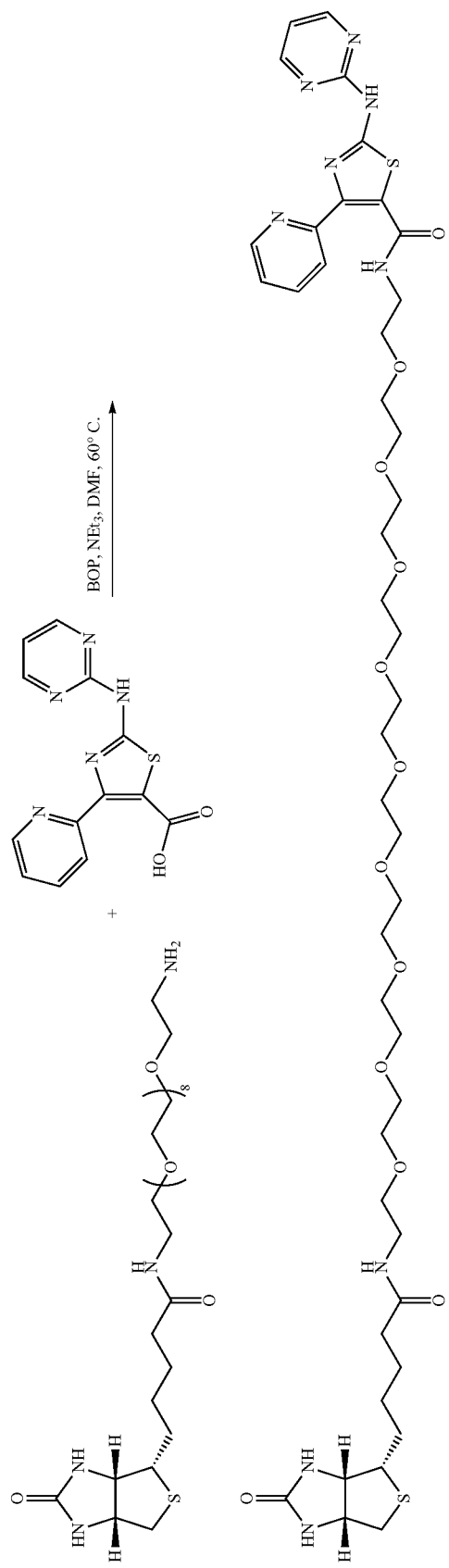

In a sealed tube, a reaction mixture of 4-(pyridin-2-yl)-2-(pyrimidin-2-ylamino)thiazole-5-carboxylic acid (30 mg, 0.1 mmol), N-(29-amino-3,6,9,12,15,18,21,24,27-nonaoxanonacosyl)-5-((3aS,4S,6aR)-2-oxohexa hydro-1H-thieno[3,4-d]imidazol-4-yl)pentanamide (Biotin-(PEG)$_{10}$-NH$_2$, 68 mg, 0.1 mmol), benzotriazole-1-yl-oxy-tris-(dimethylamino)-phosphonium hexafluorophosphate (BOP, 66 mg, 0.15 mmol), triethylamine (28 µL, 0.2 mmol) in dimethylformamide (2 mL) was heated to 60° C. for 48 hours. After cooling to room temperature, it was quenched with water (20 mL) and extracted with dichloromethane (20 mL×4). The combined organic layer was dried over sodium sulfate, concentrated, and then purified by preparative TLC (2 M NH$_3$ in methanol:dichloromethane=5:95) to afford 49 mg of N-(31-oxo-35-((3aS,4S,6aR)-2-oxohexahydro-1H-thieno[3,4-d]imidazol-4-yl)-3,6,9,12,15,18,21,24,27-nonaoxa-30-azapentatriacontyl)-4-(pyridin-2-yl)-2-(pyrimidin-2-ylamino)thiazole-5-carboxamide as white solid. $^1$H NMR (300 MHz, CD$_3$OD): δ 8.70 (m, 1H, CH$_{ar}$), 8.61 (d, J=4.8 Hz, 2H, CH$_{ar}$), 8.43 (d, J=8.1 Hz, 1H, CH$_{ar}$), 7.96 (t, J=7.8 Hz, 1H, CH$_{ar}$), 7.88 (s, 1H, NH), 7.44 (t, J=5.7 Hz, 1H, CH$_{ar}$), 7.00 (t, J=4.8 Hz, 1H, CH$_{ar}$), 4.48-4.44 (m, 1H, CH), 4.29-4.25 (m, 1H, CH), 3.74-3.49 (m, 40H), 3.18-3.12 (m, 1H, CH), 2.88 (dd, J=12.9, 5.4 Hz, 1H, CH), 2.68 (d, J=12.9 Hz, 1H, CH), 2.20-2.14 (m, 2H), 1.71-1.53 (m, 4H), 1.44-1.37 (m, 2H). MS: MNa$^+$=986.

Example 65: Synthesis of 2-Bromo-3-oxo-3-pyridin-2-yl-propionitrile hydrobromide

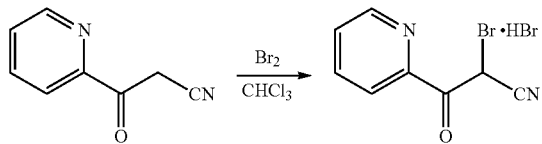

Bromine (4 ml, 0.8 mmol, 1 eq) was added dropwise to a solution of 3-oxo-3-pyridin-2-yl-propionitrile (117 mg, 0.8 mmol, 1 eq) in CHCl$_3$ (5 ml) at 0-5° C. Then the reaction mixture was heated to 40° C. for 1 hour and 70° C. for another hour. The reaction mixture was evaporated to remove the solvents and the crude product was used directly for next step.

Example 66: Synthesis of 4-Pyridin-2-yl-2-(pyrimidin-2-ylamino)-thiazole-5-carbonitrile

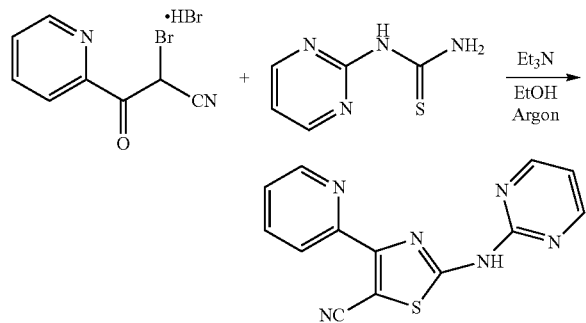

2-Bromo-3-oxo-3-pyridin-2-yl-propionitrile hydrobromide (46 mg, 0.3 mmol), 1-(pyrimidin-2-yl)thiourea (0.6 mmol) and triethylamine (0.83 ml, 6 mmol, 15 eq) were mixed together in ethanol (5 ml) under argon and refluxed for 1 hour. After cooling to room temperature, the reaction was quenched with water (10 ml) and then extracted with a 3 to 1 mixture of methanol and methylene chloride (1:3) (5 ml×3). The combined organic phase was evaporated. The title compound was obtained by column chromatography. MS: MH+=281.

FORMULATIONS

The present invention also relates to compositions or formulations which comprise the substituted aminothiazoles according to the present invention. In general, the compositions of the present invention comprise an effective amount of one or more substituted aminothiazoles and salts thereof according to the present invention which are effective for providing treatment or preventing diseases that involve unregulated cell growth; and one or more excipients. The compositions of the present invention also comprise an effective amount of one or more substituted aminothiazoles and salts thereof according to the present invention which are effective for treating or preventing diseases that involve infection with a hepatitis virus; and one or more excipients.

For the purposes of the present invention the term "excipient" and "carrier" are used interchangeably throughout the description of the present invention and said terms are defined herein as, "ingredients which are used in the practice of formulating a safe and effective pharmaceutical composition."

The formulator will understand that excipients are used primarily to serve in delivering a safe, stable, and functional pharmaceutical, serving not only as part of the overall vehicle for delivery but also as a means for achieving effective absorption by the recipient of the active ingredient. An excipient may fill a role as simple and direct as being an inert filler, or an excipient as used herein may be part of a pH stabilizing system or coating to insure delivery of the ingredients safely to the stomach. The formulator can also take advantage of the fact the compounds of the present invention have improved cellular potency, pharmacokinetic properties, as well as improved oral bioavailability.

The present teachings also provide pharmaceutical compositions that include at least one compound described herein and one or more pharmaceutically acceptable carriers, excipients, or diluents. Examples of such carriers are well known to those skilled in the art and can be prepared in accordance with acceptable pharmaceutical procedures, such as, for example, those described in *Remington's Pharmaceutical Sciences,* 17th edition, ed. Alfonoso R. Gennaro, Mack Publishing Company, Easton, Pa. (1985), the entire disclosure of which is incorporated by reference herein for all purposes. As used herein, "pharmaceutically acceptable" refers to a substance that is acceptable for use in pharmaceutical applications from a toxicological perspective and does not adversely interact with the active ingredient. Accordingly, pharmaceutically acceptable carriers are those that are compatible with the other ingredients in the formulation and are biologically acceptable. Supplementary active ingredients can also be incorporated into the pharmaceutical compositions.

Compounds of the present teachings can be administered orally or parenterally, neat or in combination with conventional pharmaceutical carriers. Applicable solid carriers can include one or more substances which can also act as flavoring agents, lubricants, solubilizers, suspending agents, fillers, glidants, compression aids, binders or tablet-disintegrating agents, or encapsulating materials. The compounds can be formulated in conventional manner, for example, in a manner similar to that used for known anti-cancer agents. The compounds can also be formulated in conventional manner, for example, in a manner similar to that used for known anti-viral agents. Oral formulations containing a compound disclosed herein can comprise any conventionally used oral form, including tablets, capsules, buccal forms, troches, lozenges and oral liquids, suspensions or solutions. In powders, the carrier can be a finely divided solid, which is an admixture with a finely divided compound. In tablets, a compound disclosed herein can be mixed with a carrier having the necessary compression properties in suitable proportions and compacted in the shape and size desired. The powders and tablets can contain up to 99% of the compound.

Capsules can contain mixtures of one or more compound(s) disclosed herein with inert filler(s) and/or diluent(s) such as pharmaceutically acceptable starches (e.g., corn, potato or tapioca starch), sugars, artificial sweetening agents, powdered celluloses (e.g., crystalline and microcrystalline celluloses), flours, gelatins, gums, and the like.

Useful tablet formulations can be made by conventional compression, wet granulation or dry granulation methods and utilize pharmaceutically acceptable diluents, binding agents, lubricants, disintegrants, surface modifying agents (including surfactants), suspending or stabilizing agents, including, but not limited to, magnesium stearate, stearic acid, sodium lauryl sulfate, talc, sugars, lactose, dextrin, starch, gelatin, cellulose, methyl cellulose, microcrystalline cellulose, sodium carboxymethyl cellulose, carboxymethylcellulose calcium, polyvinylpyrrolidine, alginic acid, acacia gum, xanthan gum, sodium citrate, complex silicates, calcium carbonate, glycine, sucrose, sorbitol, dicalcium phosphate, calcium sulfate, lactose, kaolin, mannitol, sodium chloride, low melting waxes, and ion exchange resins. Surface modifying agents include nonionic and anionic surface modifying agents. Representative examples of surface modifying agents include, but are not limited to, poloxamer 188, benzalkonium chloride, calcium stearate, cetostearl alcohol, cetomacrogol emulsifying wax, sorbitan esters, colloidal silicon dioxide, phosphates, sodium dodecylsulfate, magnesium aluminum silicate, and triethanolamine. Oral formulations herein can utilize standard delay or time-release formulations to alter the absorption of the compound(s). The oral formulation can also consist of administering a compound disclosed herein in water or fruit juice, containing appropriate solubilizers or emulsifiers as needed.

Liquid carriers can be used in preparing solutions, suspensions, emulsions, syrups, elixirs, and for inhaled delivery. A compound of the present teachings can be dissolved or suspended in a pharmaceutically acceptable liquid carrier such as water, an organic solvent, or a mixture of both, or a pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers, and osmo-regulators. Examples of liquid carriers for oral and parenteral administration include, but are not limited to, water (particularly containing additives as described herein, e.g., cellulose derivatives such as a sodium carboxymethyl cellulose solution), alcohols (including monohydric alcohols and polyhydric alcohols, e.g., glycols) and their derivatives, and oils (e.g., fractionated coconut oil and arachis oil). For parenteral administration, the carrier can be an oily ester such as ethyl oleate and isopropyl myristate. Sterile liquid carriers are used in sterile liquid form compositions for parenteral administration. The liquid carrier for pressurized compositions can be halogenated hydrocarbon or other pharmaceutically acceptable propellants.

Liquid pharmaceutical compositions, which are sterile solutions or suspensions, can be utilized by, for example, intramuscular, intraperitoneal or subcutaneous injection. Sterile solutions can also be administered intravenously. Compositions for oral administration can be in either liquid or solid form.

Preferably the pharmaceutical composition is in unit dosage form, for example, as tablets, capsules, powders, solutions, suspensions, emulsions, granules, or suppositories. In such form, the pharmaceutical composition can be sub-divided in unit dose(s) containing appropriate quantities of the compound. The unit dosage forms can be packaged compositions, for example, packeted powders, vials, ampoules, prefilled syringes or sachets containing liquids. Alternatively, the unit dosage form can be a capsule or tablet itself, or it can be the appropriate number of any such compositions in package form. Such unit dosage form can contain from about 1 mg/kg of compound to about 500 mg/kg of compound, and can be given in a single dose or in two or more doses. Such doses can be administered in any manner useful in directing the compound(s) to the recipient's bloodstream, including orally, via implants, parenterally (including intravenous, intraperitoneal and subcutaneous injections), rectally, vaginally, and transdermally.

When administered for the treatment or inhibition of a particular disease state or disorder, it is understood that an effective dosage can vary depending upon the particular compound utilized, the mode of administration, and severity of the condition being treated, as well as the various physical factors related to the individual being treated. In therapeutic applications, a compound of the present teachings can be provided to a patient already suffering from a disease in an amount sufficient to cure or at least partially ameliorate the symptoms of the disease and its complications. The dosage to be used in the treatment of a specific individual typically must be subjectively determined by the attending physician. The variables involved include the specific condition and its state as well as the size, age and response pattern of the patient.

In some cases it may be desirable to administer a compound directly to the airways of the patient, using devices such as, but not limited to, metered dose inhalers, breath-operated inhalers, multidose dry-powder inhalers, pumps, squeeze-actuated nebulized spray dispensers, aerosol dispensers, and aerosol nebulizers. For administration by intranasal or intrabronchial inhalation, the compounds of the present teachings can be formulated into a liquid composition, a solid composition, or an aerosol composition. The liquid composition can include, by way of illustration, one or more compounds of the present teachings dissolved, partially dissolved, or suspended in one or more pharmaceutically acceptable solvents and can be administered by, for example, a pump or a squeeze-actuated nebulized spray dispenser. The solvents can be, for example, isotonic saline or bacteriostatic water. The solid composition can be, by way of illustration, a powder preparation including one or more compounds of the present teachings intermixed with lactose or other inert powders that are acceptable for intrabronchial use, and can be administered by, for example, an aerosol dispenser or a device that breaks or punctures a capsule encasing the solid composition and delivers the solid composition for inhalation. The aerosol composition can include, by way of illustration, one or more compounds of the present teachings, propellants, surfactants, and co-solvents, and can be administered by, for example, a metered device. The propellants can be a chlorofluorocarbon (CFC), a hydrofluoroalkane (HFA), or other propellants that are physiologically and environmentally acceptable.

Compounds described herein can be administered parenterally or intraperitoneally. Solutions or suspensions of these compounds or a pharmaceutically acceptable salts, hydrates, or esters thereof can be prepared in water suitably mixed with a surfactant such as hydroxyl-propylcellulose. Dispersions can also be prepared in glycerol, liquid polyethylene glycols, and mixtures thereof in oils. Under ordinary conditions of storage and use, these preparations typically contain a preservative to inhibit the growth of microorganisms.

The pharmaceutical forms suitable for injection can include sterile aqueous solutions or dispersions and sterile powders for the extemporaneous preparation of sterile injectable solutions or dispersions. In some embodiments, the form can sterile and its viscosity permits it to flow through a syringe. The form preferably is stable under the conditions of manufacture and storage and can be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

Compounds described herein can be administered transdermally, i.e., administered across the surface of the body and the inner linings of bodily passages including epithelial and mucosal tissues. Such administration can be carried out using the compounds of the present teachings including pharmaceutically acceptable salts, hydrates, or esters thereof, in lotions, creams, foams, patches, suspensions, solutions, and suppositories (rectal and vaginal).

Transdermal administration can be accomplished through the use of a transdermal patch containing a compound, such as a compound disclosed herein, and a carrier that can be inert to the compound, can be non-toxic to the skin, and can allow delivery of the compound for systemic absorption into the blood stream via the skin. The carrier can take any number of forms such as creams and ointments, pastes, gels, and occlusive devices. The creams and ointments can be viscous liquid or semisolid emulsions of either the oil-in-water or water-in-oil type. Pastes comprised of absorptive powders dispersed in petroleum or hydrophilic petroleum containing the compound can also be suitable. A variety of occlusive devices can be used to release the compound into the blood stream, such as a semi-permeable membrane covering a reservoir containing the compound with or without a carrier, or a matrix containing the compound. Other occlusive devices are known in the literature.

Compounds described herein can be administered rectally or vaginally in the form of a conventional suppository. Suppository formulations can be made from traditional materials, including cocoa butter, with or without the addition of waxes to alter the suppository's melting point, and glycerin. Water-soluble suppository bases, such as polyethylene glycols of various molecular weights, can also be used.

Lipid formulations or nanocapsules can be used to introduce compounds of the present teachings into host cells either in vitro or in vivo. Lipid formulations and nanocapsules can be prepared by methods known in the art.

To increase the effectiveness of compounds of the present teachings, it can be desirable to combine a compound with other agents effective in the treatment of the target disease. For example, other active compounds (i.e., other active ingredients or agents) effective in treating the target disease can be administered with compounds of the present teachings. The other agents can be administered at the same time or at different times than the compounds disclosed herein.

Compounds of the present teachings can be useful for the treatment or inhibition of a pathological condition or disorder in a mammal, for example, a human subject. The present teachings accordingly provide methods of treating or inhibiting a pathological condition or disorder by providing to a mammal a compound of the present teachings including its pharmaceutically acceptable salt) or a pharmaceutical composition that includes one or more compounds of the present teachings in combination or association with pharmaceutically acceptable carriers. Compounds of the present teachings can be administered alone or in combination with other therapeutically effective compounds or therapies for the treatment or inhibition of the pathological condition or disorder.

Non-limiting examples of compositions according to the present invention include from about 0.001 mg to about 1000 mg of one or more according to the present invention and one or more excipients; from about 0.01 mg to about 100 mg of one or more substituted aminothiazoles according to the present invention and one or more excipients; and from about 0.1 mg to about 10 mg of one or more substituted aminothiazoles according to the present invention; and one or more excipients.

Procedures

The following procedures can be utilized in evaluating and selecting compounds as effective for providing treatment or preventing diseases that involve unregulated cell growth. The following procedures can also be utilized in evaluating and selecting compounds as effective for treating or preventing diseases that involve infection with a hepatitis virus.

Cell Cultures and Conditions

Huh-7 cells and derived from hepatocellular carcinoma cells, and were donated by Dr. Xuanyong Lu, (Drexel University College of Medicine, Doylestown, Pa.). THLE-2 were purchased from American Type Culture Collection (Manassas, Va.). PH5CH were donated by Dr. Masayuki Noguchi (University of Tsukuba, Ibaraki, Japan). THLE-2 and PH5CH have been immortalized through stable transfection of the SV40 large T antigen in normal hepatocytes, and are thus cell lines that are representative of normal hepatocytes rather than HCC cells. THLE2 have been confirmed to not form tumors in athymic mice. All cell lines were cultured and maintained in 5% $CO_2$ at 37° C. Huh-7 were maintained in the culture media DMEM/F12 (Dulbecco's Modified Eagle Medium) with 10% Fetal bovine serum (FBS), 100 µg/mL penicillin, 100 units/mL streptomycin, and 50 µg/mL normocin. THLE-2 and PH5CH were maintained in the culture media Brochial Epithelial Growth Media (BEGM) with 10% FBS, 100 µg/mL penicillin, 100 units/mL streptomycin, with the following additives form the prepackaged kit: Bovine pituitary extract (BPE), insulin, hydrocortisone, retinoic acid, transferrin, triiodothyronine, supplemented with 5 ng/ml human epidermal growth factor and 70 ng/ml phosphoethanolamine (Lonza Walkersville Inc., Walkersville, Md.).

Testing of Substituted Aminothiazole Analogues.

Huh7 cells were plated on 96-well plates at $2.0 \times 10^4$ cells per well to permit grow in the presence of compounds of the disclosure. Compounds of the disclosure were prediluted and transferred to cell plates by automated liquid handling. Cells were incubated with compounds of the disclosure for 72 hours, after which culture growth and viability were assessed by addition of 50 µg/mL 3-(4,5-Dimethyl-2-thiazolyl)-2,5-diphenyl-2H-tetrazolium bromide (MTT) incubation for 4 hours at 37° C. Solubilization buffer (0.01M HCl, 10% SDS) was added followed by incubation at 37° C. overnight. Absorbance was measured at 570 nm (reference 630 nm). Compound of the disclosure were tested in Huh7, THLE-2 and PH5CH, over eight-point dilutions in half-log steps, testing 50.0, 16.6, 5.0, 1.66, 0.5, 0.166, 0.05, and 0.016 µM in 0.5% DMSO, with each concentration in duplicate wells. The mean value of the reduction of viability signal in the MTT assay over the duplicate wells was used to determine the concentration that is cytoxic to 50% of the cells ($CC_{50}$), as compared to DMSO-only control wells (n=8), using curve-fitting analysis with XLfit (IDBS, Surrey, UK). Each compound was tested from 2 to 7 times in separate assay trials.

Selectivity of toxicity in HCC-derived cells over normal liver-derived cells is important for the purposes of developing a therapy that specifically targets the cancer with low toxicity for the whole tumor. The Selective Index (SI) is the ratio of $CC_{50}$ in normal cells (THLE2 or PH5CH) over the $CC_{50}$ in the liver cancer derived cells; thus, the higher the number, the lower the potential toxicity at an efficacious dose.

TABLE 2

Exemplary cell viability screening results for compounds of the disclosure with Huh-7 cells, THLE2 cells and PH5CH cells.

| Entry | Structure | Huh7 $CC_{50}$ (uM) | THLE2 $CC_{50}$ (uM) | THLE2/ Huh7 SI | PH5CH $CC_{50}$ (uM) | PH5CH/ Huh7 SI |
|---|---|---|---|---|---|---|
| 1 | 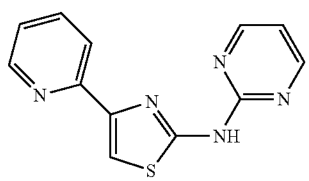 [SMILES: c1ccc(-c2csc(Nc3ncccn3)n2)nc1] | 1.387 | 39.982 | 28.833 | 50.000 | 36.058 |
| 2 | 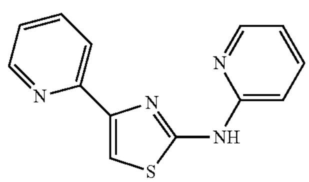 [SMILES: c1ccc(Nc2nc(-c3ccccn3)cs2)nc1] | 11.300 | 2.905 | 0.257 | | |
| 3 | 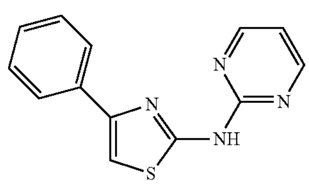 [SMILES: c1ccc(-c2csc(Nc3ncccn3)n2)cc1] | 6.433 | 9.156 | 1.423 | | |
| 4 | 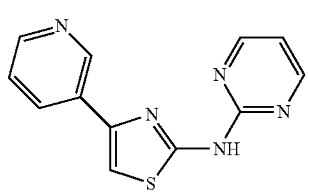 [SMILES: c1cnc(Nc2nc(-c3cccnc3)cs2)nc1] | 6.302 | 8.660 | 1.374 | | |
| 5 | 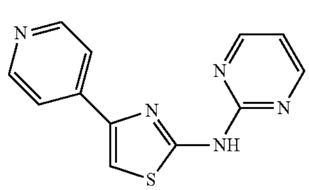 [SMILES: c1cnc(Nc2nc(-c3ccncc3)cs2)nc1] | 14.227 | 48.471 | 3.407 | | |

TABLE 2-continued
Exemplary cell viability screening results for compounds of the disclosure with Huh-7 cells, THLE2 cells and PH5CH cells.
| Entry | Structure | Huh7 CC$_{50}$ (uM) | THLE2 CC$_{50}$ (uM) | THLE2/ Huh7 SI | PH5CH CC$_{50}$ (uM) | PH5CH/ Huh7 SI |
|---|---|---|---|---|---|---|
| 6 | 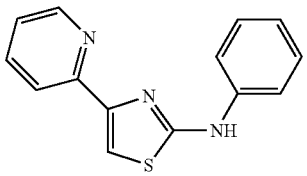 [SMILES: c1ccc(Nc2nc(-c3ccccn3)cs2)cc1] | 6.526 | 17.783 | 2.725 | | |
| 7 | 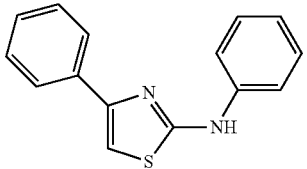 [SMILES: c1ccc(Nc2nc(-c3ccccc3)cs2)cc1] | 10.287 | 21.083 | 2.050 | | |
| 8 | 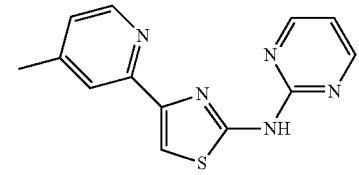 [SMILES: Cc1ccnc(-c2csc(Nc3ncccn3)n2)c1] | 0.563 | 14.018 | 24.905 | 33.973 | 60.358 |
| 9 | 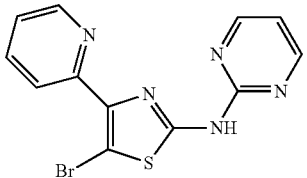 [SMILES: Brc1sc(Nc2ncccn2)nc1-c1ccccn1] | 2.532 | 29.911 | 11.816 | | |
| 10 | 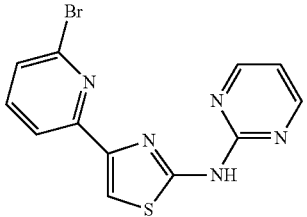 [SMILES: Brc1cccc(-c2csc(Nc3ncccn3)n2)n1] | 7.816 | 9.747 | 1.247 | | |
| 11 | 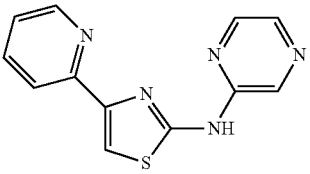 [SMILES: c1ccc(-c2csc(Nc3cnccn3)n2)nc1] | 5.000 | 0.539 | 0.108 | | |
| 12 | 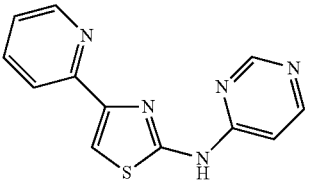 [SMILES: c1ccc(-c2csc(Nc3ccncn3)n2)nc1] | 3.053 | 4.471 | 1.464 | | |

TABLE 2-continued
Exemplary cell viability screening results for compounds of the disclosure with Huh-7 cells, THLE2 cells and PH5CH cells.
| Entry | Structure | Huh7 CC$_{50}$ (uM) | THLE2 CC$_{50}$ (uM) | THLE2/ Huh7 SI | PH5CH CC$_{50}$ (uM) | PH5CH/ Huh7 SI |
|---|---|---|---|---|---|---|
| 13 | 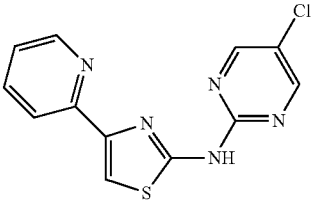 [SMILES: Clc1cnc(Nc2nc(-c3ccccn3)cs2)nc1] | 35.016 | 50.000 | 1.428 | | |
| 14 | 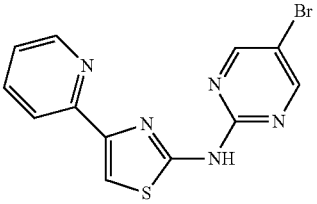 [SMILES: Brc1cnc(Nc2nc(-c3ccccn3)cs2)nc1] | 31.762 | 40.966 | 1.290 | | |
| 15 | 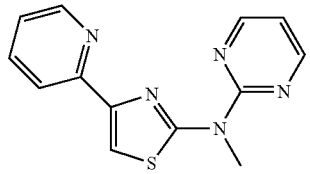 [SMILES: CN(c1ncccn1)c1nc(-c2ccccn2)cs1] | 5.317 | 49.120 | 9.238 | 49.728 | 9.353 |
| 16 | 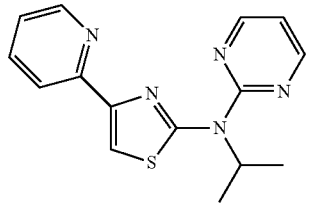 [SMILES: CC(C)N(c1ncccn1)c1nc(-c2ccccn2)cs1] | 25.705 | 50.000 | 1.945 | 50.000 | 1.945 |
| 17 | 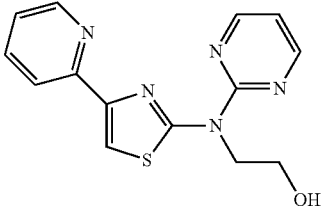 [SMILES: OCCN(c1ncccn1)c1nc(-c2ccccn2)cs1] | 48.942 | 50.000 | 1.022 | 50.000 | 1.022 |
| 18 | 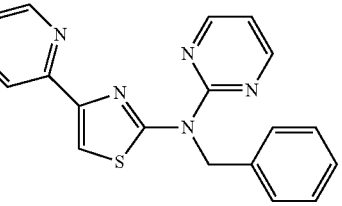 | 50.000 | 49.755 | 0.995 | 46.860 | 0.937 |

TABLE 2-continued

Exemplary cell viability screening results for compounds of the disclosure with Huh-7 cells, THLE2 cells and PH5CH cells.

| Entry | Structure | Huh7 CC$_{50}$ (uM) | THLE2 CC$_{50}$ (uM) | THLE2/ Huh7 SI | PH5CH CC$_{50}$ (uM) | PH5CH/ Huh7 SI |
|---|---|---|---|---|---|---|
| 19 | 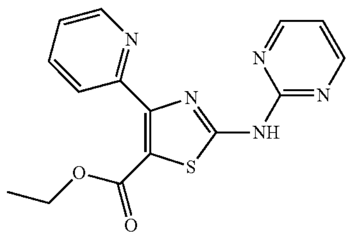 [SMILES: CCOC(=O)c1sc(Nc2ncccn2)nc1-c1ccccn1] | 0.362 | 38.709 | 106.972 | 44.017 | 121.642 |
| 20 | 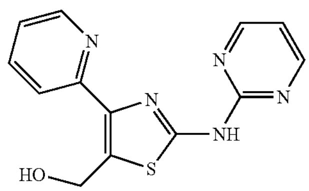 [SMILES: OCc1sc(Nc2ncccn2)nc1-c1ccccn1] | 11.329 | 31.137 | 2.748 | 46.868 | 4.137 |
| 21 | 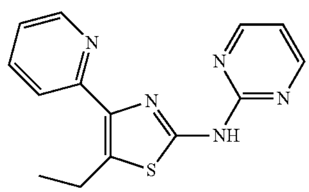 [SMILES: CCc1sc(Nc2ncccn2)nc1-c1ccccn1] | 15.436 | 24.733 | 1.602 | 44.128 | 2.859 |
| 22 | 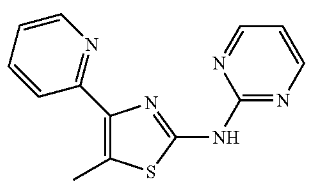 [SMILES: Cc1sc(Nc2ncccn2)nc1-c1ccccn1] | 5.925 | 42.852 | 7.232 | 41.985 | 7.086 |
| 23 | 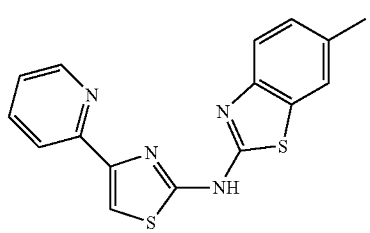 [SMILES: Cc1ccc2nc(Nc3nc(-c4ccccn4)cs3)sc2c1] | 4.917 | 3.959 | 0.805 | 3.970 | 0.807 |
| 24 | 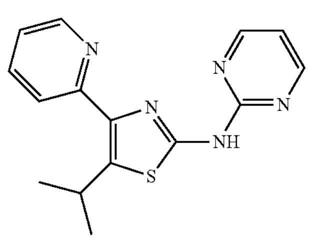 [SMILES: CC(C)c1sc(Nc2ncccn2)nc1-c1ccccn1] | 11.277 | 50.000 | 4.434 | 50.000 | 4.434 |

TABLE 2-continued

Exemplary cell viability screening results for compounds of the disclosure with Huh-7 cells, THLE2 cells and PH5CH cells.

| Entry | Structure | Huh7 CC$_{50}$ (uM) | THLE2 CC$_{50}$ (uM) | THLE2/ Huh7 SI | PH5CH CC$_{50}$ (uM) | PH5CH/ Huh7 SI |
|---|---|---|---|---|---|---|
| 25 | 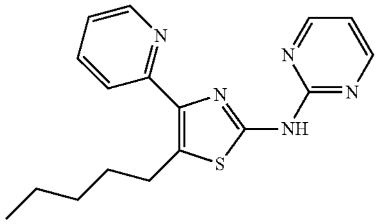 [SMILES: CCCCCc1sc(Nc2ncccn2)nc1-c1ccccn1] | 25.877 | 50.000 | 1.932 | 50.000 | 1.932 |
| 26 | 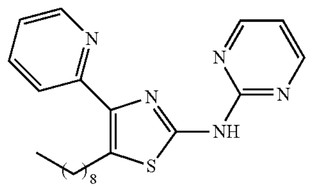 | 12.779 | 2.273 | 0.178 | 50.000 | 3.913 |
| 27 | 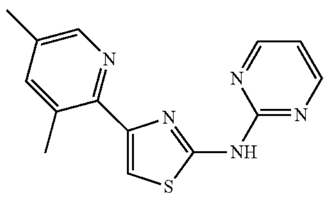 [SMILES: Cc1cnc(-c2csc(Nc3ncccn3)n2)c(C)c1] | 2.737 | 2.234 | 0.816 | 47.616 | 17.397 |
| 28 | 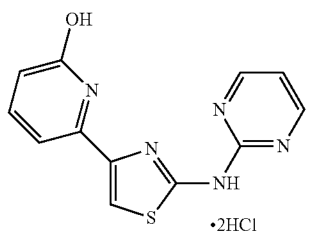 [SMILES: Oc1cccc(-c2csc(Nc3ncccn3)n2)n1] | 46.188 | 50.000 | 1.083 | 50.000 | 1.083 |
| 29 | 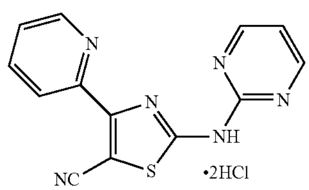 | 0.016 | 50.00 | 3125 | 50.00 | 3125 |
| 30 | 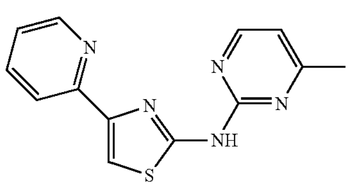 [SMILES: Cc1ccnc(Nc2nc(-c3ccccn3)cs2)n1] | 50.000 | 50.000 | 1.000 | 50.000 | 1.000 |
| 31 | 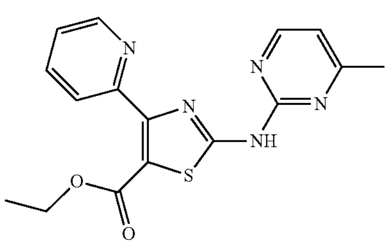 [SMILES: CCOC(=O)c1sc(Nc2nccc(C)n2)nc1-c1ccccn1] | 0.016 | 50.000 | 3125 | 50.000 | 3125 |

TABLE 2-continued

Exemplary cell viability screening results for compounds of the disclosure with Huh-7 cells, THLE2 cells and PH5CH cells.

| Entry | Structure | Huh7 CC$_{50}$ (uM) | THLE2 CC$_{50}$ (uM) | THLE2/ Huh7 SI | PH5CH CC$_{50}$ (uM) | PH5CH/ Huh7 SI |
|---|---|---|---|---|---|---|
| 32 | 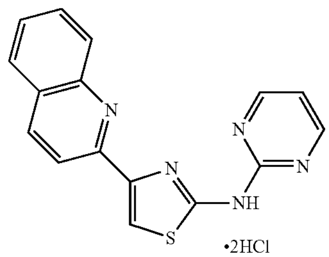 [SMILES: c1cnc(Nc2nc(-c3ccc4ccccc4n3)cs2)nc1] | 50.000 | 8.022 | 0.160 | 50.000 | 1.000 |
| 33 | 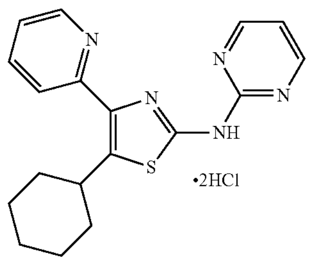 [SMILES: c1ccc(-c2nc(Nc3ncccn3)sc2C2CCCCC2)nc1] | 50.000 | 3.537 | 0.071 | 50.000 | 1.000 |
| 34 | 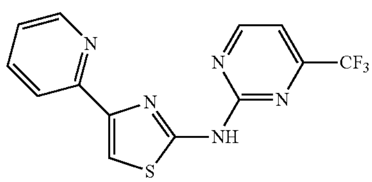 [SMILES: FC(F)(F)c1ccnc(Nc2nc(-c3ccccn3)cs2)n1] | 26.621 | 37.792 | 1.420 | 50.000 | 1.878 |
| 35 | 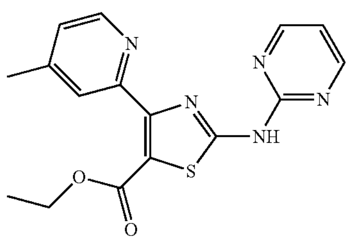 [SMILES: CCOC(=O)c1sc(Nc2ncccn2)nc1-c1cc(C)ccn1] | 4.717 | 37.206 | 7.888 | 39.233 | 8.317 |
| 36 | 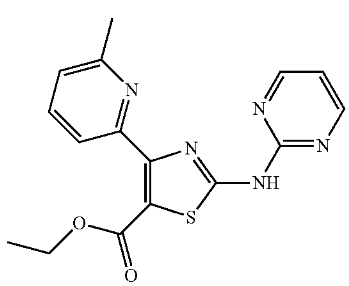 [SMILES: CCOC(=O)c1sc(Nc2ncccn2)nc1-c1cccc(C)n1] | 50.000 | 50.000 | 1.000 | 50.000 | 1.000 |
| 37 | 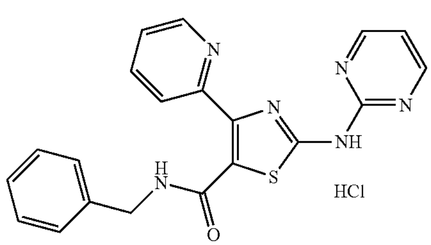 [SMILES: O=C(NCc1ccccc1)c1sc(Nc2ncccn2)nc1-c1ccccn1 ; Cl] | 17.742 | 50.000 | 2.818 | 31.485 | 1.775 |

TABLE 2-continued

Exemplary cell viability screening results for compounds of the disclosure with Huh-7 cells, THLE2 cells and PH5CH cells.

| Entry | Structure | Huh7 $CC_{50}$ (uM) | THLE2 $CC_{50}$ (uM) | THLE2/ Huh7 SI | PH5CH $CC_{50}$ (uM) | PH5CH/ Huh7 SI |
|---|---|---|---|---|---|---|
| 38 | 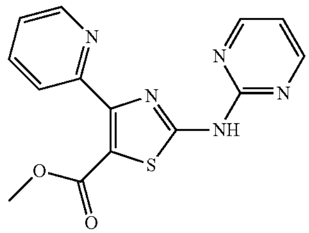 [SMILES: COC(=O)c1sc(Nc2ncccn2)nc1-c1ccccn1] | 1.246 | 29.395 | 23.591 | 38.599 | 30.978 |
| 39 | 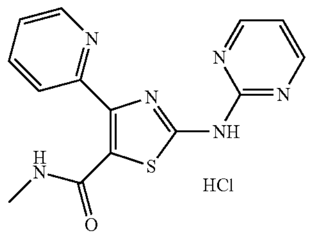 [SMILES: CNC(=O)c1sc(Nc2ncccn2)nc1-c1ccccn1 ; Cl] | 12.990 | 10.292 | 0.792 | 2.889 | 0.222 |
| 40 | 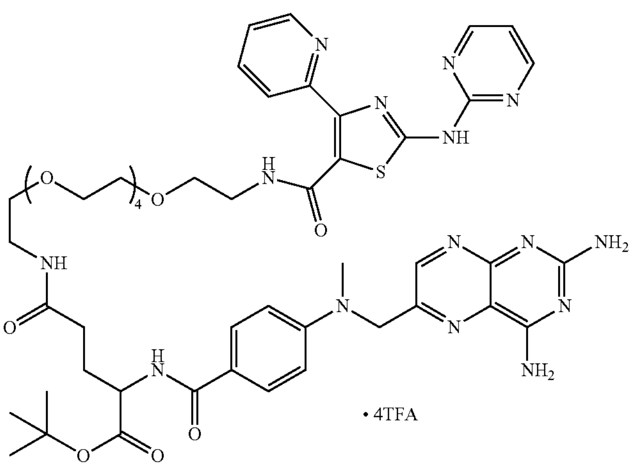 | 34.843 | 50.000 | 1.435 | 50.000 | 1.435 |
| 41 | 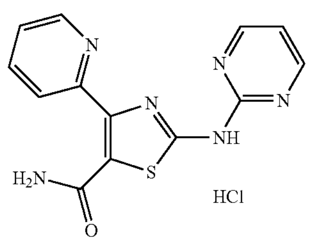 [SMILES: NC(=O)c1sc(Nc2ncccn2)nc1-c1ccccn1 ; Cl] | 50.000 | 26.614 | 0.532 | 50.000 | 1.000 |
| 42 | 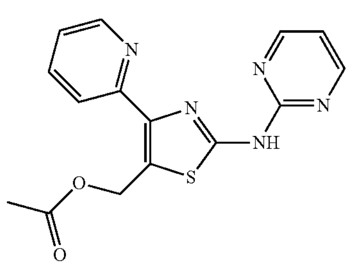 [SMILES: CC(=O)OCc1sc(Nc2ncccn2)nc1-c1ccccn1] | 39.251 | 50.000 | 1.274 | 50.000 | 1.274 |

TABLE 2-continued

Exemplary cell viability screening results for compounds of the disclosure with Huh-7 cells, THLE2 cells and PH5CH cells.

| Entry | Structure | Huh7 CC$_{50}$ (uM) | THLE2 CC$_{50}$ (uM) | THLE2/ Huh7 SI | PH5CH CC$_{50}$ (uM) | PH5CH/ Huh7 SI |
|---|---|---|---|---|---|---|
| 43 | 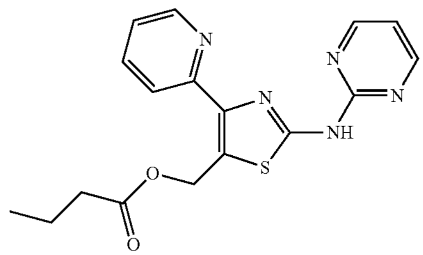 [SMILES: CCCC(=O)OCc1sc(Nc2ncccn2)nc1-c1ccccn1] | 11.003 | 50.000 | 4.544 | 50.000 | 4.544 |
| 44 | 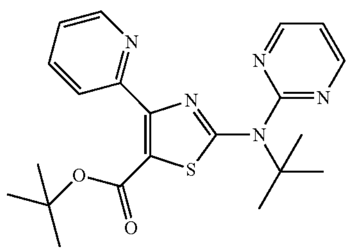 [SMILES: CC(C)(C)OC(=O)c1sc(N(c2ncccn2)C(C)(C)C)nc1-c1ccccn1] | 20.478 | 50.000 | 2.442 | 50.000 | 2.442 |
| 45 | 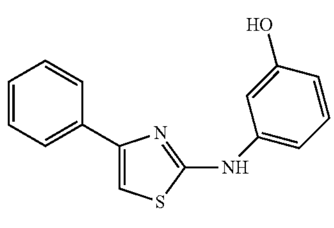 [SMILES: Oc1cccc(Nc2nc(-c3ccccc3)cs2)c1] | 8.000 | 50.000 | 6.250 | | |
| 46 | 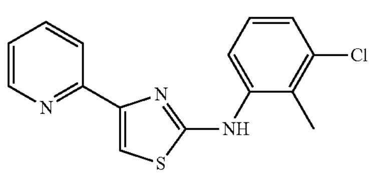 [SMILES: Cc1c(Cl)cccc1Nc1nc(-c2ccccn2)cs1] | 3.500 | Not tested | | | |
| 47 | 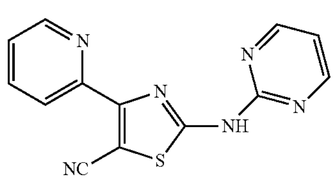 [SMILES: N#Cc1sc(Nc2ncccn2)nc1-c1ccccn1] | 0.016 | 50.000 | 3125.00 | 50.000 | 3125.00 |

TABLE 2-continued

Exemplary cell viability screening results for compounds of the disclosure with Huh-7 cells, THLE2 cells and PH5CH cells.

| Entry | Structure | Huh7 CC$_{50}$ (uM) | THLE2 CC$_{50}$ (uM) | THLE2/ Huh7 SI | PH5CH CC$_{50}$ (uM) | PH5CH/ Huh7 SI |
|---|---|---|---|---|---|---|
| 48 | 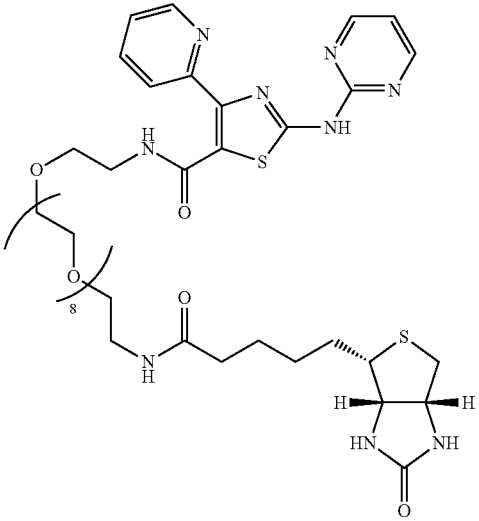 | | | | | |

What is claimed is:

1. A compound selected from:
(4-(pyridin-2-yl)-2-(pyrimidin-2-ylamino)thiazol-5-yl)methyl acetate;
(4-(pyridin-2-yl)-2-(pyrimidin-2-ylamino)thiazol-5-yl)methyl butyrate;
Ethyl 4-(pyridin-2-yl)-2-(pyrimidin-2-ylamino)thiazole-5-carboxylate;
Tert-butyl 2-(tert-butyl(pyrimidin-2-yl)amino)-4-(pyridine-2-yl)thiazole-5-carboxylate;
Ethyl 2-((4-methylpyrimidin-2-yl)amino)-4-(pyridin-2-yl)thiazole-5-carboxylate;
4-(pyridin-2-yl)-2-(pyrimidin-2-ylamino)thiazole-5-carboxylic acid;
Methyl 4-(pyridin-2-yl)-2-(pyrimidin-2-ylamino)thiazole-5-carboxylate;
and pharmaceutically acceptable salts thereof.

2. The compound of claim 1, wherein the compound is selected from:
Ethyl 4-(pyridin-2-yl)-2-(pyrimidin-2-ylamino)thiazole-5-carboxylate;
Ethyl 2-((4-methylpyrimidin-2-yl)amino)-4-(pyridin-2-yl)thiazole-5-carboxylate;
Methyl 4-(pyridin-2-yl)-2-(pyrimidin-2-ylamino)thiazole-5-carboxylate;
and pharmaceutically acceptable salts thereof.

3. 4-Pyridin-2-yl-2-(pyrimidin-2-ylamino)-thiazole-5-carbonitrile or a pharmaceutically acceptable salt thereof.

4. 4-Pyridin-2-yl-2-(pyrimidin-2-ylamino)-thiazole-5-carbonitrile hydrochloride.

5. A composition comprising a compound according to claim 1, and a pharmaceutically acceptable carrier.

* * * * *